United States Patent
Yoshida et al.

(10) Patent No.: US 11,065,226 B2
(45) Date of Patent: *Jul. 20, 2021

(54) COMBINATION COMPRISING EP4 ANTAGONIST AND IMMUNE CHECKPOINT INHIBITOR

(71) Applicant: ONO PHARMACEUTICAL CO., LTD., Osaka (JP)

(72) Inventors: Takao Yoshida, Osaka (JP); Akiko Shoyama, Osaka (JP); Hirotsugu Takano, Osaka (JP)

(73) Assignee: ONO PHARMACEUTICAL CO., LTD., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/315,063

(22) PCT Filed: Jul. 6, 2017

(86) PCT No.: PCT/JP2017/024753
§ 371 (c)(1),
(2) Date: Jan. 3, 2019

(87) PCT Pub. No.: WO2018/008711
PCT Pub. Date: Jan. 11, 2018

(65) Prior Publication Data
US 2019/0255013 A1    Aug. 22, 2019

Related U.S. Application Data

(60) Provisional application No. 62/359,504, filed on Jul. 7, 2016.

(51) Int. Cl.
| | |
|---|---|
| *A61K 31/352* | (2006.01) |
| *A61P 35/04* | (2006.01) |
| *C07K 16/28* | (2006.01) |
| *A61K 31/353* | (2006.01) |
| *A61P 43/00* | (2006.01) |
| *A61P 35/00* | (2006.01) |
| *A61K 31/277* | (2006.01) |
| *A61K 31/4433* | (2006.01) |
| *A61K 45/06* | (2006.01) |

(52) U.S. Cl.
CPC .......... *A61K 31/352* (2013.01); *A61K 31/277* (2013.01); *A61K 31/353* (2013.01); *A61K 31/4433* (2013.01); *A61P 35/00* (2018.01); *A61P 35/04* (2018.01); *A61P 43/00* (2018.01); *C07K 16/2818* (2013.01); *A61K 45/06* (2013.01)

(58) Field of Classification Search
CPC .. A61K 31/352; A61K 31/353; A61K 31/277; A61K 31/4433; A61K 45/06; A61K 39/39558; A61K 2300/00; A61P 43/00; A61P 35/00; A61P 35/04; C07K 16/2818

See application file for complete search history.

(56) References Cited

U.S. PATENT DOCUMENTS

| | | |
|---|---|---|
| 8,158,671 B2 | 4/2012 | Boyd et al. |
| 2003/0216381 A1 | 11/2003 | Tani et al. |
| 2006/0258728 A1 | 11/2006 | Tani et al. |
| 2009/0318518 A1 | 12/2009 | Boyd et al. |
| 2015/0004175 A1 | 1/2015 | Kaech et al. |
| 2018/0002308 A1 | 1/2018 | Asada et al. |
| 2018/0319764 A1 | 11/2018 | Asada et al. |

FOREIGN PATENT DOCUMENTS

| | | |
|---|---|---|
| CN | 101622230 A | 1/2010 |
| WO | 99/47497 A2 | 9/1999 |
| WO | 00/20371 A1 | 4/2000 |
| WO | 02/16311 A1 | 2/2002 |
| WO | 03/016254 A1 | 2/2003 |
| WO | 2013090552 A1 | 6/2013 |
| WO | 2015/179615 A1 | 11/2015 |

OTHER PUBLICATIONS

Bao et al., Combination of EP4 antagonist and checkpoint inhibitors promotes anti-tumor effector T cells in preclinical tumor models, Journal for ImmunoTherapy of Cancer 2015, 3(Suppl 2):p. 350 (Year: 2015).*

Negishi, et al., "Prostaglandin E receptors", 1995, Journal of Lipid Mediators and Cell Signalling, vol. 12, pp. 379-391.

Yokoyama, et al., "The Prostanoid EP4 Receptor and Its Signaling Pathway", Jul. 2013, Pharmacological Reviews, Vo. 65, pp. 1010-1052.

Gary, et al., "Abstract LB-265: ONO-AE3-208 inhibits myeloid derived suppressor cells and glioma growth", Apr. 2014, American Association for Cancer Research, 1 page total.

(Continued)

*Primary Examiner* — Sarah Pihonak
*Assistant Examiner* — Jason Deck
(74) *Attorney, Agent, or Firm* — Sughrue Mion, PLLC

(57) ABSTRACT

A medicament comprising a combination of a compound represented by formula (I),

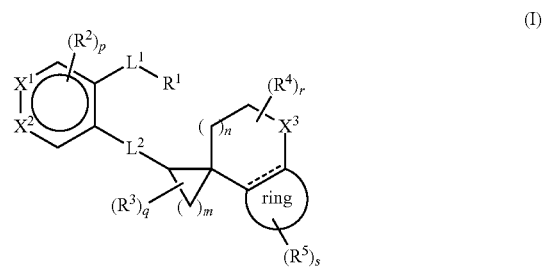

a salt thereof, a solvate thereof, an N-oxide thereof, or a prodrug of any of these and an immune checkpoint inhibitor (such as an anti-PD-1 antibody), which exhibits a strong anti-tumor effect and thus is useful for the treatment of cancer.

26 Claims, 3 Drawing Sheets
Specification includes a Sequence Listing.

(56) References Cited

OTHER PUBLICATIONS

Nishigaki, et al., "Identification of prostaglandin E receptor 'EP2' cloned from mastocytoma cells as EP4 subtype" 1995, FEBS Letters, vol. 364, pp. 339-341.
Majumder, et al., "Prostaglandin E2 receptor EP4 as the common target on cancer cells and macrophages to abolish angiogenesis, lymphangiogenesis, metastasis, and stem-like cell functions" Sep. 2014, Cancer Science, vol. 105, Issue 9, pp. 1142-1151.
Terada, et al., "Identification of EP4 as a Potential Target for the Treatment of Castration-Resistant Prostate Cancer Using a Novel Xenograft Model", Feb. 2010, Cancer Research, vol. 70, Issue 4, pp. 1606-1615.
Mutoh, et al., "Involvement of Prostaglandin E Receptor Subtype $EP_4$ in Colon Carcinogenesis", Jan. 2002, Cancer Research, vol. 62, pp. 28-32.
Search Report dated Aug. 8, 2017, issued by the International Searching Authority in counterpart International Patent Application No. PCT/JP2017/024753 (PCT/ISA/210).
Written Opinion dated Aug. 8, 2017, issued by the International Searching Authority in counterpart International Patent Application No. PCT/JP2017/024753 (PCT/ISA/237).

* cited by examiner

[FIG. 1]
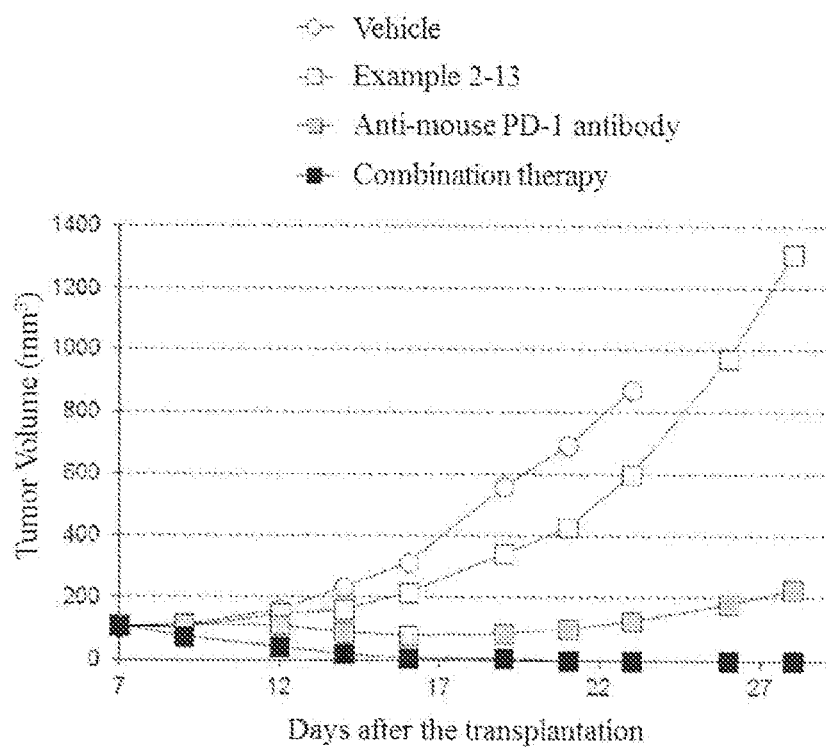
[FIG. 2]
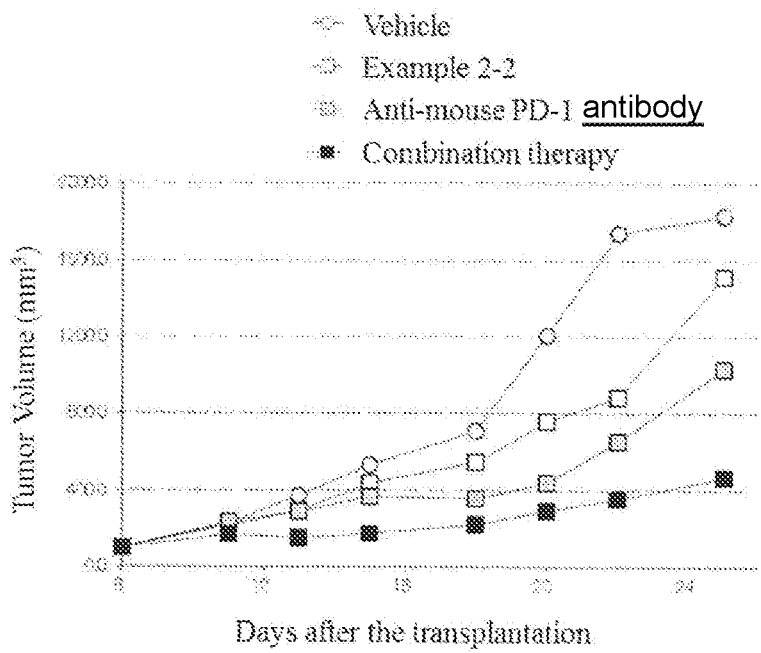

[FIG. 3]
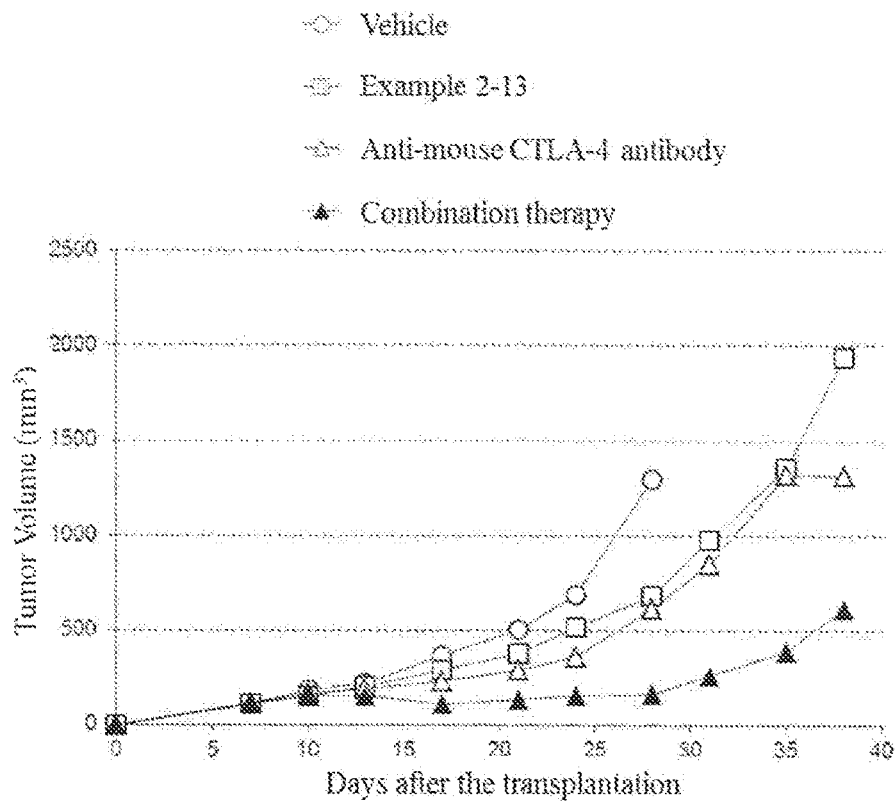
[FIG. 4]
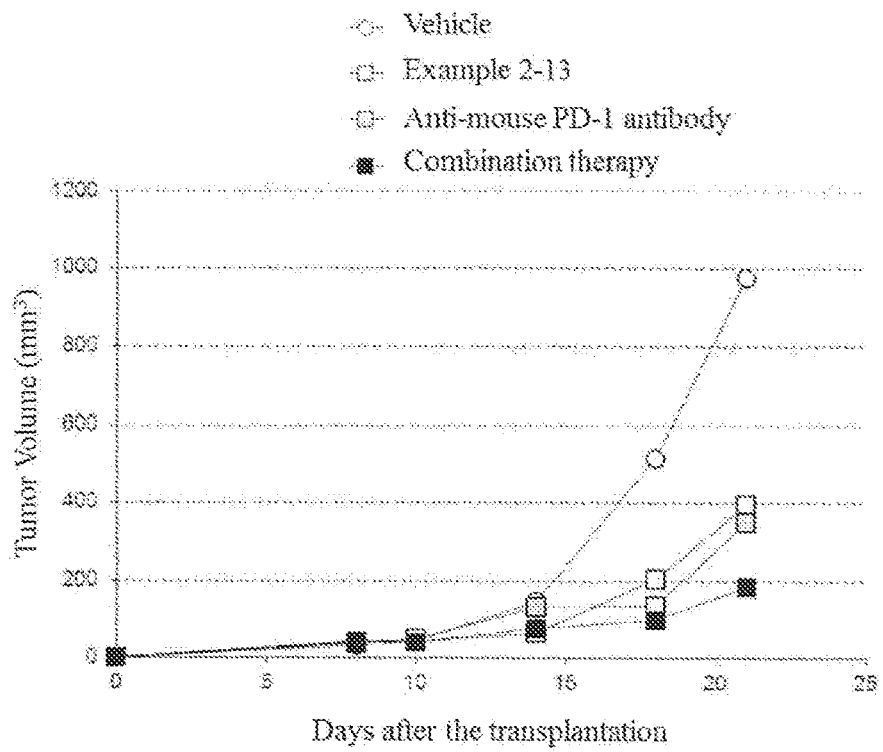

[FIG. 5]
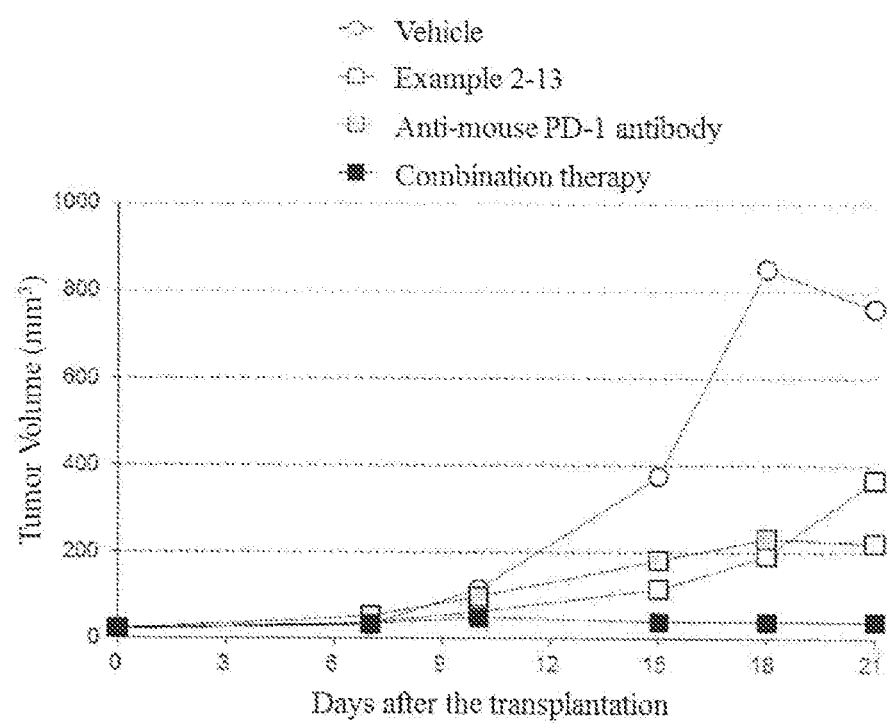

SEQUENCE LISTING

<160> NUMBER OF SEQ ID NOS: 8

<210> SEQ ID NO 1
<211> LENGTH: 113
<212> TYPE: PRT
<213> ORGANISM: Homo sapiens

<400> SEQUENCE: 1

Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser

<210> SEQ ID NO 2
<211> LENGTH: 107
<212> TYPE: PRT
<213> ORGANISM: Homo sapiens

<400> SEQUENCE: 2

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105

<210> SEQ ID NO 3
<211> LENGTH: 5
<212> TYPE: PRT
<213> ORGANISM: Homo sapiens

<400> SEQUENCE: 3

Asn Ser Gly Met His
1               5

<210> SEQ ID NO 4
<211> LENGTH: 17
<212> TYPE: PRT
<213> ORGANISM: Homo sapiens

```
<400> SEQUENCE: 4

Val Ile Trp Tyr Asp Gly Ser Lys Arg Tyr Tyr Ala Asp Ser Val Lys
1               5                   10                  15

Gly

<210> SEQ ID NO 5
<211> LENGTH: 4
<212> TYPE: PRT
<213> ORGANISM: Homo sapiens

<400> SEQUENCE: 5

Asn Asp Asp Tyr
1

<210> SEQ ID NO 6
<211> LENGTH: 11
<212> TYPE: PRT
<213> ORGANISM: Homo sapiens

<400> SEQUENCE: 6

Arg Ala Ser Gln Ser Val Ser Ser Tyr Leu Ala
1               5                   10

<210> SEQ ID NO 7
<211> LENGTH: 7
<212> TYPE: PRT
<213> ORGANISM: Homo sapiens

<400> SEQUENCE: 7

Asp Ala Ser Asn Arg Ala Thr
1               5

<210> SEQ ID NO 8
<211> LENGTH: 9
<212> TYPE: PRT
<213> ORGANISM: Homo sapiens

<400> SEQUENCE: 8

Gln Gln Ser Ser Asn Trp Pro Arg Thr
1               5
```

COMBINATION COMPRISING EP4 ANTAGONIST AND IMMUNE CHECKPOINT INHIBITOR

TECHNICAL FIELD

The present invention relates to a medicament comprising a combination of a compound represented by formula (I)

[Chem. 1]

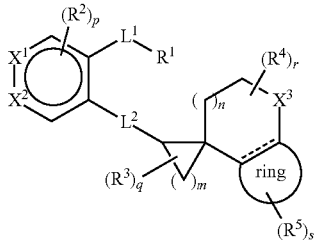

(I)

(in the formula, all the symbols have the same meanings as those described below), a salt thereof, a solvate thereof, an N-oxide thereof, or a prodrug of these and an immune checkpoint inhibitor.

BACKGROUND ART

The prostaglandin $E_2$ ($PGE_2$), a known metabolite of the arachidonic acid cascade, is known to have cytoprotective effect, effect of uterine contraction, effect of lowering the threshold of pain, effect of promoting peristalsis in the digestive tract, arousal effect, effect of inhibiting stomach acid secretion, hypotensive effect, diuretic effect, and the like.

Recent studies have found that there are subtypes of $PGE_2$ receptors with different roles. To date, four broad subtypes are known, and these are called $EP_1$, $EP_2$, $EP_3$, and $EP_4$ (Non-Patent Document 1).

In these subtypes, the $EP_4$ receptor is thought to be involved in inhibition of MCP-1 production from macrophages, inhibition of TNF-α, IL-2, and IFN-γ production from lymphocytes, anti-inflammation by enhanced IL-10 production, vasodilatation, angiogenesis, inhibition of elastic fiber formation, and regulation of MMP-9 expression. Other possible involvement of the $EP_4$ receptor includes immune control in cancer via myeloid derived suppressor cells, regulatory T cells, and natural killer cells.

It is therefore thought that compounds that strongly bind to the $EP_4$ receptor and show antagonistic activity are useful for the treatment of diseases caused by $EP_4$ receptor activation, including, for example, a bone disease, a cancer, a systemic granulomatous disease, an immune disease, allergy, atopy, asthma, alveolar pyorrhea, gingivitis, periodontitis, Alzheimer's, Kawasaki disease, burn, multiple organ failure, chronic headache, pain, vasculitis, venous incompetence, varicose veins, aneurysm, aortic aneurysm, anal fistula, diabetes insipidus, stress, endometriosis, uterine adenomyosis, patent ductus arteriosus in neonates, and cholelithiasis (Non-Patent Documents 2-7).

Patent Document 1 describes that a compound represented by the following formula (A) is used as a compound used for the treatment of diseases involving prostaglandin E receptors, for example, such as pain, inflammation, and cancer.

The formula (A) is as follows:

[Chem. 2]

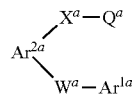

(A)

(in the formula, $Ar^{1a}$ is an aryl or a heteroaryl group optionally substituted with $R^{1a}$ or $R^{3a}$ wherein $R^{1a}$ is CN, $NO_2$, $CON(R^{5a})_2$, or the like; $W^a$ represents a three- to six-membered linking group containing 0 to 2 heteroatoms selected from O, N, and S, wherein the linking group optionally contains CO, $S(O)_{na}$, C=C, or an acetylene group; $Ar^{2a}$ is an aryl or a heteroaryl group optionally substituted with $R^{3a}$, wherein $R^{3a}$ is halogen, CN, or the like; $X^a$ is a linker attached to $Ar^{2a}$ at the position ortho to the bonding site for $W^a$; and $Q^a$ is COOH or the like (these are only a part of the definitions of the groups.))

Patent Document 2 describes that a compound of the following formula (B) binds to the $PGE_2$ receptor, particularly $EP_3$ and/or $EP_4$, and has antagonistic activity and that the compound is thus useful for the prevention and/or treatment of diseases such as pain, and cancer.

The formula (B) is as follows:

[Chem. 3]

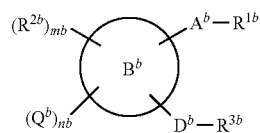

(B)

(in the formula, $R^{1b}$ represents —COOH or the like; $A^b$ represents (i) a single bond, (ii) C1-6 alkylene, (iii) C2-6 alkenylene, (iv) C2-6 alkynylene, or the like; the ring $B^b$ represents a C3-12 monocyclic or bicyclic carbon ring or a three- to twelve-membered monocyclic or bicyclic heterocyclic ring; $R^{2b}$ represents nitro, cyano, or the like; $Q^b$ represents C2-6 alkenyl, C2-6 alkynyl, C1-6 alkyl substituted with 1 to 3 halogen atoms, cyano, nitro, or the like; $D^b$ is a one- or two-membered linking chain of atoms selected from a carbon atom, a nitrogen atom, an oxygen atom, and a sulfur atom, wherein the linking chain may contain a double bond or a triple bond and may be substituted with one to four $R^{40b}$, wherein $R^{40b}$ represents an oxo, halogen, or the like; and $R^{3b}$ represents (1) C1-6 alkyl or (2) a C3-15 monocyclic, bicyclic, or tricyclic carbon ring that is substituted with one to five $R^{42b}$ or that is unsubstituted or a three- to fifteen-membered monocyclic, bicyclic, or tricyclic heterocyclic ring, wherein $R^{42b}$ represents C1-6 alkyl, C1-6 alkoxy, halogen, cyano, —$NR^{46b}COR^{47b}$, or $Cyc10^b$ (these are only a part of the definitions of the groups.))

Patent Document 3 describes that a compound represented by the following formula (C) is used as a compound used for the treatment of diseases involving prostaglandin E receptors, for example, such as pain, inflammation, and cancer.

The formula (C) is as follows:

[Chem. 4]

$$R^{1c}R^{2c}R^{3c}-HET^c\underset{X^c-B^c}{\overset{A^c}{\diagdown}}\overset{O}{\underset{Z^c}{\diagup}}\quad (C)$$

(in the formula, $HET^e$ represents a five- to twelve-membered monocyclic or bicyclic aromatic ring system having 0 to 3 heteroatoms selected from O, $S(O)_{ne}$, and $N(O)_{mc}$, wherein me is 0 or 1, and nc is 0, 1, or 2; $A^c$ is one- or two-atom moiety and is selected from the group consisting of —$W^c$—, —C(O)—, and the like, wherein $W^c$ is O, $S(O)_{nc}$, or $NR^{17C}$; $X^c$ represents a five- to ten-membered monocyclic or bicyclic aryl or heteroaryl group having 1 to 3 heteroatoms selected from O, $S(O)_{nc}$, and $N(O)_{mc}$, $Y^c$ represents O, $S(O)_{nc}$, $NR^{17c}$, a bond, or the like; $B^c$ is —$(C(R^{18c})_2)_{pc}$—$Y^c$—$(C(R^{18c})_2)_{qc}$—, wherein pc and qc are independently 0 to 3; $Z^c$ is OH or the like; and $R^{1c}$, $R^{2c}$, and $R^{3c}$ independently represent halogen, —$CO_2R^{9c}$, —$CON(R^{6c})_2$, or the like (these are only a part of the definitions of the groups.))

None of Patent Documents 1 to 3 and Non-Patent Documents 1 to 7 describe or suggest the tricyclic spiro compound used for the present invention.

Various immune checkpoint molecules that prevent the immune response to cancer are in cancer cells or cancer microenvironment. Immune checkpoint inhibitors provide a new therapeutic method which deactivates the immunosuppression mechanism and which activates the immune reaction to cancer. As immune checkpoint inhibitors, an anti-CTLA-4 (cytotoxic T lymphocyte-associated antigen-4) antibody, ipilimumab, anti-PD-1 (programmed cell death-1) antibodies, nivolumab and pembrolizumab, and the like have already been approved in and outside Japan and are used for the treatment of cancer.

CITATION LIST

Patent Literature

Patent Document 1: WO2000/020371
Patent Document 2: WO2003/016254
Patent Document 3: WO1999/047497

Non Patent Literature

Non-Patent Document 1: Journal of Lipid Mediators and Cell Signalling, Vol. 12, p. 379-391, 1995
Non-Patent Document 2: Pharmacological Reviews, Vol. 65, p. 1010-1052, July, 2013
Non-Patent Document 3: 105th Annual Meeting of American Association for Cancer Research (AACR), Abstract: LB-265, Title of Presentation: ONO-AE3-208 inhibits myeloid derived suppressor cells and glioma growth, Date of Presentation: Apr. 8, 2014
Non-Patent Document 4: FEBS Letters, Vol. 364, p. 339-341, 1995
Non-Patent Document 5: Cancer Science, Vol. 105, p. 1142-1151, 2014
Non-Patent Document 6: Cancer Research, Vol. 70, p. 1606-1615, 2010
Non-Patent Document 7: Cancer Research, Vol. 62, p. 28-32, 2002

SUMMARY OF INVENTION

Technical Problem

An object of the present invention is to find an effective method for treating cancer and to provide the method in the form of a drug.

Solution to Problem

The present inventors conducted intensive studies to achieve the object. As a result, the inventors have found that a compound represented by the formula (I) below, a salt thereof, an N-oxide thereof, a solvate thereof, or a prodrug of these (hereinafter, sometimes simply referred to as the compound used for the present invention) acts as an $EP_4$ receptor antagonist and that a combination of the compound used for the present invention and an immune checkpoint inhibitor (hereinafter, sometimes simply referred to as the combination of the present invention) achieves the object of the present invention. The inventors have thus completed the present invention.

That is, the invention relates to the following subject matters.

[1] A medicament comprising a combination of a compound represented by formula (I), a salt thereof, an N-oxide thereof, a solvate thereof, or a prodrug of these and an immune checkpoint inhibitor,

[Chem. 5]

$$\text{(I)}$$

(structure showing a bicyclic ring system with substituents $(R^2)_p$, $(R^3)_q$, $R^1$, $(R^4)_r$, $(R^5)_s$, $X^1$, $X^2$, $X^3$, $L^1$, $L^2$, and "ring")

(wherein $R^1$ represents $COOR^8$, tetrazole, $SO_3H$, $SO_2NH_2$, $SO_2NHR^{8-1}$, $CONHSO_2R^{8-1}$, $SO_2NHCOR^{8-1}$, or hydroxamic acid, wherein $R^8$ represents a hydrogen atom, C1-4 alkyl, or benzyl, and $R^{8-1}$ represents C1-4 alkyl, C1-4 haloalkyl, a C3-10 carbon ring, or a three- to ten-membered heterocyclic ring, wherein the C3-10 carbon ring and the three- to ten-membered heterocyclic ring each may be substituted with C1-4 alkyl, C1-4 haloalkyl, C1-4 alkoxy, —O(C1-4 haloalkyl), C1-4 alkylthio, —S(C1-4 haloalkyl), halogen, or nitrile (here and below, "—CN"), $L^1$ represents C1-5 alkylene, C2-5 alkenylene, or C2-5 alkynylene, $R^2$ represents halogen, C1-4 alkyl, C1-4 alkoxy, C1-4 alkylthio, C2-4 alkenyl, C2-4 alkynyl, —O(C1-4 haloalkyl), —S(C1-4 haloalkyl), —C(O)(C1-4 alkyl), —$SO_2$(C1-4 alkyl), —CONH(C1-4 alkyl), —CON(C1-4 alkyl)$_2$, —NHC(O)(C1-4 alkyl), —N(C1-4 alkyl)C(O)(C1-4 alkyl), —$NHSO_2$(C1-4 alkyl), —N(C1-4 alkyl)$SO_2$(C1-4 alkyl), —$SO_2NH$(C1-4 alkyl), —$SO_2N$(C1-4 alkyl)$_2$, —$NR^{17}R^{17}$, nitro, nitrile, a hydroxyl group, aldehyde (here and below, formyl), or carboxyl, wherein the C1-4 alkyl groups each may be substituted with halogen, and the (C1-4 alkyl)$_2$ in R$^2$ represents two independent C1-4 alkyl groups which may be the same or different, X$^1$ represents CR$^6$ or a nitrogen atom, wherein R$^6$ represents a hydrogen atom or R$^2$, X$^2$ represents CR$^7$ or a nitrogen atom, wherein R$^7$ represents a hydrogen atom, R$^2$, or -L$^3$-R$^9$, wherein L$^3$ represents methylene, an oxygen atom, or a sulfur atom which may be oxidized, and R$^9$ represents a four- to ten-membered heterocyclic ring which may be substituted with a substituent selected from the group consisting of halogen, C1-4 alkyl, and C1-4 haloalkyl, L$^2$ represents —CH$_2$CH$_2$—, —CH=CH—, —CH$_2$O—, —OCH$_2$—, —CH$_2$S—, —SCH$_2$—, —CH$_2$S(O)—, —S(O)CH$_2$—, —CH$_2$SO$_2$—, —SO$_2$CH$_2$—, —CH$_2$NH—, —NHCH$_2$—, —NHCO—, —CONH—, —NHSO$_2$—, or —SO$_2$NH—, R$^3$ represents C1-4 alkyl or halogen, R$^4$ represents halogen, C1-4 alkyl, or C1-4 haloalkyl, X$^3$ represents methylene, an oxygen atom, a sulfur atom which may be oxidized, or NR$^{10}$, wherein R$^{10}$ represents C1-4 alkyl, —C(O)(C1-4 alkyl), —C(O)O(C1-4 alkyl), or —SO$_2$(C1-4 alkyl), wherein the C1-4 alkyl groups each may be substituted with halogen, the ring represents a benzene ring or a five- or six-membered monocyclic aromatic heterocyclic ring,

[Chem. 6]

- - - - - represents a single bond or a double bond,

R$^5$ represents (1) halogen, (2) C1-4 alkyl, (3) carboxyl, (4) nitrile, (5) —CONHR$^{11}$, (6) —C(O)R$^2$, (7) —OR$^{14}$, (8) —S(O)$_t$R$^{15}$, (9) —CH$_2$R$^{16}$, (10) —NR$^{17}$R$^{17}$, (11) —NHCOR$^{11}$, (12) a C4-10 carbon ring, or (13) a four- to ten-membered heterocyclic ring, wherein the C4-10 carbon ring or the four- to ten-membered heterocyclic ring may be substituted with one to three R$^{18}$, wherein, when a plurality of R$^{1s}$ exists, the plurality of R$^{18}$ each independently may be the same or different, R$^{11}$ represents C1-6 alkyl, C3-6 cycloalkyl, phenyl, or a four- to six-membered heterocyclic ring and may be substituted with one to three R$^{13}$, wherein, when a plurality of R$^{13}$ exists, the plurality of R$^{13}$ each independently may be the same or different, and R$^{13}$ represents halogen, C1-6 alkyl, C3-6 cycloalkyl, C1-4 alkoxy, a hydroxyl group, —NR$^{20}$R$^{21}$, benzene, or a four- to six-membered heterocyclic ring, wherein R$^{20}$ and R$^{21}$ each independently represent a hydrogen atom or C1-4 alkyl, R$^{12}$ represents C1-6 alkyl, C3-6 cycloalkyl, benzene, or a four- to six-membered heterocyclic ring, wherein the C3-6 cycloalkyl, the benzene, and the four- to six-membered heterocyclic ring each independently may be substituted with halogen, C1-4 alkyl, or C1-4 alkoxy, R$^{14}$ represents a hydrogen atom, C1-6 alkyl, C3-6 cycloalkyl, benzene, or benzyl, wherein the C1-6 alkyl may be substituted with one to three R$^{19}$, wherein, when a plurality of R$^{19}$ exists, the plurality of R$^{19}$ each independently may be the same or different, and R$^{19}$ represents C1-4 alkoxy, —CONH(C1-4 alkyl), —CON(C1-4 alkyl)$_2$, or a five- or six-membered monocyclic aromatic heterocyclic ring which may be substituted with a substituent selected from the group consisting of C1-4 alkyl and C1-4 haloalkyl, wherein the (C1-4 alkyl)$_2$ in R$^{19}$ represents two independent C1-4 alkyl groups which may be the same or different, R$^{15}$ represents C1-6 alkyl, C3-6 cycloalkyl, benzene, or benzyl, R$^{16}$ represents a hydroxyl group or C1-4 alkoxy, each R$^{17}$ independently represents a hydrogen atom, C1-6 alkyl, or C3-6 cycloalkyl, and R$^{18}$ represents halogen, C1-6 alkyl, C3-6 cycloalkyl, C1-4 alkoxy, oxo, nitrile, a hydroxyl group, hydroxymethyl, 1-methyl-1-hydroxyethyl, (C1-4 alkyl)SO$_2$—, a four- to six-membered heterocyclic ring, (C1-4 alkyl)NH—, or (C1-4 alkyl)$_2$N—, wherein the (C1-4 alkyl)$_2$ in R$^8$ represents two independent C1-4 alkyl groups which may be the same or different, m represents an integer of 1 to 4, n represents an integer of 0 to 4, p represents an integer of 0 to 2, q represents an integer of 0 to 6, r represents an integer of 0 to 6, s represents an integer of 0 to 4, t represents an integer of 0 to 2, and R$^2$, R$^3$, R$^4$, and R$^5$ each independently may be the same or different when p, q, r, and s are each an integer of 2 or more.)

[2] The medicament according to item [1], wherein the compound represented by formula (I) is a compound represented by formula (I-1),

[Chem. 7]

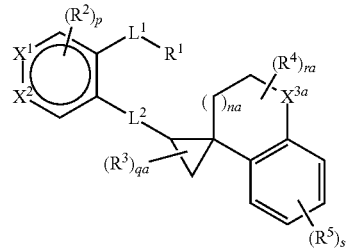

(I-1)

(wherein na represents an integer of 0 or 1, qa represents an integer of 0 to 3, ra represents an integer of 0 to 4, X$^3$a represents methylene or an oxygen atom, and the other symbols have the same meanings as the symbols defined in item [1].)

[3] The medicament according to item [1] or item [2], wherein s is an integer of 1 to 4, and at least one R$^5$ is —CONHR$^{11}$.

[4] The medicament according to any one of item [1] to item [3], wherein L$^2$ is —NHCO— or —CONH—.

[5] The medicament according to any one of item [1] to item [4], wherein the compound represented by formula (I) is a compound represented by formula (I-2),

[Chem. 8]

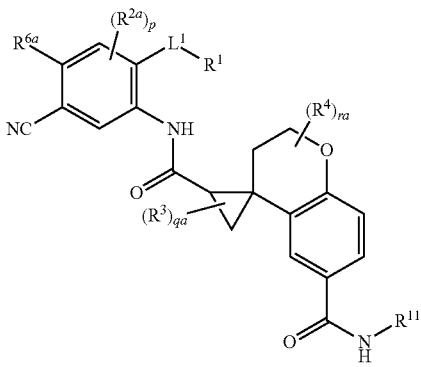

(I-2)

(wherein $R^{2a}$ represents halogen, $R^{6a}$ represents a hydrogen atom or halogen, and the other symbols have the same meanings as the symbols defined in item [1] and item [2].)

[6] The medicament according to item [1], wherein the compound represented by formula (I) is (1) 4-[4-cyano-2-({[(2'R,4S)-6-(methylcarbamoyl)-2,3-dihydrospiro[chromene-4,1'-cyclopropan]-2'-yl]carbonyl}amino)phenyl]butanoic acid,
(2) 4-(4-cyano-2-[({(2'R,4S)-6-[(cyclopropylmethyl)carbamoyl]-2,3-dihydrospiro[chromene-4,1'-cyclopropan]-2'-yl}carbonyl)amino]phenyl]butanoic acid,
(3) 4-(4-cyano-2-[({(2'R,4S)-6-[(2-methoxyethyl)carbamoyl]-2,3-dihydrospiro[chromene-4,1'-cyclopropan]-2'-yl}carbonyl)amino]phenyl}butanoic acid,
(4) 4-{4-cyano-2-[({(2'R,4S)-6-[(2-methyl-2-propanyl)carbamoyl]-2,3-dihydrospiro[chromene-4,1'-cyclopropan]-2'-yl}carbonyl)amino]phenyl}butanoic acid,
(5) 4-[4-cyano-2-({[(2'R,4S)-6-{[(2S)-1-methoxy-2-propanyl]carbamoyl}-2,3-dihydrospiro[chromene-4,1'-cyclopropan]-2'-yl]carbonyl}amino)phenyl]butanoic acid,
(6) 4-{4-cyano-2-[({(2'R,4S)-6-[(1-methyl-1H-pyrazol-3-yl)carbamoyl]-2,3-dihydrospiro[chromene-4,1'-cyclopropan]-2'-yl}carbonyl)amino]phenyl}butanoic acid,
(7) 4-[4-cyano-2-({[(2'R,4S)-6-(cyclopropylcarbamoyl)-2,3-dihydrospiro[chromene-4,1'-cyclopropan]-2'-yl]carbonyl}amino)phenyl]butanoic acid,
(8) 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid,
(9) 4-[4-cyano-2-({[(2'R,4S)-6-(cyclopentylcarbamoyl)-2,3-dihydrospiro[chromene-4,1'-cyclopropan]-2'-yl]carbonyl}amino)phenyl]butanoic acid,
(10) 4-{2-[({(2'R,4S)-6-[(2S)-2-butanylcarbamoyl]-2,3-dihydrospiro[chromene-4,1'-cyclopropan]-2'-yl}carbonyl)amino]-4-cyanophenyl}butanoic acid,
(11) 4-{4-cyano-2-[({(2'R,4S)-6-[(trans-4-hydroxycyclohexyl)carbamoyl]-2,3-dihydrospiro[chromene-4,1'-cyclopropan]-2'-yl}carbonyl)amino]phenyl}butanoic acid,
(12) 4-{4-cyano-2-[({(2'R,4S)-6-[(cis-4-hydroxycyclohexyl)carbamoyl]-2,3-dihydrospiro[chromene-4,1'-cyclopropan]-2'-yl}carbonyl)amino]phenyl}butanoic acid,
(13) 4-[4-cyano-2-({[(2'R,4S)-6-(2-pyridinylcarbamoyl)-2,3-dihydrospiro[chromene-4,1'-cyclopropan]-2'-yl]carbonyl}amino)phenyl]butanoic acid,
(14) 4-[4-cyano-2-(({[(2'R,4S)-6-(3-pyridazinylcarbamoyl)-2,3-dihydrospiro[chromene-4,1'-cyclopropan]-2'-yl]carbonyl}amino)phenyl]butanoic acid,
(15) 4-[4-cyano-2-({[(2'R,4S)-6-(cyclobutylcarbamoyl)-2,3-dihydrospiro[chromene-4,1'-cyclopropan]-2'-yl]carbonyl}amino)phenyl]butanoic acid,
(16) 4-[4-cyano-2-(([(2'R,4S)-6-{[1-(2-methyl-2-propanyl)-1H-pyrazol-4-yl]carbamoyl}-2,3-dihydrospiro[chromene-4,1'-cyclopropan]-2'-yl]carbamoyl}amino)phenyl]butanoic acid,
(17) 4-[4-cyano-2-({[(2'R,4S)-6-(tetrahydro-2H-pyran-4-ylcarbamoyl)-2,3-dihydrospiro[chromene-4,1'-cyclopropan]-2'-yl]carbonyl}amino)phenyl]butanoic acid,
(18) 4-[4-cyano-2-({[(2'R,4S)-6-(propylcarbamoyl)-2,3-dihydrospiro[chromene-4,1'-cyclopropan]-2'-yl]carbonyl}amino)phenyl]butanoic acid,
(19) 4-{4-cyano-2-[({(2'R,4S)-6-[(2-ethoxyethyl)carbamoyl]-2,3-dihydrospiro[chromene-4,1'-cyclopropan]-2'-yl}carbonyl)amino]phenyl}butanoic acid,
(20) 4-[4-cyano-2-(([(2'R,4S)-6-(ethylcarbamoyl)-2,3-dihydrospiro[chromene-4,1'-cyclopropan]-2'-yl]carbonyl}amino)phenyl]butanoic acid,
(21) 4-[4-cyano-2-({[(1R,2R)-6'-(methylcarbamoyl)-2',3'-dihydrospiro[cyclopropane-1,1'-inden]-2-yl]carbonyl}amino)phenyl]butanoic acid,
(22) 4-{4-cyano-2-[({(1R,2R)-6'-[(2-methoxyethyl)carbamoyl]-2',3'-dihydrospiro[cyclopropane-1,1'-inden]-2-yl}carbonyl)amino]phenyl}butanoic acid,
(23) 4-{4-cyano-2-[({(1R,2R)-6'-[(1-methyl-1H-pyrazol-4-yl)carbamoyl]-2',3'-dihydrospiro[cyclopropane-1,1'-inden]-2-yl}carbonyl)amino]phenyl}butanoic acid,
(24) 4-[4-cyano-2-({[(2'R,4S)-7-fluoro-6-(methylcarbamoyl)-2,3-dihydrospiro[chromene-4,1'-cyclopropan]-2'-yl]carbonyl}amino)phenyl]butanoic acid,
(25) 4-{4-cyano-2-[({(2'R,4S)-7-fluoro-6-[(2-methoxyethyl)carbamoyl]-2,3-dihydrospiro[chromene-4,1'-cyclopropan]-2'-yl}carbonyl)amino]phenyl}butanoic acid,
(26) 4-[4-cyano-2-({[(2'R,4S)-7-fluoro-6-(isopropylcarbamoyl)-2,3-dihydrospiro[chromene-4,1'-cyclopropan]-2'-yl]carbonyl}amino)phenyl]butanoic acid,
(27) 4-[4-cyano-2-({[(2'R,4S)-7-(methylcarbamoyl)-2,3-dihydrospiro[chromene-4,1'-cyclopropan]-2'-yl]carbonyl}amino)phenyl]butanoic acid,
(28) 4-{4-cyano-2-[({(2'R,4S)-7-[(2-methoxyethyl)carbamoyl]-2,3-dihydrospiro[chromene-4,1'-cyclopropan]-2'-yl}carbonyl)amino]phenyl}butanoic acid,
(29) 4-[4-cyano-2-({[(2'R,4S)-7-methoxy-6-(methylcarbamoyl)-2,3-dihydrospiro[chromene-4,1'-cyclopropan]-2'-yl]carbonyl}amino)phenyl]butanoic acid,
(30) 4-{4-cyano-2-[({(2'R,4S)-7-methoxy-6-[(2-methoxyethyl)carbamoyl]-2,3-dihydrospiro[chromene-4,1'-cyclopropan]-2'-yl}carbonyl)amino]phenyl}butanoic acid,
(31) 4-[4-cyano-2-({[(2'R,3S)-5-(methylcarbamoyl)-2H-spiro[1-benzofuran-3,1'-cyclopropan]-2'-yl]carbonyl}amino)phenyl]butanoic acid,
(32) 4-{4-cyano-2-[({(2'R,3 S)-5-[(2-methoxyethyl)carbamoyl]-2H-spiro[1-benzofuran-3,1'-cyclopropan]-2'-yl}carbonyl)amino]phenyl}butanoic acid,
(33) 4-[4-cyano-2-({[(1S,2R)-6'-[(2-methoxyethyl)carbamoyl]-3',3'-dimethyl-2',3'-dihydrospiro[cyclopropane-1,1'-inden]-2-yl]carbonyl}amino)phenyl]butanoic acid, or
(34) 4-[4-cyano-2-({[(1S,2R)-3',3'-dimethyl-6'-(methylcarbamoyl)-2',3'-dihydrospiro[cyclopropane-1,1'-inden]-2-yl]carbonyl}amino)phenyl]butanoic acid.

[7] The medicament according to item [1] or item [2], wherein s is an integer of 1 to 4, and at least one $R^5$ is a C4-10 carbon ring which may be substituted with one to three $R^{18}$ or a four- to ten-membered heterocyclic ring which may be substituted with one to three $R^{18}$, wherein, when a plurality of $R^{18}$ exists, the plurality of $R^{18}$ each independently may be the same or different.

[8] The medicament according to item [7], wherein $L^2$ is —NHCO— or —CONH—.

[9] The medicament according to any one of item [1], item [2], item [7], and item [8], wherein the compound represented by formula (I) is a compound represented by formula (I-3),

[Chem. 9]

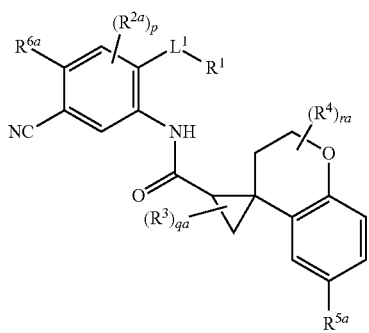

(I-3)

(wherein $R^{5a}$ is a C4-10 carbon ring which may be substituted with one to three $R^{18}$ or a four- to ten-membered heterocyclic ring which may be substituted with one to three $R^{18}$, wherein, when a plurality of $R^{18}$ exists, the plurality of $R^{18}$ each independently may be the same or different, and the other symbols have the same meanings as the symbols defined in item [1], item [2], and item [5].)

[10] The medicament according to item [1], wherein the compound represented by formula (I) is (1) 4-[4-cyano-2-({[(2'R,4S)-6-(5-methyl-1,3,4-oxadiazol-2-yl)-2,3-dihydrospiro[chromene-4,1'-cyclopropan]-2'-yl]carbonyl}amino)phenyl]butanoic acid, (2) 4-[4-cyano-2-({[(2'R,4S)-6-(5-cyclopropyl-1,3,4-oxadiazol-2-yl)-2,3-dihydrospiro[chromene-4,1'-cyclopropan]-2'-yl]carbonyl}amino)phenyl]butanoic acid, (3) 4-[4-cyano-2-({[(2'R,4S)-6-(3-methyl-1,2,4-oxadiazol-5-yl)-2,3-dihydrospiro[chromene-4,1'-cyclopropan]-2'-yl]carbonyl}amino)phenyl]butanoic acid, (4) 4-[4-cyano-2-({[(2'R,4S)-6-(3-pyridinyl)-2,3-dihydrospiro[chromene-4,1'-cyclopropan]-2'-yl]carbonyl}amino)phenyl]butanoic acid, (5) 4-[4-cyano-2-({[(2'R,4S)-6-(1H-pyrazol-1-yl)-2,3-dihydrospiro[chromene-4,1'-cyclopropan]-2'-yl]carbonyl}amino)phenyl]butanoic acid, (6) 4-[4-cyano-2-({[(2'R,4S)-6-(1H-pyrazol-5-yl)-2,3-dihydrospiro[chromene-4,1'-cyclopropan]-2'-yl]carbonyl}amino)phenyl]butanoic acid, (7) 4-[4-cyano-2-({[(2'R,4S)-6-(4-pyridazinyl)-2,3-dihydrospiro[chromene-4,1'-cyclopropan]-2'-yl]carbonyl}amino)phenyl]butanoic acid, (8) 4-[4-cyano-2-({[(2'R,4S)-6-(2-oxo-1-pyrrolidinyl)-2,3-dihydrospiro[chromene-4,1'-cyclopropan]-2'-yl]carbonyl}amino)phenyl]butanoic acid, (9) 4-[4-cyano-2-({[(2'R,4S)-6-(6-methoxy-3-pyridinyl)-2,3-dihydrospiro[chromene-4,1'-cyclopropan]-2'-yl]carbonyl}amino)phenyl]butanoic acid,

(10) 4-{4-cyano-2-[({(2'R,4S)-6-[6-(1H-pyrazol-1-yl)-3-pyridinyl]-2,3-dihydrospiro[chromene-4,1'-cyclopropan]-2'-yl}carbonyl)amino]phenyl}butanoic acid,

(11) 4-{4-cyano-2-[({(2'R,4S)-6-[6-(dimethylamino)-3-pyridinyl]-2,3-dihydrospiro[chromene-4,1'-cyclopropan]-2'-yl}carbonyl)amino]phenyl}butanoic acid,

(12) 4-[4-cyano-2-({[(2'R,4S)-6-(6-methyl-3-pyridinyl)-2,3-dihydrospiro[chromene-4,1'-cyclopropan]-2'-yl]carbonyl}amino)phenyl]butanoic acid,

(13) 4-{4-cyano-2-[({(2'R,4S)-6-[6-(methylamino)-3-pyridinyl]-2,3-dihydrospiro[chromene-4,1'-cyclopropan]-2'-yl}carbonyl)amino]phenyl}butanoic acid,

(14) 4-[4-cyano-2-({[(2'R,4S)-6-(2-pyridinyl)-2,3-dihydrospiro[chromene-4,1'-cyclopropan]-2'-yl]carbonyl}amino)phenyl]butanoic acid,

(15) 4-[4-cyano-2-({[(2'R,4S)-6-(1,3-thiazol-2-yl)-2,3-dihydrospiro[chromene-4,1'-cyclopropan]-2'-yl]carbonyl}amino)phenyl]butanoic acid,

(16) 4-[4-cyano-2-({[(2'R,4S)-6-(1,3-oxazol-2-yl)-2,3-dihydrospiro[chromene-4,1'-cyclopropan]-2'-yl]carbonyl}amino)phenyl]butanoic acid,

(17) 4-[4-cyano-2-({[(2'R,4S)-6-(1-methyl-1H-1,2,3-triazol-4-yl)-2,3-dihydrospiro[chromene-4,1'-cyclopropan]-2'-yl]carbonyl}amino)phenyl]butanoic acid,

(18) 4-[4-cyano-2-({[(2'R,4S)-6-(3-pyridazinyl)-2,3-dihydrospiro[chromene-4,1'-cyclopropan]-2'-yl]carbonyl}amino)phenyl]butanoic acid,

(19) 4-[4-cyano-2-({[(2'R,3 S)-5-(3-pyridinyl)-2H-spiro[1-benzofuran-3,1'-cyclopropan]-2'-yl]carbonyl}amino)phenyl]butanoic acid, or

(20) 4-[4-cyano-2-({[(1 S,2R)-3',3'-dimethyl-6'-(3-pyridinyl)-2',3'-dihydrospiro[cyclopropane-1,1'-inden]-2-yl]carbonyl}amino)phenyl]butanoic acid.

[11] A medicament comprising a combination of 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, an N-oxide thereof, a solvate thereof, or a prodrug of these and an immune checkpoint inhibitor.

[12] A medicament comprising a combination of 4-(4-cyano-2-[({(2'R,4S)-6-[(2-methoxyethyl)carbamoyl]-2,3-dihydrospiro[chromene-4,1'-cyclopropan]-2'-yl}carbonyl)amino]phenyl}butanoic acid, a salt thereof, an N-oxide thereof, a solvate thereof, or a prodrug of these and an immune checkpoint inhibitor.

[13] The medicament according to any one of item [1] to item [12], wherein the immune checkpoint inhibitor is an inhibitor of an immune checkpoint molecule selected from the group consisting of CTLA-4, PD-1, PD-L1, PD-L2, LAG-3, TIM3, BTLA, B7H3, B7H4, CD160, CD39, CD73, A2aR, KIR, VISTA, IDO1, Arginase I, TIGIT, and CD115.

[14] The medicament according to any one of item [1] to item [13], wherein the immune checkpoint inhibitor is an anti-PD-1 antibody.

[15] The medicament according to any one of item [1] to item [13], wherein the immune checkpoint inhibitor is an anti-CTLA-4 antibody.

[16] The medicament according to any one of item [1] to item [15] for the treatment of cancer.

[17] The medicament according to item [16], wherein the cancer is any of leukemia, malignant lymphoma, multiple myeloma, myelodysplastic syndrome, head and neck cancer, esophageal cancer, esophageal adenocarcinoma, stomach cancer, duodenal cancer, colorectal cancer, colon cancer, rectal cancer, liver cancer, gallbladder/bile duct cancer, biliary tract cancer, pancreatic cancer, thyroid cancer, lung cancer, breast cancer, ovarian cancer, cervical cancer, corpus uteri cancer, endometrial cancer, vaginal cancer, vulvar cancer, renal cancer, renal pelvis/ureter cancer, urothelial cancer, penile cancer, prostate cancer, testicular tumor, osteosarcoma/soft tissue sarcoma, malignant bone tumor, skin cancer, thymoma, mesothelioma, and cancer of unknown primary.

[18] A therapeutic agent against cancer comprising a combination of the compound represented by formula (I) according to item [1], a salt thereof, a solvate thereof, an N-oxide thereof, or a prodrug of these and an immune checkpoint inhibitor.

[19] A method for treating cancer characterized by administering effective amounts of the compound represented by formula (I) according to item [1], a salt thereof, a solvate thereof, an N-oxide thereof, or a prodrug of these and an immune checkpoint inhibitor to a mammal (preferably a human patient).

[20] A combination of the compound represented by formula (I) according to item [1], a salt thereof, a solvate thereof, an N-oxide thereof, or a prodrug of these and an immune checkpoint inhibitor for the treatment of cancer.

[21] A combination of the compound represented by formula (I) according to item [1], a salt thereof, a solvate thereof, an N-oxide thereof, or a prodrug of these and an immune checkpoint inhibitor for the production of a therapeutic agent against cancer.

[22] A medicament for the treatment of cancer characterized by administering a combination of the compound represented by formula (I) according to item [1], a salt thereof, an N-oxide thereof, a solvate thereof, or a prodrug of these and an immune checkpoint inhibitor.

[23] A medicament for the treatment of cancer characterized by administering a combination of 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, an N-oxide thereof, a solvate thereof, or a prodrug of these and an immune checkpoint inhibitor.

[24] The medicament according to item [23], wherein the immune checkpoint inhibitor is an inhibitor of an immune checkpoint molecule selected from the group consisting of CTLA-4, PD-1, PD-L1, PD-L2, LAG-3, TIM3, BTLA, B7H3, B7H4, CD160, CD39, CD73, A2aR, KIR, VISTA, IDO1, Arginase I, TIGIT, and CD115.

[25] The medicament according to item [23] or item [24], wherein the immune checkpoint inhibitor is an anti-PD-1 antibody.

[26] The medicament according to item [23] or item [24], wherein the immune checkpoint inhibitor is an anti-CTLA-4 antibody.

[27] The medicament according to any one of items [23] to [26], wherein the cancer is stomach cancer, colorectal cancer, lung cancer, renal cancer, or malignant melanoma.

[28] A therapeutic agent against cancer containing the compound represented by formula (I) according to item [1], a salt thereof, an N-oxide thereof, a solvate thereof, or a prodrug of these as an active ingredient characterized by being administered in combination with an immune checkpoint inhibitor.

[29] A therapeutic agent against cancer containing 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, an N-oxide thereof, a solvate thereof, or a prodrug of these as an active ingredient characterized by being administered in combination with an immune checkpoint inhibitor.

[30] The agent according to item [29], wherein the immune checkpoint inhibitor is an inhibitor of an immune checkpoint molecule selected from the group consisting of CTLA-4, PD-1, PD-L1, PD-L2, LAG-3, TIM3, BTLA, B7H3, B7H4, CD160, CD39, CD73, A2aR, KIR, VISTA, IDO1, Arginase I, TIGIT, and CD115.

[31] The agent according to item [29] or item [30], wherein the immune checkpoint inhibitor is an anti-PD-1 antibody.

[32] The agent according to item [29] or item [30], wherein the immune checkpoint inhibitor is an anti-CTLA-4 antibody.

[33] The agent according to any one of items [29] to [32], wherein the cancer is stomach cancer, colorectal cancer, lung cancer, renal cancer, or malignant melanoma.

[34] A therapeutic agent against cancer containing an immune checkpoint inhibitor as an active ingredient characterized by being administered in combination with the compound represented by formula (I) according to item [1], a salt thereof, an N-oxide thereof, a solvate thereof, or a prodrug of these.

[35] A therapeutic agent against cancer containing an immune checkpoint inhibitor as an active ingredient characterized by being administered in combination with 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, an N-oxide thereof, a solvate thereof, or a prodrug of these.

[36] The agent according to item [35], wherein the immune checkpoint inhibitor is an inhibitor of an immune checkpoint molecule selected from the group consisting of CTLA-4, PD-1, PD-L, PD-L2, LAG-3, TIM3, BTLA, B7H3, B7H4, CD160, CD39, CD73, A2aR, KIR, VISTA, IDO1, Arginase I, TIGIT, and CD115.

[37] The agent according to item [35] or item [36], wherein the immune checkpoint inhibitor is an anti-PD-1 antibody.

[38] The agent according to item [35] or item [36], wherein the immune checkpoint inhibitor is an anti-CTLA-4 antibody.

[39] The agent according to any one of items [35] to [38], wherein the cancer is stomach cancer, colorectal cancer, lung cancer, renal cancer, or malignant melanoma.

[40] 4-[4-Cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, an N-oxide thereof, a solvate thereof, or a prodrug of these for the treatment of cancer characterized by being administered in combination with an immune checkpoint inhibitor.

[41] A method for treating cancer characterized by administering an effective amount of 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, an N-oxide thereof, a solvate thereof, or a prodrug of these in combination with an immune checkpoint inhibitor to a mammal (preferably a human patient) in need of the treatment of cancer.

[42] A therapeutic agent against cancer characterized by administering a combination of 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, an N-oxide thereof, a solvate thereof, or a prodrug of these and an immune checkpoint inhibitor.

[43] A therapeutic agent against cancer containing 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, an N-oxide thereof, a solvate thereof, or a prodrug of these as an active ingredient characterized by being administered to a patient to which an immune checkpoint inhibitor is administered.

[44] A therapeutic agent against cancer containing an immune checkpoint inhibitor as an active ingredient characterized by being administered to a patient to which 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, an N-oxide thereof, a solvate thereof, or a prodrug of these is administered.

[45] Use of a combination of 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, an N-oxide thereof, a solvate thereof, or a prodrug of these and an immune checkpoint inhibitor for the production of a medicament for the treatment of cancer.

[46] Use of 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, an N-oxide thereof, a solvate thereof, or a prodrug of these for the production of a therapeutic agent against cancer characterized by being administered in combination with an immune checkpoint inhibitor.

[47] Use of an immune checkpoint inhibitor for the production of a therapeutic agent against cancer characterized by being administered in combination with 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, an N-oxide thereof, a solvate thereof, or a prodrug of these.

[48] A method for treating cancer characterized by administering an effective dose of 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, an N-oxide thereof, a solvate thereof, or a prodrug of these to a patient, wherein the patient further receives treatment with an immune checkpoint inhibitor.

[49] A method for treating cancer characterized by administering an effective dose of an immune checkpoint inhibitor to a patient, wherein the patient further receives treatment with 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, an N-oxide thereof, a solvate thereof, or a prodrug of these.

Advantageous Effects of Invention

The combination of the invention is useful for the treatment of cancer.

BRIEF DESCRIPTION OF DRAWINGS

FIG. 1 shows the effect of the combination therapy with the compound of Example 2-13 and an anti-mouse PD-1 antibody in an allograft model of mouse colorectal cancer cell line MC38. In the figure, the combination therapy indicates the group of the combination therapy with the compound of Example 2-13 and the anti-mouse PD-1 antibody.

FIG. 2 shows the effect of the combination therapy with the compound of Example 2-2 and an anti-mouse PD-1 antibody in an allograft model of mouse colorectal cancer cell line MC38. In the figure, the combination therapy indicates the group of the combination therapy with the compound of Example 2-2 and the anti-mouse PD-1 antibody.

FIG. 3 shows the effect of the combination therapy with the compound of Example 2-13 and an anti-mouse CTLA-4 antibody in an allograft model of mouse colorectal cancer cell line MC38. In the figure, the combination therapy indicates the group of the combination therapy with the compound of Example 2-13 and the anti-mouse CTLA-4 antibody.

FIG. 4 shows the effect of the combination therapy with the compound of Example 2-13 and an anti-mouse PD-1 antibody in an allograft model of mouse fibrosarcoma cell line SaIN. In the figure, the combination therapy indicates the group of the combination therapy with the compound of Example 2-13 and the anti-mouse PD-1 antibody.

FIG. 5 shows the effect of the combination therapy with the compound of Example 2-13 and an anti-mouse PD-1 antibody in an allograft model of mouse colorectal cancer cell line CT26. In the figure, the combination therapy indicates the group of the combination therapy with the compound of Example 2-13 and the anti-mouse PD-1 antibody.

DESCRIPTION OF EMBODIMENTS

The present invention is explained below in detail.

In the present invention, "C1-4 alkyl" is, for example, methyl, ethyl, n-propyl, isopropyl, n-butyl, sec-butyl, tert-butyl, or isobutyl.

In the present invention, "C1-3 alkyl" is, for example, methyl, ethyl, n-propyl, or isopropyl.

In the present invention, "C1-5 alkylene" is, for example, methylene, ethylene, propylene, butylene, or pentylene.

In the present invention, "C2-5 alkenylene" is, for example, ethenylene, 1-propenylene, 2-propenylene, 1-butenylene, 2-butenylene, 3-butenylene, 1-pentenylene, 2-pentenylene, 3-pentenylene, 4-pentenylene, or the like.

In the present invention, "C2-5 alkynylene" is, for example, ethynylene, 1-propynylene, 2-propynylene, 1-butynylene, 2-butynylene, 3-butynylene, 1-pentynylene, 2-pentynylene, 3-pentynylene, 4-pentynylene, or the like.

In the present invention, "halogen" is fluorine, chlorine, bromine, or iodine.

In the present invention, "C1-4 alkoxy" is, for example, methoxy, ethoxy, propoxy, isopropoxy, butoxy, 1-methylpropoxy, tert-butoxy, isobutoxy, or the like.

In the present invention, "C1-4 alkylthio" is, for example, methylthio, ethylthio, propylthio, isopropylthio, butylthio, 1-methylpropylthio, tert-butylthio, isobutylthio, or the like.

In the present invention, "C2-4 alkenyl" is, for example, ethenyl, 1-propenyl, 2-propenyl, 1-butenyl, 2-butenyl, 3-butenyl, or the like.

In the present invention, "C2-4 alkynyl" is, for example, ethynyl, 1-propynyl, 2-propynyl, 1-butynyl, 2-butynyl, 3-butynyl, or the like.

In the present invention, "C1-4 haloalkyl" represents halogen-substituted C1-4 alkyl and is, for example, monofluoromethyl, difluoromethyl, trifluoromethyl, 2-fluoroethyl, 1-fluoroethyl, 2,2-difluoroethyl, 1,2-difluoroethyl, 1,1-difluoroethyl, 2,2,2-trifluoroethyl, 1,2,2-trifluoroethyl, 1,1,2-trifluoroethyl, 1,2,2,2-tetrafluoroethyl, 1,1,2,2-tetrafluoroethyl, pentafluoroethyl, 1,2-dibromo-1,2,2-trifluoroethyl, 1-chloro-1,2,2,2-tetrafluoroethyl, 3-fluoropropyl, 3-chloropropyl, 2-fluoropropyl, 2-chloropropyl, 1-fluoropropyl, 1-chloropropyl, 3,3-difluoropropyl, 2,3-difluoropropyl, 1,3-difluoropropyl, 1,2-difluoropropyl, 2,2-difluoropropyl, 1,1-difluoropropyl, 3,3,3-trifluoropropyl, 2,3,3-trifluoropropyl, 1,3,3-trifluoropropyl, 1,2,2-trifluoropropyl, 1,1,2-trifluoropropyl, 1,1,3-trifluoropropyl, 1,1,2,2-tetrafluoropropyl, 2,2,3,3,3-pentafluoropropyl, 4-fluorobutyl, 4-chlorobutyl, 3-fluorobutyl, 3-chlorobutyl, 2-fluorobutyl, 2-chlorobutyl, 1-fluorobutyl, 1-chlorobutyl, 3,3-difluorobutyl, 2,3-difluorobutyl, 1,3-difluorobutyl, 1,2-difluorobutyl, 2,2-difluorobutyl, 1,1-difluorobutyl, 3,3,3-trifluorobutyl, 2,3,3-trifluorobutyl, 1,3,3-trifluorobutyl, 1,2,2-trifluorobutyl, 1,1,2-trifluorobutyl, 1,1,3-trifluorobutyl, 1,1,2,2-tetrafluorobutyl, 2,2,3,3,3-pentafluorobutyl, or the like.

In the present invention, "sulfur atom that may be oxidized" represents sulfur (S), sulfoxide (S(O)), or sulfone (SO$_2$).

In the present invention, "four- to ten-membered heterocyclic ring" means a four- to ten-membered monocyclic or bicyclic heterocyclic ring containing 1 to 5 heteroatoms selected from an oxygen atom, a nitrogen atom, and a sulfur atom and is, for example, an oxetane, azetidine, pyrrolidine, pyrrole, imidazole, triazole, tetrazole, pyrazole, pyridine, piperidine, piperazine, pyrazine, pyrimidine, pyridazine, azepine, diazepine, furan, pyran, oxepin, thiophene, thiopyran, thiepine, oxazole, isooxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, indazole, quinoline, isoquinoline, quinolizine, purine, phthalazine, pteridin, naphthyridine, quinoxaline, quinazoline, cinnoline, benzooxazole, benzothiazole, benzoimidazole, benzodioxole, benzooxathiol, chromene, benzofurazan, benzothiadiazole, benzotriazole, pyrroline, pyrrolidine, imidazoline, imidazolidine, triazoline, triazolidine, tetrazoline, tetrazolidine, pyrazoline, pyrazolidine, dihydropyridine, tetrahydropyridine, dihydropyrazine, tetrahydropyrazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepin, tetrahydrooxepin, perhydrooxepin, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisooxazole, tetrahydroisooxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, tetrahydrotriazolopyrazine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzooxathiane, dihydrobenzooxazine, dihydrobenzothiazine, pyrazinomorpholine, dihydrobenzooxazole, perhydrobenzooxazole, dihydrobenzothiazole, perhydrobenzothiazole, dihydrobenzoimidazole, perhydrobenzoimidazole, dioxolan, dioxane, dioxaindan, benzodioxane, thiochromane, dihydrobenzodioxine, dihydrobenzoxathiin, chromane, pyrazolopyrimidine, imidazopyridazine, imidazopyridine, imidazopyrimidine, pyrrolopyridine, pyrrolopyrimidine, pyrrolopyridazine, imidazopyrazine, pyrazolopyridine, pyrazolopyrimidine, triazolopyridine, or dihydropyridooxazine ring, or the like.

In the present invention, "three- to ten-membered heterocyclic ring" means a three- to ten-membered monocyclic or bicyclic heterocyclic ring containing 1 to 5 heteroatoms selected from an oxygen atom, a nitrogen atom, and a sulfur atom and is, for example, aziridine, oxirane, thiirane, any of the heterocyclic rings exemplified above for the "four- to ten-membered heterocyclic ring", or the like.

In the present invention, "five- to ten-membered aromatic heterocyclic ring" means a five- to ten-membered monocyclic or bicyclic aromatic heterocyclic ring containing 1 to 4 heteroatoms selected from an oxygen atom, a nitrogen atom, and a sulfur atom and is, for example, a pyrrole, imidazole, triazole, tetrazole, pyrazole, furan, thiophene, oxazole, isooxazole, thiazole, isothiazole, furazan, oxadiazole, thiadiazole, pyridine, pyrazine, pyrimidine, pyridazine, indole, isoindole, benzofuran, isobenzofuran, benzothiophene, isobenzothiophene, indazole, purine, benzooxazole, benzothiazole, benzoimidazole, benzofurazan, benzothiadiazole, benzotriazole, quinoline, isoquinoline, phthalazine, pteridin, naphthyridine, quinoxaline, quinazoline, or cinnoline ring, or the like.

In the present invention, "five- to six-membered monocyclic aromatic heterocyclic ring" is, for example, a pyrrole, imidazole, triazole, tetrazole, pyrazole, pyridine, pyrazine, pyrimidine, pyridazine, furan, thiophene, oxazole, isooxazole, thiazole, isothiazole, furazan, oxadiazole, or thiadiazole ring, or the like.

In the present invention, "C4-10 carbon ring" means a C4 to 10 monocyclic or bicyclic carbon ring and is, for example, a cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, or perhydronaphthalene ring, or the like.

In the present invention, "C3-10 carbon ring" means a C3 to 10 monocyclic or bicyclic carbon ring and is, for example, cyclopropane, any of the carbon rings exemplified above for the "C4-10 carbon ring", or the like.

In the present invention, "C1-6 alkyl" is, for example, methyl, ethyl, n-propyl, isopropyl, n-butyl, sec-butyl, tert-butyl, isobutyl, pentyl, 1-methylbutyl, 2-methylbutyl, 3-methylbutyl, 1,1-dimethylpropyl, 1,2-dimethylpropyl, 2,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 1-methyl-1-ethylpropyl, 2-methyl-2-ethylpropyl, 1-ethylbutyl, 2-ethylbutyl, or the like.

In the present invention, "C3-6 cycloalkyl" is cyclopropyl, cyclobutyl, cyclopentyl, or cyclohexyl.

In the present invention, "four- to six-membered heterocyclic ring" means a four- to six-membered monocyclic heterocyclic ring containing 1 to 4 heteroatoms selected from an oxygen atom, a nitrogen atom, and a sulfur atom and is, for example, an oxetane, azetidine, pyrrolidine, piperidine, pyrazine, pyran, thiopyran, oxazine, oxadiazine, thiazine, thiadiazine, pyrrole, imidazole, triazole, tetrazole, pyrazole, pyridine, pyrimidine, pyridazine, furan, thiophene, oxazole, isooxazole, thiazole, isothiazole, furazan, oxadiazole, or thiadiazole ring, or the like.

In the present invention, $R^1$ is preferably $COOR^8$.

In the present invention, $R^8$ is preferably a hydrogen atom or C1-4 alkyl, more preferably a hydrogen atom.

In the present invention, $R^{8-1}$ is preferably C1-4 alkyl, benzene, or pyridine. The benzene and the pyridine may be substituted with C1-4 alkyl, C1-4 haloalkyl, C1-4 alkoxy, —O(C1-4 haloalkyl), C1-4 alkylthio, —S(C1-4 haloalkyl), halogen, or nitrile.

In the present invention, L is preferably C1-5 alkylene or C2-5 alkenylene, more preferably C1-5 alkylene, particularly preferably propylene.

In the present invention, $R^2$ is preferably fluorine.

In the present invention, $X^1$ is preferably $CR^6$.

In the present invention, $R^6$ is preferably a hydrogen atom or fluorine, more preferably a hydrogen atom.

In the present invention, $X^2$ is preferably $CR^7$.

In the present invention, $R^7$ is preferably fluorine, nitrile, —$CH_2R^9$, or —$OR^9$, more preferably nitrile.

In the present invention, $R^9$ is preferably a four- to ten-membered heterocyclic ring which may be substituted with methyl or trifluoromethyl. The four- to ten-membered heterocyclic ring is preferably a five- to ten-membered aromatic heterocyclic ring, more preferably a five- to ten-membered nitrogen-containing aromatic heterocyclic ring (for example, pyrazole, imidazole, triazole, pyrrolopyridine, pyrrolopyrimidine, pyrrolopyridazine, imidazopyridazine, imidazopyridine, imidazopyrimidine, imidazopyrazine, pyrazolopyridine, pyrazolopyrimidine, or the like).

In the present invention, L2 is preferably —CH=CH—, —NHCO—, —CONH—, —NHSO₂—, or —SO₂NH—, more preferably —NHCO— or —CONH—, particularly preferably —NHCO—.

In the present invention, $R^3$ is preferably fluorine.

In the present invention, $R^4$ is preferably methyl, ethyl, or trifluoromethyl, more preferably methyl.

In the present invention, $X^3$ is preferably methylene or an oxygen atom, more preferably an oxygen atom.

In the present invention, $R^{10}$ is preferably methyl, ethyl, methylcarbonyl, ethylcarbonyl, methylsulfonyl, ethylsulfonyl, or tert-butoxycarbonyl.

In the present invention, the ring is preferably a benzene, thiophene, or pyrazole ring, more preferably a benzene ring.

In the present invention, $R^5$ is preferably —$CONHR^{11}$, fluorine, methoxy, a benzene ring, or a four- to ten-membered heterocyclic ring. The four- to ten-membered heterocyclic ring is preferably an azetidine, pyrrolidine, piperidine, oxazolidine, oxadiazole, triazole, thiophene, furan, pyrazole, thiazole, oxazole, imidazole, pyridine, pyrazine, pyridazine, pyrimidine, pyrazolopyrimidine, pyrrolopyrimidine, pyrazolopyridine, pyrrolopyridine, or dihydropyridooxazine ring.

In the present invention, $R^{11}$ is preferably C1-6 alkyl, C3-6 cycloalkyl, or a pyran, pyrrolidine, piperidine, pyrazole, thiazole, oxazole, isooxazole, pyridine, pyridazine, or pyrimidine ring, more preferably C1-6 alkyl.

In the present invention, $R^{13}$ is preferably halogen, C1-6 alkyl, C3-6 cycloalkyl, C1-4 alkoxy, a hydroxyl group, —$NR^{20}R^{21}$, or a benzene, oxetane, pyridine, pyrazole, or oxazole ring, more preferably fluorine, methyl, ethyl, n-propyl, isopropyl, n-butyl, sec-butyl, tert-butyl, isobutyl, cyclopentyl, cyclobutyl, oxetane, a hydroxyl group, methoxy, ethoxy, propoxy, isopropoxy, dimethylamino, or a benzene, pyridine, pyrazole, or oxazole ring.

In the present invention, $R^{20}$ is preferably a hydrogen atom or methyl.

In the present invention, $R^{21}$ is preferably a hydrogen atom or methyl.

In the present invention, $R^{12}$ is preferably C1-3 alkyl, C3-6 cycloalkyl, benzene, or a four- to six-membered heterocyclic ring. The four- to six-membered heterocyclic ring is preferably an oxetane, azetidine, pyrrolidine, piperidine, pyrazine, pyran, thiopyran, oxazine, oxadiazine, thiazine, thiadiazine, pyrrole, imidazole, triazole, tetrazole, pyrazole, pyridine, pyrazine, pyrimidine, pyridazine, furan, thiophene, oxazole, isooxazole, thiazole, isothiazole, furazan, oxadiazole, or thiadiazole ring. The four- to six-membered heterocyclic ring may be substituted with C1-4 alkoxy.

In the present invention, $R^{14}$ is preferably a hydrogen atom, methyl, ethyl, benzene, or benzyl.

In the present invention, $R^{19}$ is preferably methoxy, —$CONHCH_3$, —$CON(CH_3)_2$, or an oxazole, thiazole, pyrazole, or pyridine ring.

In the present invention, $R^{15}$ is preferably methyl, cyclopropyl, or benzene.

In the present invention, $R^{16}$ is preferably a hydroxyl group.

In the present invention, $R^{17}$ is preferably methyl, ethyl, or cyclopropyl, more preferably methyl.

In the present invention, $R^{18}$ is preferably fluorine, methyl, ethyl, n-propyl, isopropyl, n-butyl, sec-butyl, tert-butyl, isobutyl, cyclopropyl, methoxy, ethoxy, n-propoxy, isopropoxy, oxo, nitrile, a hydroxyl group, hydroxymethyl, 1-methyl-1-hydroxyethyl, methylsulfonyl, pyridine, or dimethylamino.

In the present invention, m is preferably an integer of 1 or 2, more preferably 1.

In the present invention, n is preferably an integer of 0 or 1, more preferably 1.

In the present invention, p is preferably 0.

In the present invention, q is preferably 0.

In the present invention, r is preferably an integer of 0 to 4, more preferably an integer of 0 to 2.

In the present invention, s is preferably an integer of 0 to 2, more preferably 1 or 2.

In the present invention, t is preferably an integer of 0 to 2.

In the present invention, $X^{3a}$ is preferably an oxygen atom.

In the present invention, na is preferably an integer of 0 or 1, more preferably 1.

In the present invention, qa is preferably 0.

In the present invention, ra is preferably an integer of 0 to 2.

In the present invention, formula (I) is preferably a combination of the respective preferred definitions of the ring, $R^1$, $R^2$, $R^3$, $R^4$, $R^5$, $R^6$, $R^7$, $R^8$, $R^{8-1}$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $L^1$, $L^2$, $L^3$, $X^1$, $X^2$, $X^3$, m, n, p, q, r, s, and t.

In the present invention, the compound represented by formula (I) is preferably a compound represented by formula (I-a), a salt thereof, an N-oxide thereof, a solvate thereof, or a prodrug of these.

[Chem. 10]

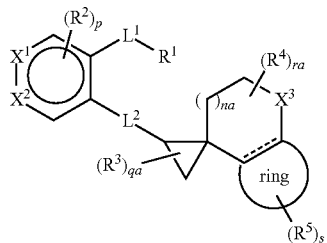

(I-a)

(In the formula, all the symbols have the same meanings as the symbols defined in items [1] and [2] above.) More preferred is a compound represented by formula (I-1), a salt thereof, an N-oxide thereof, a solvate thereof, or a prodrug of these.

[Chem. 11]

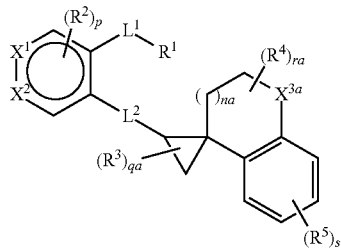

(I-1)

(In the formula, all the symbols have the same meanings as the symbols defined in items [1] and [2] above.)

In the present invention, a more preferred aspect of the compound represented by formula (I) is a compound represented by formula (I-b), a salt thereof, an N-oxide thereof, a solvate thereof, or a prodrug of these.

[Chem. 12]

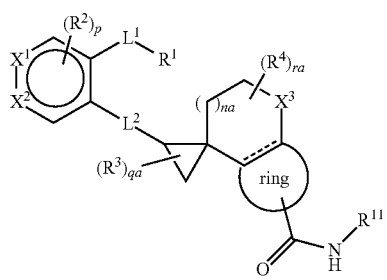

(I-b)

(In the formula, all the symbols have the same meanings as the symbols defined in items [1] and [2] above.) An even more preferred is a compound represented by formula (I-c), a salt thereof, an N-oxide thereof, a solvate thereof, or a prodrug of these.

[Chem. 13]

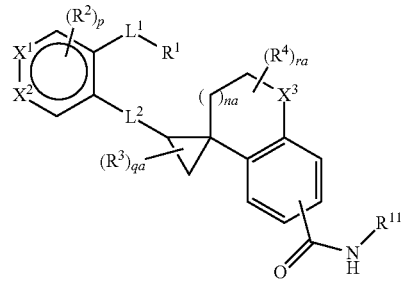

(I-c)

(In the formula, all the symbols have the same meanings as the symbols defined in items [1] and [2] above.) Preferred is a compound represented by formula (I-d), a salt thereof, an N-oxide thereof, a solvate thereof, or a prodrug of these.

[Chem. 14]

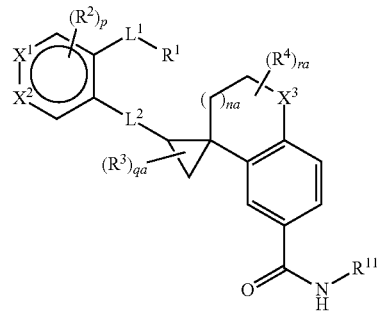

(I-d)

(In the formula, all the symbols have the same meanings as the symbols defined in items [1] and [2] above.) Further preferred is a compound represented by formula (I-e), a salt thereof, an N-oxide thereof, a solvate thereof, or a prodrug of these.

[Chem. 15]

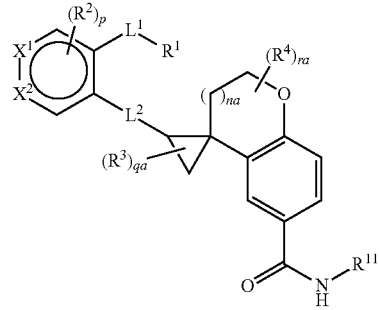

(I-e)

(In the formula, all the symbols have the same meanings as the symbols defined in items [1] and [2] above.) Particularly preferred is a compound represented by formula (I-2), a salt thereof, an N-oxide thereof, a solvate thereof, or a prodrug of these.

[Chem. 16]

(I-2)

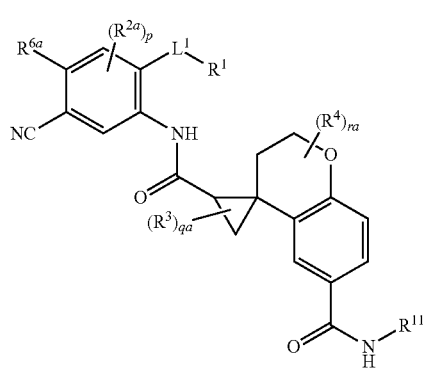

(In the formula, all the symbols have the same meanings as the symbols defined in items [1], [2], and [5] above.) Most preferred is a compound represented by formula (I-4), a salt thereof, an N-oxide thereof, a solvate thereof, or a prodrug of these.

[Chem. 17]

(I-4)

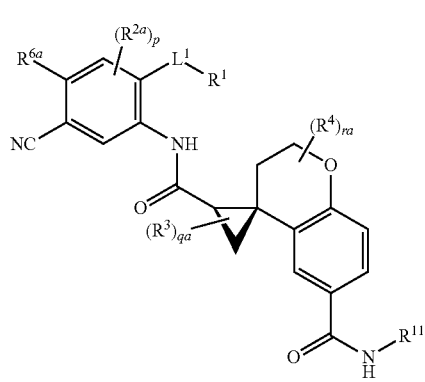

(In the formula, all the symbols have the same meanings as the symbols defined in items [1], [2], and [5] above.)

In the present invention, a further preferred aspect of the compound represented by formula (I) is a compound represented by formula (I-f), a salt thereof, an N-oxide thereof, a solvate thereof, or a prodrug of these.

[Chem. 18]

(I-f)

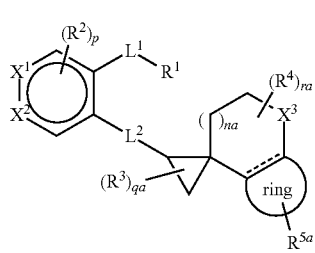

(In the formula, all the symbols have the same meanings as the symbols defined in items [1], [2], and [9] above.) Further preferred is a compound represented by formula (I-g), a salt thereof, an N-oxide thereof, a solvate thereof, or a prodrug of these.

[Chem. 19]

(I-g)

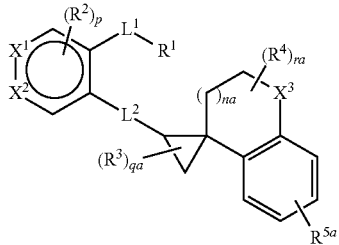

(In the formula, all the symbols have the same meanings as the symbols defined in items [1], [2], and [9] above.) Preferred is a compound represented by formula (I-h), a salt thereof, an N-oxide thereof, a solvate thereof, or a prodrug of these.

[Chem. 20]

(I-h)

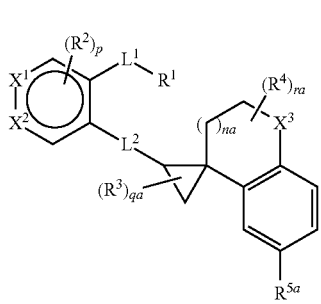

(In the formula, all the symbols have the same meanings as the symbols defined in items [1], [2], and [9] above.) Further preferred is a compound represented by formula (I-i), a salt thereof, an N-oxide thereof, a solvate thereof, or a prodrug of these.

[Chem. 21]

(I-i)

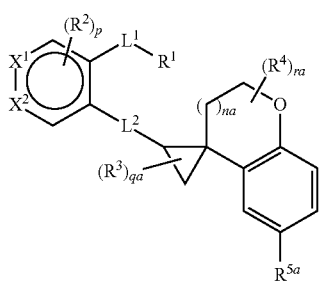

(In the formula, all the symbols have the same meanings as the symbols defined in items [1], [2], and [9] above.) Particularly preferred is a compound represented by formula (I-3), a salt thereof, an N-oxide thereof, a solvate thereof, or a prodrug of these.

[Chem. 22]

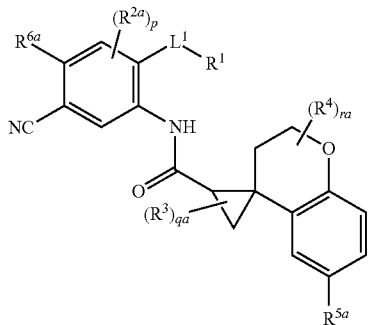

(I-3)

(In the formula, all the symbols have the same meanings as the symbols defined in items [1], [2], and [9] above.) Most preferred is a compound represented by formula (I-5), a salt thereof, an N-oxide thereof, a solvate thereof, or a prodrug of these.

[Chem. 23]

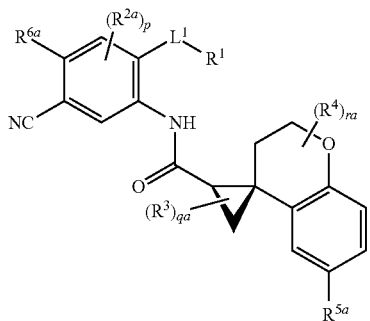

(I-5)

(In the formula, all the symbols have the same meanings as the symbols defined in items [1], [2], and [9] above.)

In the present invention, $L^1$ is independently preferably propylene, and $L^2$ is independently preferably —CH═CH—, —NHCO—, —CONH—, —NHSO$_2$—, or —SO$_2$NH— in a formula selected from the group of formula (I-a), formula (I-b), formula (I-c), formula (I-d), formula (I-e), formula (I-f), formula (I-g), formula (I-h), formula (I-i), and formula (I-1) above. More preferably, $L^1$ is propylene, and $L^2$ is —NHCO— or —CONH—. Further preferably, $L^1$ is propylene, and $L^2$ is —NHCO—.

In the present invention, $L^1$ is independently preferably propylene in a formula selected from the group of formula (I-2), formula (I-3), formula (I-4), and formula (I-5) above.

In the present invention, the most preferred aspect of formula (I) is any of the compound of Example 1, the compounds of Example 2-1 to Example 2-47, the compound of Example 3, the compounds of Example 4-1 to Example 4-3, the compounds of Examples 5 and 6, the compounds of Example 7-1 to Example 7-28, the compounds of Examples 8 and 9, the compounds of Example 10-1 to Example 10-12, the compound of Example 11, the compounds of Example 12-1 to Example 12-3, the compounds of Examples 13 to 17, the compounds of Example 18-1 to Example 18-3, the compound of Example 19, the compounds of Example 20-1 to Example 20-5, the compounds of Examples 21 and 22, the compounds of Example 23-1 and Example 23-2, the compounds of Examples 24 to 27, the compounds of Example 28-1 and Example 28-2, the compounds of Examples 29 and 30, the compounds of Example 31-1 and Example 31-2, the compound of Example 32, the compounds of Example 33-1 to Example 33-5, the compounds of Examples 34 to 36, the compounds of Example 37-1 and Example 37-2, the compounds of Example 38-1 and Example 38-2, and the compound of Example 39, a salt thereof, an N-oxide thereof, a solvate thereof, or a prodrug of these.

All of isomers fall within the scope of the present invention, unless otherwise specifically stated. For example, the alkyl groups, the alkoxy groups, the alkylene groups, and the like include linear and branched chain groups. The present invention also includes all of isomers due to a double bond, a ring, and a fused ring (E, Z, cis, and trans isomers), isomers due to the presence of an asymmetric carbon or the like (R and S isomers, α and β isomers, enantiomers, and diastereomers), optical isomers involving optical rotation (D, L, d, and l isomers), polar compounds separated by chromatography (high-polarity and low-polarity compounds), equilibrium compounds, rotational isomers, mixtures of any proportions of these compounds, and racemic mixtures. The present invention also includes all isomers due to tautomerism.

As is clear for a skilled person, the following symbols in the present invention have the following meanings, unless otherwise specifically stated.

[Chem. 24]

represents a bond into the plane of the paper (i.e., the α-configuration).

[Chem. 25]

represents a bond out of the plane of the paper (i.e., the β-configuration).

[Chem. 26]

represents an arbitrary mix of α-configuration and β-configuration.

[Salt]

The compound represented by formula (I) is converted into a salt using a known method.

The salt is preferably a pharmaceutically acceptable salt.

Preferably, the salt is water soluble.

Examples of the pharmaceutically acceptable salt include acid addition salts, alkali metal salts, alkali-earth metal salts, ammonium salts, amine salts, and the like.

Examples of the acid addition salts include inorganic acid salts such as hydrochloride, hydrobromate, hydroiodide, sulfates, phosphates, and nitrates, or organic acid salts such as acetates, lactates, tartrates, benzoates, citrates, methanesulfonate, ethanesulfonate, trifluoroacetate, benzenesulfonate, toluenesulfonate, isethionates, glucuronates, and gluconates.

Examples of the alkali metal salts include salts with potassium, sodium, and the like.

Examples of the alkali-earth metal salts include salts with calcium, magnesium, and the like.

Examples of the ammonium salts include salts with tetramethylammonium and the like.

Examples of the amine salts include salts with triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, and the like.

The compound used for the present invention may be transformed into an N-oxide using any method. N-Oxides refer to compounds represented by formula (I) with oxidized nitrogen atoms.

The compound represented by formula (I) and a salt thereof may be transformed into a solvate.

Preferably, the solvate is non-toxic and water soluble. Examples of suitable solvates include solvates using water and solvates using alcoholic solvents (for example, ethanol and the like). The solvate is preferably a hydrate.

[Prodrug]

A prodrug of the compound represented by formula (I) refers to a compound that is transformed into the compound represented by formula (I) in the body through reaction with an enzyme, stomach acid, or the like. The following are examples of prodrugs of the compounds represented by formula (I): a compound represented by formula (I) with an amino group that is acylated, alkylated, or phosphorylated (for example, a compound represented by formula (I) with an amino group that is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, or tert-butylated, and the like); a compound represented by formula (I) with a hydroxyl group that is acylated, alkylated, phosphorylated, or borated (for example, a compound represented by formula (I) with a hydroxyl group that is acetylated, palmitoylated, propanoylated, pivaloylated, succinylated, fumarylated, alanylated, or dimethylaminomethylcarbonylated, and the like); a compound represented by formula (I) with a carboxy group that is esterified or amidated (for example, a compound represented by formula (I) with a carboxy group that is ethylesterified, phenylesterified, carboxymethylesterified, dimethylaminomethylesterified, pivaloyloxymethylesterified, 1-{(ethoxycarbonyl)oxy}ethylesterified, phthalidylesterified, (5-methyl-2-oxo-1,3-dioxolen-4-yl)methylesterified, 1-{[(cyclohexyloxy)carbonyl]oxy}ethylesterified, or methylamidated, and the like); and the like. These compounds may be produced by a method known per se. The prodrug of the compound represented by formula (I) may be a hydrate or a nonhydrate. The prodrug of the compound represented by formula (I) may be one that transforms into the compound represented by formula (I) under physiological conditions, such as described in Pharmaceutical research and development, Vol. 7, Molecular Design, pp. 163-198, 1990, Hirokawa Publishing Company.

The atoms constituting the compounds represented by formula (I) may be replaced with their isotopes (for example, $^2H$, $^3H$, $^{13}C$, $^{14}C$, $^{15}N$, $^{16}N$, $^{17}O$, $^{18}O$, $^{18}F$, $^{35}S$, $^{36}Cl$, $^{77}Br$, $^{125}I$, and the like) or the like.

[Method of Production of Compounds Used for the Present Invention]

The compounds represented by formula (I) may be produced by known methods, for example, by the methods described below, methods equivalent thereto, or the methods described in the Examples. In the methods of production below, a raw material compound may be in the form of a salt. The salt may be any of the pharmaceutically acceptable salts exemplified for the compounds represented by formula (I).

The compound represented by formula (I) of which $L^2$ is —NHCO— (a compound represented by formula (IVa)) and the compound represented by formula (I) of which $L^2$ is —CONH— (a compound represented by formula (IVb)) can be produced by the methods represented by the following reaction scheme (Ia) and reaction scheme (Ib), respectively.

Reaction Scheme (Ia)

[Chem. 27]

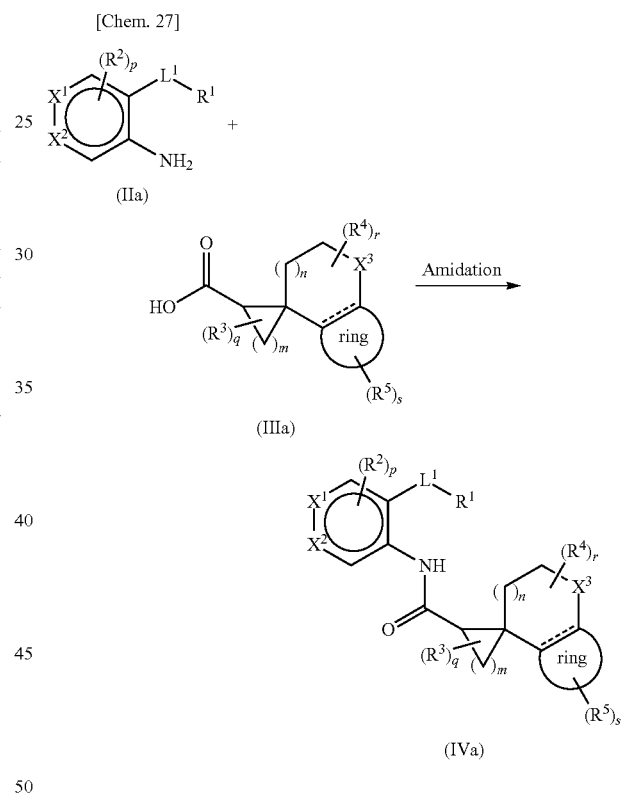

(In the formulae, all the symbols have the same meanings as the symbols defined in item [1] above.)

Reaction Scheme (Ib)

[Chem. 28]

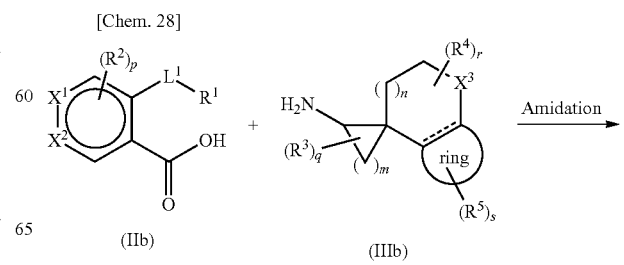

-continued

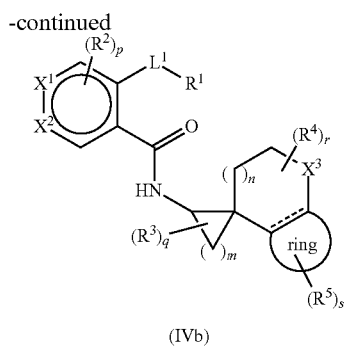

(IVb)

(In the formulae, all the symbols have the same meanings as the symbols defined in item [1] above.)

Specifically, the compound represented by formula (IVa) can be produced by amidation reaction of the compound represented by formula (IIa) and the compound represented by formula (IIIa). The compound represented by formula (IVb) can be produced by amidation reaction of the compound represented by formula (IIb) and the compound represented by formula (IIIb).

The amidation reaction is known and may be, for example,
(1) a method using an acid halide,
(2) a method using a mixed acid anhydride,
(3) a method using a condensing agent, or the like.

The following describes these methods in detail.

(1) In the method using an acid halide, for example, carboxylic acid is reacted with an acid halide reagent (oxalyl chloride, thionyl chloride, or the like) at about −20° C. to reflux temperature in an organic solvent (chloroform, dichloromethane, diethyl ether, tetrahydrofuran, or the like) or without solvent. The resulting acid halide is then reacted with an amine in an organic solvent (chloroform, dichloromethane, diethyl ether, tetrahydrofuran, or the like) at about 0 to 40° C. in the presence of a base (pyridine, triethylamine, dimethylaniline, dimethylaminopyridine, diisopropylethylamine, or the like). Alternatively, the resulting acid halide may be reacted with an amine at about 0 to 40° C. in an organic solvent (dioxane, tetrahydrofuran, or the like), using an alkaline aqueous solution (sodium bicarbonate water, a sodium hydroxide solution, or the like).

(2) In the method using a mixed acid anhydride, for example, carboxylic acid is reacted with an acid halide (pivaloyl chloride, tosyl chloride, mesyl chloride, or the like) or with an acid derivative (ethyl chloroformate, isobutyl chloroformate, or the like) at about 0 to 40° C. in an organic solvent (chloroform, dichloromethane, diethyl ether, tetrahydrofuran, or the like) or without solvent, in the presence of a base (pyridine, triethylamine, dimethylaniline, dimethylaminopyridine, diisopropylethylamine, or the like). The resulting mixed acid anhydride is then reacted with an amine at about 0 to 40° C. in an organic solvent (chloroform, dichloromethane, diethyl ether, tetrahydrofuran, or the like).

(3) In the method using a condensing agent, for example, carboxylic acid is reacted with an amine at about 0° C. to reflux temperature in an organic solvent (chloroform, dichloromethane, dimethylformamide, dimethylacetoamide, diethyl ether, tetrahydrofuran, or the like) or without solvent in the presence or absence of a base (pyridine, triethylamine, dimethylaniline, dimethylaminopyridine, or the like), using a condensing agent (1,3-dicyclohexylcarbodiimide (DCC), 1-ethyl-3-[3-(dimethylamino)propyl]carbodiimide (EDC), 1,1'-carbonyldiimidazole (CDI), 2-chloro-1-methylpyridiniumiodine, or 1-propylphosphonic acid cyclic anhydride (1-propanephosphonic acid cyclic anhydride (T3P) or the like)), with or without 1-hydroxybenzotriazole (HOBt).

Desirably, the reactions (1), (2), and (3) are all performed under anhydrous conditions in an inert gas (argon, nitrogen, or the like) atmosphere.

The compound represented by formula (I) of which $L^2$ is —NHSO$_2$— (a compound represented by formula (IVc)) and the compound represented by formula (I) of which $L^2$ is —SO$_2$NH— (a compound represented by formula (IVd)) can be produced by the methods represented by the following reaction scheme (Ic) and reaction scheme (Id), respectively.

Reaction Scheme (Ic)

[Chem. 29]

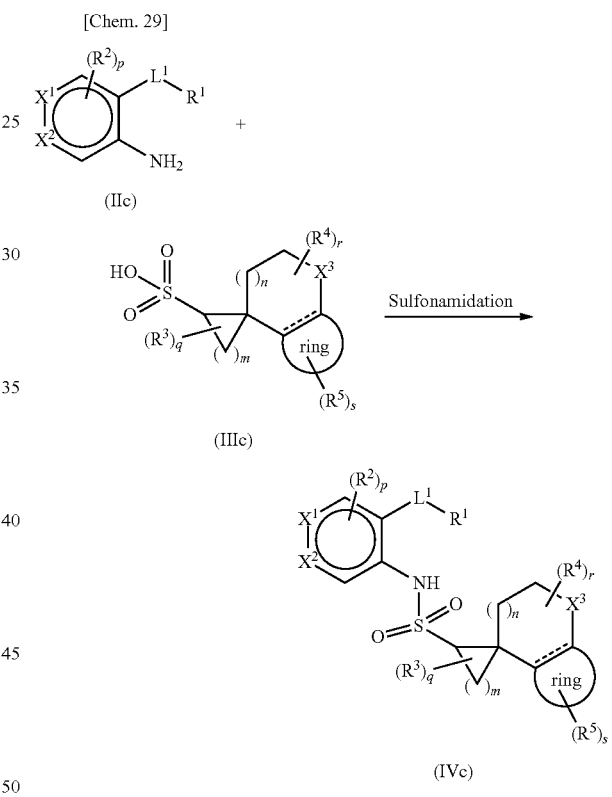

(In the formulae, all the symbols have the same meanings as the symbols defined in item [1] above.)

Reaction Scheme (Id)

[Chem. 30]

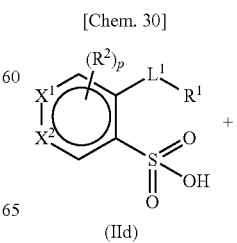

(IId)

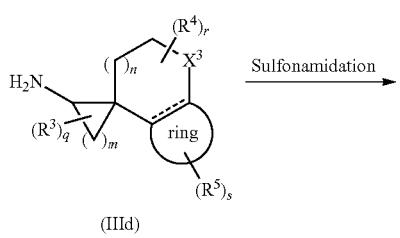

(IIId)

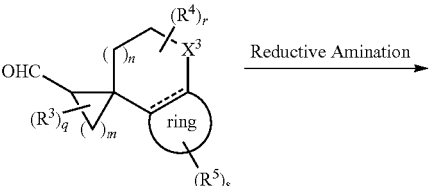

(IIIe)

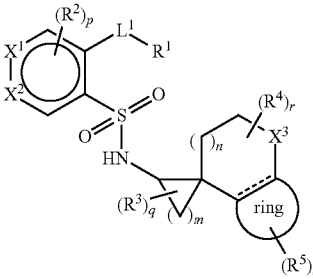

(IVd)

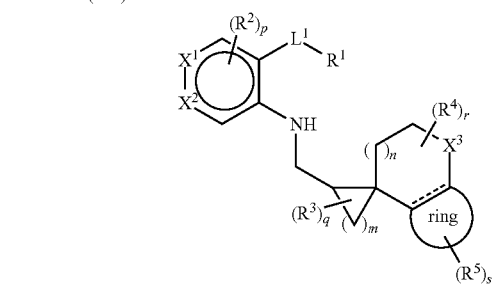

(IVe)

(In the formulae, all the symbols have the same meanings as the symbols defined in item [1] above.)

Specifically, the compound represented by formula (IVc) can be produced by sulfonamidation reaction of the compound represented by formula (IIc) and the compound represented by formula (IIIc). The compound represented by formula (IVd) can be produced by sulfonamidation reaction of the compound represented by formula (IId) and the compound represented by formula (IIId).

The sulfonamidation reaction is known. For example, sulfonic acid is reacted with an acid halide (oxalyl chloride, thionyl chloride, phosphorous pentachloride, phosphorous trichloride, or the like) at −20° C. to reflux temperature in an organic solvent (chloroform, dichloromethane, dichloroethane, diethyl ether, tetrahydrofuran, methyl t-butyl ether, or the like) or without solvent. The resulting sulfonyl halide is then reacted with an amine at about 0 to 40° C. in an organic solvent (chloroform, dichloromethane, dichloroethane, diethyl ether, tetrahydrofuran, or the like) in the presence of a base (diisopropylethylamine, pyridine, triethylamine, dimethylaniline, dimethylaminopyridine, or the like).

The compound represented by formula (I) of which $L^2$ is —NHCH$_2$— (a compound used for the present invention represented by formula (IVe)) and the compound represented by formula (I) of which $L^2$ is —CH$_2$NH— (a compound represented by formula (IVf)) can be produced by the methods represented by the following reaction scheme (Ie) and reaction scheme (If), respectively.

Reaction Scheme (Ie)

[Chem. 31]

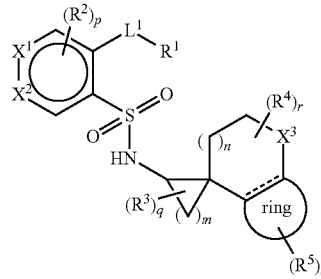

(IIe)

Reaction Scheme (If)

[Chem. 32]

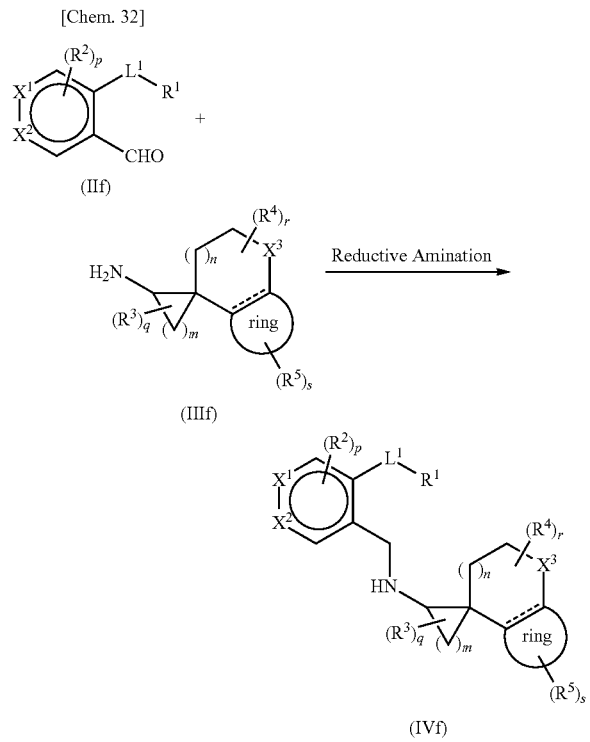

(In the formulae, all the symbols have the same meanings as the symbols defined in item [1] above.)

Specifically, the compound represented by formula (IVe) can be produced by reductive amination reaction of the compound represented by formula (IIe) and the compound represented by formula (IIIe). The compound represented by formula (IVf) can be produced by reductive amination reaction of the compound represented by formula (IIf) and the compound represented by formula (IIIf).

The reductive amination reaction is known. For example, the reaction is performed in an organic solvent (dichloroethane, dichloromethane, dimethylformamide, acetic acid, a mixture of these, or the like) at about 0 to 40° C. in the presence of a reducing agent (sodium triacetoxyborohydride, sodium cyanoborohydride, sodium borohydride, or the like).

The compound represented by formula (I) of which $L^2$ is —OCH$_2$— (a compound used for the present invention represented by formula (IVg)) and the compound represented by formula (I) of which $L^2$ is —CH$_2$O— (a compound represented by formula (IVh)) can be produced by the methods represented by the following reaction scheme (Ig) and reaction scheme (Ih), respectively.

Reaction Scheme (Ig)

[Chem. 33]

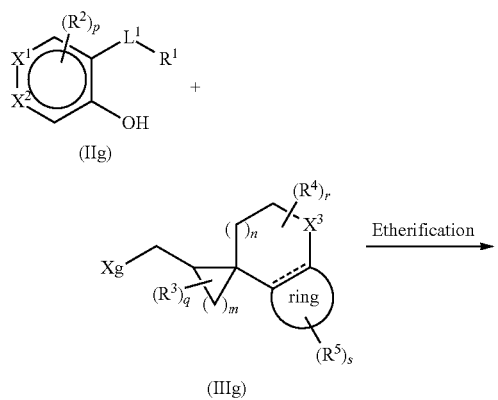

(IIg)

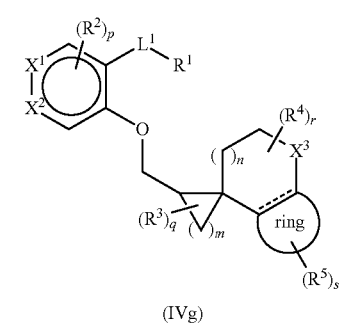

(IVg)

(In the formulae, Xg is halogen, tosylate, or mesylate, and the other symbols have the same meanings as the symbols defined in item [1] above.)

Reaction Scheme (Ih)

[Chem. 34]

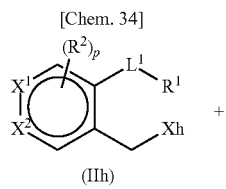

(IIh)

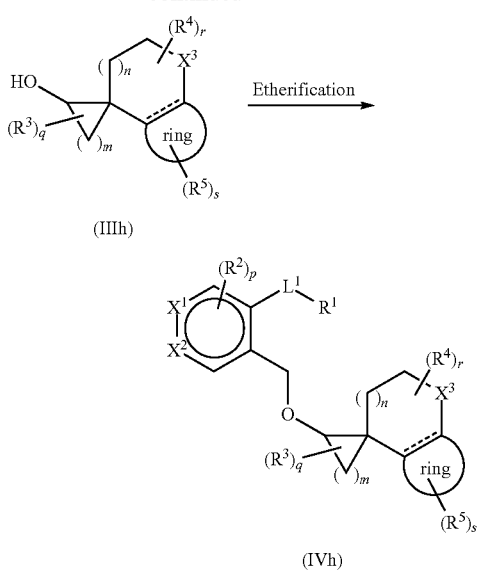

(In the formulae, Xh is halogen, tosylate, or mesylate, and the other symbols have the same meanings as the symbols defined in item [1] above.)

Specifically, the compound represented by formula (IVg) can be produced by etherification reaction of the compound represented by formula (IIg) and the compound represented by formula (IIIg). The compound represented by formula (IVh) can be produced by etherification reaction of the compound represented by formula (IIh) and the compound represented by formula (IIIh).

The etherification reaction is known. For example, the reaction is performed in an organic solvent (dimethylformamide, dimethylsulfoxide, chloroform, dichloromethane, diethyl ether, tetrahydrofuran, methyl t-butyl ether, or the like) at about 0 to 100° C. in the presence of an alkali metal hydroxide (sodium hydroxide, potassium hydroxide, lithium hydroxide, or the like), an alkali earth metal hydroxide (barium hydroxide, calcium hydroxide, or the like), a carbonate (sodium carbonate, potassium carbonate, or the like), an aqueous solution thereof, or a mixture of these.

The compound represented by formula (I) of which $L^2$ is —SCH$_2$— (a compound used for the present invention represented by formula (IVj)) and the compound represented by formula (I) of which $L^2$ is —CH$_2$S-(a compound represented by formula (IVk)) can be produced by the methods represented by the following reaction scheme (Ij) and reaction scheme (Ik), respectively.

Reaction Scheme (Ij)

[Chem. 35]

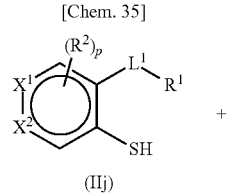

(IIj)

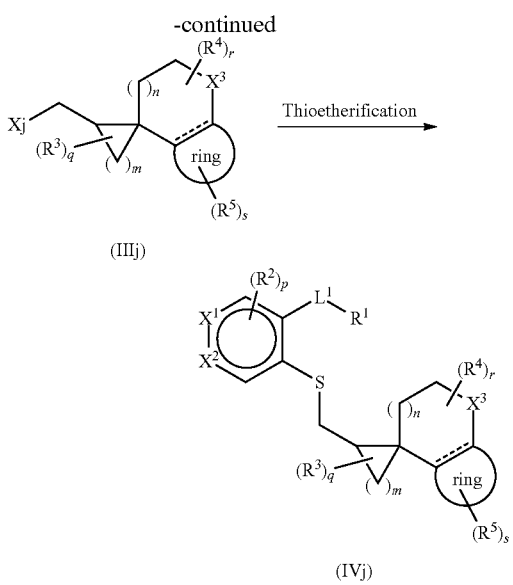

(In the formulae, Xj is halogen, tosylate, or mesylate, and the other symbols have the same meanings as the symbols defined in item [1] above.)

Reaction Scheme (Ik)

[Chem. 36]

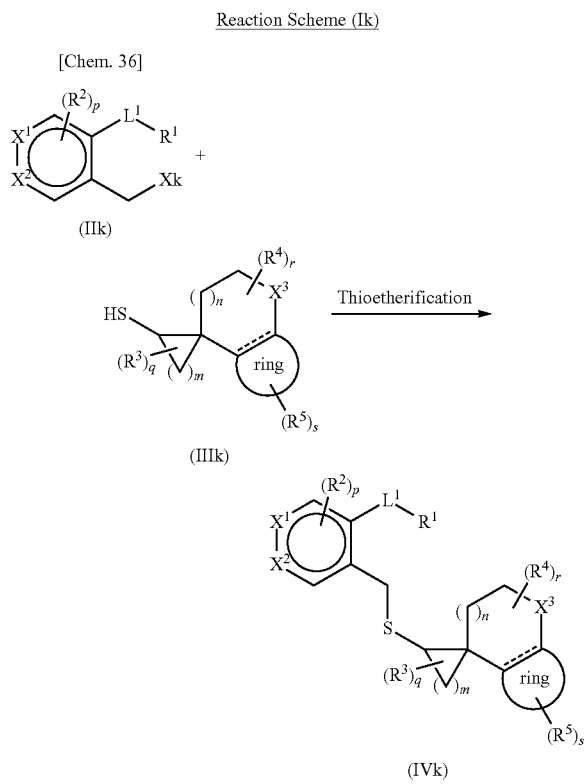

(In the formulae, Xk is halogen, tosylate, or mesylate, and the other symbols have the same meanings as the symbols defined in item [1] above.)

Specifically, the compound represented by formula (IVj) can be produced by thioetherification reaction of the compound represented by formula (IIj) and the compound represented by formula (IIIj). The compound represented by formula (IVk) can be produced by thioetherification reaction of the compound represented by formula (IIk) and the compound represented by formula (IIIk).

The thioetherification reaction is known. For example, the reaction is performed in an organic solvent (dimethylformamide, dimethylsulfoxide, chloroform, dichloromethane, diethyl ether, tetrahydrofuran, methyl t-butyl ether, or the like) at 0 to 100° C. in the presence of an alkali metal hydroxide (sodium hydroxide, potassium hydroxide, lithium hydroxide, or the like), an alkali earth metal hydroxide (barium hydroxide, calcium hydroxide, or the like), a carbonate (sodium carbonate, potassium carbonate, or the like), an aqueous solution thereof, or a mixture of these.

The compound represented by formula (I) of which $L^2$ is —S(O)CH$_2$— or —SO$_2$CH$_2$— can be produced by appropriately subjecting the sulfur atom of the compound represented by formula (IVj) above to oxidation reaction.

The compound represented by formula (I) of which $L^2$ is —CH$_2$S(O)— or —CH$_2$SO$_2$— can be produced by appropriately subjecting the sulfur atom of the compound represented by formula (IVk) above to oxidation reaction.

The oxidation reaction (sulfoxidation reaction: —SCH$_2$—→—S(O)CH$_2$—, or —CH$_2$S—→—CH$_2$S(O)—) is known. For example, the reaction is performed in an organic solvent (dichloromethane, chloroform, benzene, hexane, methanol, t-butyl alcohol, acetone, acetonitrile, tetrahydrofuran, acetic acid, N,N-dimethylformamide, or the like), in water, or in a mixed solvent of these at about −40 to 0° C. in the presence of 1 to 1.2 equivalents of an oxidizing agent (hydrogen peroxide, sodium periodate, acyl nitrite, sodium perborate, sodium hypochlorite, a peracid (3-chloroperbenzoic acid, peracetic acid, or the like), Oxone (trade name, hereinafter, simply referred to as Oxone; potassium peroxymonosulfate), potassium permanganate, chromic acid, dimethyldioxolan, or the like).

The oxidation reaction (sulfonation reaction: —SCH$_2$—→—SO$_2$CH$_2$—, or —CH$_2$S—→—CH$_2$SO$_2$—) is known. For example, the reaction is performed in a suitable organic solvent (dichloromethane, chloroform, benzene, hexane, methanol, t-butyl alcohol, acetone, acetonitrile, tetrahydrofuran, acetic acid, N,N-dimethylformamide, or the like), in water, or in a mixed solvent of these at about 20 to 60° C. in the presence of an excess oxidizing agent (hydrogen peroxide, sodium periodate, acyl nitrite, sodium perborate, sodium hypochlorite, a peracid (3-chloroperbenzoic acid, peracetic acid, or the like), Oxone (trade name; potassium peroxymonosulfate), potassium permanganate, chromic acid, dimethyldioxolan, or the like).

The compound represented by formula (I) of which $L^2$ is —CH=CH— (a compound represented by formula (IVm)) can be produced by the method represented by the following reaction scheme (Im).

Reaction Scheme (Im)

[Chem. 37]

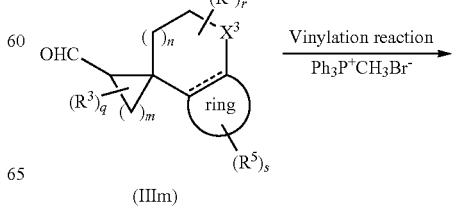

-continued

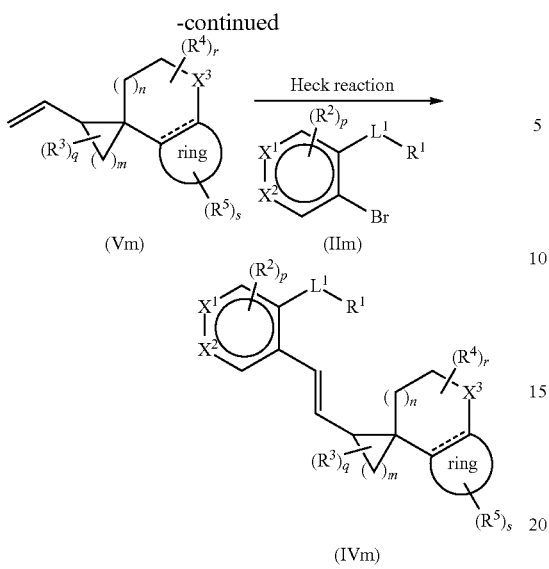

(Vm)  (IIm)

(IVm)

(In the formulae, all the symbols have the same meanings as the symbols defined in item [1] above.)

Specifically, the compound represented by formula (IVm) can be produced by the Heck reaction of the compound represented by formula (IIm) with the compound represented by formula (Vm) produced by vinylation reaction of the compound represented by formula (IIIm).

The vinylation reaction is known. For example, the reaction is performed using the compound represented by formula (IIIm) and methyltriphenylphosphonium bromide in an organic solvent (for example, acetonitrile, methylene chloride, tetrahydrofuran, toluene, benzene, an appropriate mixed solvent of these organic solvents, or the like) at about 0° C. to 120° C. in the presence of a base (for example, potassium carbonate, sodium hydride, potassium hydride, n-butyllithium, potassium tert-butoxide, 1,8-diazabicyclo [5.4.0]undec-7-ene triethylamine (DBU), or the like).

The Heck reaction is known. For example, the reaction is performed in an organic solvent (for example, toluene, diethyl ether, benzene, dichlorobenzene, dimethylformamide, an appropriate mixed solvent of these organic solvents, or the like) at about 0° C. to 120° C. in the presence of a base (for example, tripotassium phosphate, sodium bicarbonate, triethylamine, or the like) and a catalyst (for example, a palladium catalyst (for example, palladium chloride, palladium acetate, tetrakis(triphenylphosphine)palladium(0), or the like), a nickel catalyst (for example, tetrakis (triphenylphosphine)nickel, bis(triphenylphosphine)nickel (II), or the like), a cobalt catalyst (for example, cobalt chloride, or the like), a copper catalyst (for example, copper chloride, or the like), a zinc catalyst (for example, zinc or the like), an appropriate mixed catalyst of these catalysts, or the like), in the presence or absence of a phosphorus reagent (for example, 1,3-bis(diphenylphosphino)propane (dppp), Ph$_2$P—(CH$_2$)$_6$—PPh$_2$, or the like).

The compound represented by formula (I) of which L$^2$ is —CH$_2$CH$_2$— can be produced by appropriately subjecting the "—CH=CH—" of the compound represented by formula (IVm) above to reduction reaction.

The reduction reaction is known. For example, the reaction is performed in an organic solvent (for example, tetrahydrofuran, dioxane, dimethoxyethane, diethyl ether, methanol, ethanol, benzene, toluene, acetone, methyl ethyl ketone, acetonitrile, dimethylformamide, water, ethyl acetate, acetic acid, an appropriate mixed solvent of these organic solvents, or the like) in a hydrogen atmosphere under normal or pressurized pressure condition, in the presence of ammonium formate or in the presence of hydrazine at about 0 to 200° C., in the presence of a hydrogenation catalyst (palladium-carbon, palladium black, palladium, palladium hydroxide, platinum dioxide, platinum-carbon, nickel, Raney nickel, ruthenium chloride, or the like), in the presence or absence of an acid (hydrochloric acid, sulfuric acid, hypochlorous acid, boric acid, tetrafluoroboric acid, acetic acid, p-toluenesulfonic acid, oxalic acid, trifluoroacetic acid, formic acid, or the like).

The compound represented by formula (IIIa) in reaction scheme (Ia) of which q is 0 and of which m is 1 (a compound represented by formula (IIIaa)) can be produced by the method represented by the following reaction scheme (Iaa).

Reaction Scheme (Iaa)

[Chem. 38]

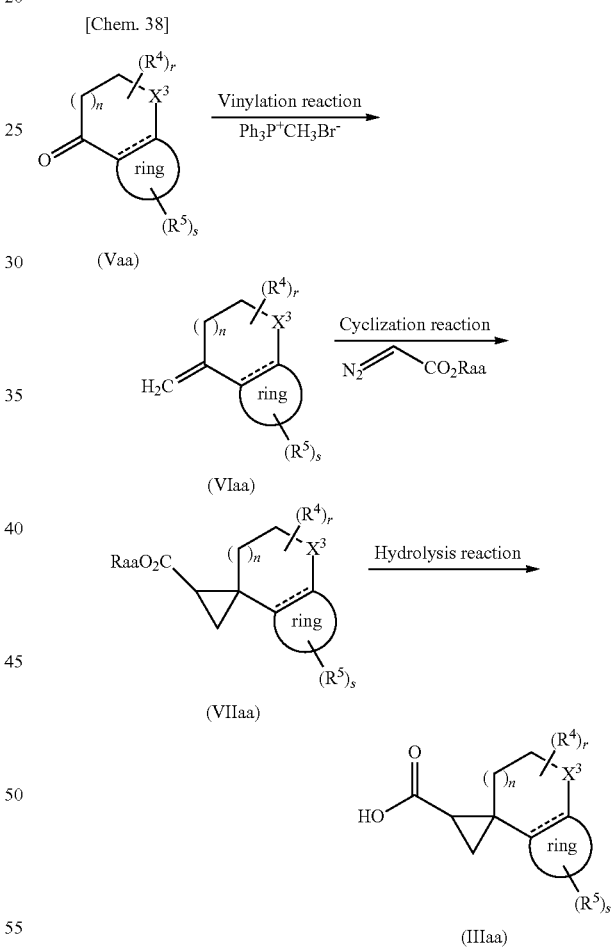

(In the formulae, Raa is C1-4 alkyl, and the other symbols have the same meanings as the symbols defined in items [1] and [2] above.)

Specifically, the compound represented by formula (IIIaa) can be produced by subjecting the compound represented by formula (VIaa) produced by vinylation reaction of the compound represented by formula (Vaa) to cyclization reaction and then to hydrolysis reaction.

The vinylation reaction is known. For example, the reaction is performed using the compound represented by formula (Vaa) and methyltriphenylphosphonium bromide in an organic solvent (for example, acetonitrile, methylene chloride, tetrahydrofuran, toluene, benzene, an appropriate mixed solvent of these organic solvents, or the like) at about 0° C. to 120° C. in the presence of a base (for example, potassium carbonate, sodium hydride, potassium hydride, n-butyllithium, potassium tert-butoxide, 1,8-diazabicyclo[5.4.0]undec-7-ene triethylamine (DBU), or the like).

The cyclization reaction is known. For example, the reaction is performed using the compound represented by formula (VIaa) and a diazo compound in an organic solvent (for example, toluene, benzene, methylene chloride, dichloroethane, methanol, ethanol, hexane, tetrahydrofuran, water, an appropriate mixed solvent of these organic solvents, or the like) at about −78° C. to 120° C. in the presence of a catalyst (a ruthenium catalyst (for example, a dichloro(cymene)ruthenium dimer ([Ru(p-cymene)Cl$_2$]$_2$), RuCl$_2$(PPh$_3$)$_3$, RuCl(Cp)(PPh$_3$)$_2$, or the like), a rhodium catalyst (for example, Rh$_2$(O—CO-heptyl)$_4$, Rh$_2$(O—CO-tBu)$_4$, Rh$_2$(OAc)$_4$, Rh$_2$(O-Piv)$_4$, Rh$_2$((S)-PTTL)$_4$, Rh$_2$((S)-DOSP)$_4$, Rh$_2$(esp)$_2$, Rh$_2$((S)-NTTL)$_4$, or the like), a silver catalyst (for example, silver(I) tetrafluoroborate, or the like), a copper catalyst (for example, CuOTf, Cu(OAc)$_2$, [Cu(MeCN)$_4$]PF$_6$, or the like), a tin catalyst (for example, Sn(tpp)(OTf)$_2$, or the like), an iron catalyst (for example, [Fe(Cp)(CO)$_2$(thf)]BF$_4$, or the like), a cobalt catalyst, 2,6-bis(4-isopropyl-4,5-dihydrooxazol-2-yl)pyridine, 2,6-bis((S)-4-isopropyl-4,5-dihydrooxazol-2-yl)pyridine, or 2,6-bis((R)-4-isopropyl-4,5-dihydrooxazol-2-yl)pyridine). In the cyclization reaction, an optically active tricyclic spiro compound (an optical isomer of the compound represented by formula (VIIaa)) can be produced by using a known optically active asymmetric catalyst.

The hydrolysis reaction (deprotection reaction of the carboxyl group) is known, and alkali hydrolysis or the like is an example thereof. For example, the deprotection reaction by alkali hydrolysis is performed in an organic solvent (methanol, tetrahydrofuran, dioxane, or the like) at 0 to 100° C. using an alkali metal hydroxide (sodium hydroxide, potassium hydroxide, lithium hydroxide, or the like), an alkali earth metal hydroxide (barium hydroxide, calcium hydroxide, or the like), a carbonate (sodium carbonate, potassium carbonate, or the like), an aqueous solution thereof, or a mixture of these.

The compound represented by formula (IIIb) in reaction scheme (Ib), the compound represented by formula (IIId) in reaction scheme (Id), or the compound represented by formula (IIIf) in reaction scheme (If) of which m is 1 can be produced from the compound represented by formula (IIIaa) in reaction scheme (Iaa) above using a known method, for example, using the method described in Comprehensive Organic Transformations: A Guide to Functional Group Preparations, 2nd Edition (Richard C. Larock, John Wiley & Sons Inc., 1999).

The compound represented by formula (IIIc) in reaction scheme (Ic) of which m is an integer of 1 can be produced from the compound represented by formula (IIIaa) in reaction scheme (Iaa) above using a known method, for example, using the method described in Comprehensive Organic Transformations: A Guide to Functional Group Preparations, 2nd Edition (Richard C. Larock, John Wiley & Sons Inc., 1999).

The compound represented by formula (IIIe) in reaction scheme (Ie) or the compound represented by formula (IIIm) in reaction scheme (Im) of which m is 1 can be produced from the compound represented by formula (IIIaa) in reaction scheme (Iaa) above using a known method, for example, using the method described in Comprehensive Organic Transformations: A Guide to Functional Group Preparations, 2nd Edition (Richard C. Larock, John Wiley & Sons Inc., 1999).

The compound represented by formula (IIIg) in reaction scheme (Ig) or the compound represented by formula (IIIj) in reaction scheme (Ij) of which m is 1 can be produced from the compound represented by formula (IIIaa) in reaction scheme (Iaa) above by reducing the carboxylic acid to produce a primary alcohol derivative and then transforming the alcohol derivative into a halogen derivative, a tosylate derivative, or a mesylate derivative, using a known method, for example, using the method described in Comprehensive Organic Transformations: A Guide to Functional Group Preparations, 2nd Edition (Richard C. Larock, John Wiley & Sons Inc., 1999).

The compound represented by formula (IIIh) in reaction scheme (Ih) of which m is 1 can be produced from the compound represented by formula (IIIaa) in reaction scheme (Iaa) above using a known method, for example, using the method described in Comprehensive Organic Transformations: A Guide to Functional Group Preparations, 2nd Edition (Richard C. Larock, John Wiley & Sons Inc., 1999) or in Tetrahedron Letter, Vol. 28, pp. 4489-4492, 1987.

The compound represented by formula (IIIk) in reaction scheme (Ik) of which m is 1 can be produced by producing a secondary alcohol derivative from the compound represented by formula (IIIaa) in reaction scheme (Iaa) above and then transforming the alcohol derivative into a thiol derivative, using a known method, for example, using the method described in Comprehensive Organic Transformations: A Guide to Functional Group Preparations, 2nd Edition (Richard C. Larock, John Wiley & Sons Inc., 1999) or in Tetrahedron Letter, Vol. 28, pp. 4489-4492, 1987.

Of the compounds represented by formula (IIIa), formula (IIIb), formula (IIIc), formula (IIId), formula (IIIe), formula (IIIf), formula (IIIg), formula (IIIh), formula (IIIj), formula (IIIk), and formula (IIIm) used as starting materials in the reaction schemes, the compounds with an m of 1 and a q of an integer of 1 to 3 or the compounds with an m of an integer of 2 to 4 and a q of an integer of 1 to 6 are known or can be produced with ease using a known method, for example, using the method described in Comprehensive Organic Transformations: A Guide to Functional Group Preparations, 2nd Edition (Richard C. Larock, John Wiley & Sons Inc., 1999).

The compounds represented by formulae (IIa), (IIb), (IIc), (IId), (IIe), (IIf), (IIg), (IIh), (IIj), (IIk), (IIm), and (Vaa) used as starting materials in the reaction schemes are known or can be produced with ease using a known method, for example, using the method described in Comprehensive Organic Transformations: A Guide to Functional Group Preparations, 2nd Edition (Richard C. Larock, John Wiley & Sons Inc., 1999).

The compound used for the present invention having an amino group, a carboxyl group, or a hydroxyl group can be produced using a compound that has been protected, as required, by a protecting group commonly used for such groups, for example, a protecting group described in Comprehensive Organic Transformations: A Guide to Functional Group Preparations, 2nd Edition (Richard C. Larock, John Wiley & Sons Inc., 1999), by performing a known deprotection reaction or, for example, the deprotection reaction described in Comprehensive Organic Transformations: A Guide to Functional Group Preparations, 2nd Edition (Richard C. Larock, John Wiley & Sons Inc., 1999) after the completion of the amidation reaction shown in reaction scheme (Ia) or (Ib) above, the sulfonamidation reaction shown in reaction scheme (Ic) or (Id) above, the reductive amination reaction shown in reaction scheme (Ie) or (If) above, the etherification reaction shown in reaction scheme (Ig) or (Ih) above, the thioetherification reaction shown in reaction scheme (Ij) or (Ik) above, or the Heck reaction shown in reaction scheme (Im) above, or after a suitable reaction process.

The compounds represented by formula (I) other than the compounds described above may be produced by combining the Examples described in this specification or by combining known methods, for example, the methods described in Comprehensive Organic Transformations: A Guide to Functional Group Preparations, 2nd Edition (Richard C. Larock, John Wiley & Sons Inc., 1999).

When the compound used for the present invention is an optically active compound, the compound also can be produced using a starting material or a reagent having optical activity or produced by optically separating a racemic intermediate and then converting to the compound used for the present invention therefrom or optically separating a racemic form of the compound used for the present invention.

The optical separation method is known. In an example method, a salt, a complex, or the like is formed with another optically active compound, and the compound of interest is isolated after recrystallization or directly separated using a chiral column or the like.

In the reactions in this specification, reactions involving heating may be performed using a water bath, an oil bath, a sand bath, or a microwave, as is evident to a skilled person.

In the reactions in this specification, a solid-phase-supported reagent that is supported on a polymer (for example, polystyrene, polyacrylamide, polypropylene, polyethylene glycol, or the like) may be appropriately used.

In the reactions in this specification, the reaction products may be purified by using ordinary purification means, for example, such as distillation under normal pressure or reduced pressure, high-performance liquid chromatography using silica gel or magnesium silicate, thin-layer chromatography, methods using an ion-exchange resin or a scavenger resin, column chromatography, washing, and recrystallization. The purification may be performed after each reaction or after several reactions.

Preparations are usually formed using the compound used for the present invention and various additives or pharmaceutically acceptable excipients such as solvents and are administered as oral or parenteral preparation systemically or locally. The pharmaceutically acceptable excipients mean materials which are generally used for the preparation of drugs except for the active substances. The pharmaceutically acceptable excipients are preferably harmless excipients which do not show any pharmacological effect at the dosage of the preparation and which do not inhibit the treatment effect of the active substances. In addition, the pharmaceutically acceptable excipients can also be used to enhance effectiveness of the active substances and the preparations, make production of the drugs easy, stabilize quality or improve usability. Specifically, the materials described in "Japanese Pharmaceutical Excipients directory 2016" (Yakuji nippo sha, 2016) (edited by Japan Pharmaceutical Excipients Council)", etc. may be appropriately selected according to intentions.

Dosage forms for administration include, for example, oral preparations (e.g.: tablets, capsules, granules, powders, oral solutions, syrups, oral jelly agents, etc.), oro-mucosal preparations (e.g.: tablets for oro-mucosal application, sprays for oro-mucosal application, semi-solid preparations for oro-mucosal application, gargles, etc.), preparations for injection (e.g.: injections, etc.), preparations for dialysis (e.g.: dialysis agents, etc.), preparations for inhalation (e.g.: inhalations, etc.), preparations for ophthalmic application (e.g.: ophthalmic liquids and solutions, ophthalmic ointments, etc.), preparations for otic application (e.g.: ear preparation, etc.), preparations for nasal application (e.g.: nasal preparations, etc.), preparations for *recta* (e.g.: suppositories, semi-solid preparations for rectal application, enemas for rectal application, etc.), preparations for vaginal application (e.g.: tablets for vaginal use, suppositories for vaginal use, etc.), preparations for cutaneous application (e.g.: solid preparations for cutaneous application, liquids and solutions for cutaneous application, sprays, ointment, creams, gels, patches, etc.), and the like.

The dose of the compound used for the present invention varies with age, body weight, symptom, therapeutic effect, route of administration, duration of treatment, and the like. In general, an amount in the range of 1 ng to 1000 mg is orally administered per adult per dose once or several times per day. Alternatively, an amount in the range of 0.1 ng to 100 mg is parenterally administered per adult per dose once or several times per day or intravenously administered continuously over between an hour to 24 hours per day. As described above, the dose varies with various conditions. Thus, an amount lower than the dose is sometimes sufficient, or administration of a dose exceeding the ranges is sometimes required.

[Immune Checkpoint Inhibitor]

In the present invention, an immune checkpoint molecule means a molecule which transmits a suppressive cosignal and thus exhibits immunosuppressive function. Known immune checkpoint molecules are CTLA-4, PD-1, PD-L1 (programmed cell death-ligand 1), PD-L2 (programmed cell death-ligand 2), LAG-3 (Lymphocyte activation gene 3), TIM3 (T cell immunoglobulin and mucin-3), BTLA (B and T lymphocyte attenuator), B7H3, B7H4, CD160, CD39, CD73, A2aR (adenosine A2a receptor), KIR (killer inhibitory receptor), VISTA (V-domain Ig-containing suppressor of T cell activation), IDO1 (Indoleamine 2,3-dioxygenase), Arginase I, TIGIT (T cell immunoglobulin and ITIM domain), CD115, and the like (see, Nature Reviews Cancer, 12, p. 252-264, 2012 and Cancer Cell, 27, p. 450-461, 2015), but the immune checkpoint molecule is not particularly limited as long as the molecule has a function which meets the definition.

The immune checkpoint inhibitor used for the combination of the present invention is a substance which inhibits the function of an immune checkpoint molecule. The immune checkpoint inhibitor is not particularly limited as long as the inhibitor is a substance which can inhibit the function (signal) of an immune checkpoint molecule.

The immune checkpoint inhibitor is preferably a human immune checkpoint molecule inhibitor, further preferably a neutralizing antibody to a human immune checkpoint molecule.

The immune checkpoint inhibitor is, for example, an inhibitor of an immune checkpoint molecule selected from the group consisting of CTLA-4, PD-1, PD-L1, PD-L2, LAG-3, TIM3, BTLA, B7H3, B7H4, CD160, CD39, CD73, A2aR, KIR, VISTA, IDO1, Arginase I, TIGIT, and CD115. Although examples of the immune checkpoint inhibitor are shown below, the immune checkpoint inhibitor is not limited to the examples.

Examples of the immune checkpoint inhibitor include an anti-CTLA-4 antibody (for example, ipilimumab (Yervoy (registered trademark)) and Tremelimumab), an anti-PD-1 antibody (for example, a human anti-human PD-1 monoclonal (neutralizing) antibody (for example, nivolumab (Opdivo (registered trademark)) and REGN-2810) and a humanized anti-human PD-1 monoclonal (neutralizing) antibody (for example, Pembrolizumab (KEYTRUDA (registered trademark)), PDR-001, BGB-A317, and AMP-514 (MEDI0680)), an anti-PD-L1 antibody (for example, Atezolizumab (RG7446 and MPDL3280A), Avelumab (PF-06834635 and MSB0010718C), Durvalumab (MEDI4736) and BMS-936559), an anti-PD-L2 antibody, PD-L1 fusion protein, PD-L2 fusion protein (for example, AMP-224), an anti-Tim-3 antibody (for example, MBG453), an anti-LAG-3 antibody (for example, BMS-986016 and LAG525), an anti-KIR antibody (for example, Lirilumab), and the like. Antibodies containing heavy chain and light chain complementarity-determining regions (CDRs) or a variable region (VR) of the known antibodies are also embodiments of the immune checkpoint inhibitor. For example, another embodiment of the anti-PD-1 antibody is, for example, an antibody containing the heavy chain and light chain complementarity-determining regions (CDRs) or a variable region (VR) of nivolumab.

Examples of the antibody containing heavy chain and light chain complementarity-determining regions (CDRs) or a variable region (VR) of nivolumab include (1) anti-PD-1 antibodies containing (a) heavy chain variable region CDR1 having the amino acid sequence of SEQ ID NO: 3, (b) heavy chain variable region CDR2 having the amino acid sequence of SEQ ID NO: 4, (c) heavy chain variable region CDR3 having the amino acid sequence of SEQ ID NO: 5, (d) light chain variable region CDR1 having the amino acid sequence of SEQ ID NO: 6, (e) light chain variable region CDR2 having the amino acid sequence of SEQ ID NO: 7, and (f) light chain variable region CDR3 having the amino acid sequence of SEQ ID NO: 8 or (2) anti-PD-1 antibodies containing the heavy chain variable region having the amino acid sequence of SEQ ID NO: 1 and the light chain variable region having the amino acid sequence of SEQ ID NO: 2 (preferably, an isolated human monoclonal IgG4 antibody of (1) or (2)).

The immune checkpoint inhibitor used for the combination of the present invention is preferably an anti-CTLA-4 antibody, an anti-PD-1 antibody, an anti-PD-L1 antibody, an anti-PD-L2 antibody, PD-L1 fusion protein, or PD-L2 fusion protein. An anti-CTLA-4 antibody, an anti-PD-1 antibody, an anti-PD-L antibody, an anti-PD-L2 antibody, PD-L1 fusion protein, and PD-L2 fusion protein are further preferred. An anti-CTLA-4 antibody and an anti-PD-1 antibody are particularly preferred. The anti-PD-1 antibody is preferably an antibody containing the heavy chain and light chain complementarity-determining regions (CDRs) or a variable region (VR) of nivolumab (including nivolumab), further preferably nivolumab.

In the present invention, any one kind or any two or more kinds of these immune checkpoint inhibitors can be used in combination with the compound used for the present invention.

The dose of the immune checkpoint inhibitor used for the combination of the present invention varies with age, body weight, symptom, therapeutic effect, route of administration, duration of treatment, and the like but is adjusted in a manner that the optimal desired effects are obtained.

When an anti-PD-1 antibody is used for example, an embodiment of the dose is 0.1 to 20 mg/kg body weight. When nivolumab is used for example, an embodiment of the dose is 0.3 to 10 mg/kg body weight, preferably 2 mg/kg, 3 mg/kg, or 6 mg/kg body weight.

When an anti-CTLA-4 antibody is used for example, an embodiment of the dose is 0.1 to 20 mg/kg body weight, preferably 0.1 to 10 mg/kg body weight, more preferably 3 mg/kg or 10 mg/kg body weight.

[Toxicity]

The combination of the present invention has low toxicity and can be thus safely used as a drug.

[Drug Applications]

The combination of the present invention is useful for the treatment of cancer.

More specifically, examples of the cancer include leukemia (for example, acute myelogenous leukemia, chronic myelogenous leukemia, acute lymphoblastic leukemia, and chronic lymphocytic leukemia), malignant lymphoma (Hodgkin's lymphoma and non-Hodgkin's lymphoma (for example, adult T-cell leukemia, follicular lymphoma, and diffuse large B-cell lymphoma)), multiple myeloma, myelodysplastic syndrome, head and neck cancer, esophageal cancer, esophageal adenocarcinoma, stomach cancer, duodenal cancer, colorectal cancer, colon cancer, rectal cancer, liver cancer (for example, hepatocellular carcinoma), gallbladder/bile duct cancer, biliary tract cancer, pancreatic cancer, thyroid cancer, lung cancer (for example, non-small cell lung cancer (for example, squamous non-small cell lung cancer and non-squamous non-small cell lung cancer) and small cell lung cancer), breast cancer, ovarian cancer (for example, serous ovarian cancer), cervical cancer, corpus uteri cancer, endometrial cancer, vaginal cancer, vulvar cancer, renal cancer (for example, renal cell carcinoma), renal pelvis/ureter cancer, urothelial cancer (for example, bladder cancer and upper urinary tract cancer), penile cancer, prostate cancer, testicular tumor (for example, germ cell tumor), osteosarcoma/soft tissue sarcoma, malignant bone tumor, skin cancer (for example, uveal malignant melanoma, malignant melanoma, and Merkel-cell carcinoma), thymoma, mesothelioma, glioblastoma, blood cancer, cancer of unknown primary, and the like.

For example, it is expected that the combination of the present invention exhibits its anti-tumor effect the most especially in a patient with cancer in which the therapeutic effect of an immune checkpoint inhibitor or an EP$_4$ receptor antagonist alone is not sufficient of these examples. Also, when the combination of the present invention is used, the drugs can be administered at lower doses, and it is expected that side effects are reduced.

In an embodiment, the combination of the present invention can also be applied to the treatment of metastatic cancer or the inhibition of metastasis.

In an embodiment, the combination of the present invention inhibits recurrence.

In the present invention, the treatment means to cause at least one of reduction in the tumor size, inhibition (delay or stop) of the growth of a tumor, inhibition (delay or stop) of the metastasis of a tumor, inhibition (prevention or delay) of recurrence, and relief of one symptom or more related to cancer.

In an embodiment, the combination of the present invention is used for the treatment of Hodgkin's lymphoma, head and neck cancer, esophageal cancer, stomach cancer, colorectal cancer, hepatocellular carcinoma, biliary tract cancer, non-small cell lung cancer, small cell lung cancer, ovarian cancer, renal cancer, urothelial cancer, mesothelioma, malignant melanoma, glioblastoma, or blood cancer.

In an embodiment, the combination of the present invention is used for the treatment of Hodgkin's lymphoma, head and neck cancer, esophageal cancer, stomach cancer, colorectal cancer, hepatocellular carcinoma, biliary tract cancer, non-small cell lung cancer, small cell lung cancer, ovarian cancer, urothelial cancer, mesothelioma, glioblastoma, or blood cancer.

In an embodiment, the combination of the present invention is used for the treatment of stomach cancer, colorectal cancer, lung cancer, renal cancer, or malignant melanoma.

The combination administration of the combination of the present invention includes simultaneous administration of compounds in a same preparation or separate preparations and separate administration of compounds (for example, sequential administration).

In the present invention, the combination of the present invention may be used in combination with another drug (for example, known anticancer treatment) in order to (1) complement and/or enhance the therapeutic effect, (2) improve the kinetics/absorption and reduce the dose, and/or (3) reduce a side effect.

Unless otherwise defined, all the technical and scientific terms and all the abbreviations used in this specification have the meaning as normally understood by a person skilled in the art of the present invention.

The contents of all the patent documents and the non-patent documents and the contents of the reference documents explicitly cited in this specification are incorporated herein as a part of the specification.

EXAMPLE

Synthetic Examples

The present invention is described below in detail by way of Examples, but the present invention is not limited by the following descriptions.

The solvents in parentheses shown in connection with the separation in chromatography and with TLC represent the eluting solvents or developing solvents used. The proportions are volume ratios.

The solvents in parentheses shown in connection with NMR represent the solvents used for measurement.

The compound names used in this specification are based on the computer program ACD/Name (registered trademark) or the Chemdraw Ultra (version 12.0, Cambridge Soft), which generally generate chemical names according to IUPAC rules, or based on the IUPAC nomenclature.

Reference Example 1: 4-Methylenechromane

[Chem. 39]

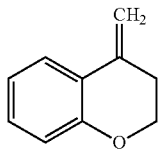

A solution of lithium bis(trimethylsilyl)amide in tetrahydrofuran (hereinafter, "THF") (1.3 mol/L, 931 mL) was dropped into a 1,500-mL THF solution of methyltriphenylphosphonium bromide (435 g) under a stream of nitrogen under ice-cooling, and the mixture was then stirred at room temperature for 1 h. The mixture was further stirred at room temperature for 1 h after dropping a 180-mL THF solution of 4-chromanone (150 g) at −5° C. After adding a saturated ammonium chloride aqueous solution to the reaction mixture under ice-cooling, the mixture was extracted with ethyl acetate. The resulting organic layer was washed with saturated brine, dried over anhydrous sodium sulfate and then concentrated under reduced pressure. The resulting residue was purified by silica gel column chromatography to obtain the title compound (75.9 g) having the following physical property values.

TLC: Rf 0.62 (hexane:ethyl acetate=9:1);
$^1$H-NMR (CDCl$_3$): δ 2.59-2.75, 4.18-4.31, 4.89, 5.51, 6.79-6.94, 7.12-7.20, 7.56.

Reference Example 2: Ethyl (2'R,4S)-2,3-dihydrospiro[chromene-4,1'-cyclopropane]-2'-carboxylate

[Chem. 40]

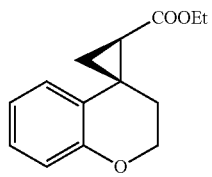

Under a stream of nitrogen, a dichloro(p-cymene)ruthenium(II) dimer (15.8 g) and (S,S)-2,6-bis(4-isopropyl-2-oxazolin-2-yl)pyridine (15.6 g) were added to a dichloromethane solution (2,500 mL) of the compound (75.9 g) produced in Reference Example 1. A dichloromethane solution (150 mL) of diazoethyl acetate (containing 13% of dichloromethane, 134 g) was slowly dropped at room temperature, and the mixture was then stirred for 1 h. After adding a saturated ammonium chloride aqueous solution to the reaction mixture, the mixture was extracted with dichloromethane, and the resulting organic layer was dried over anhydrous sodium sulfate and then concentrated under reduced pressure. The resulting residue was purified by silica gel column chromatography to obtain the title compound (91.2 g) having the following physical property values.

$^1$H-NMR (CDCl$_3$): δ 1.26, 1.54-1.67, 2.07-2.22, 4.05-4.21, 4.27, 6.68, 6.78-6.89, 7.04-7.12.

Reference Example 3: (2'R,4S)-2,3-Dihydrospiro[chromene-4,1'-cyclopropane]-2'-carboxylic acid

[Chem. 41]

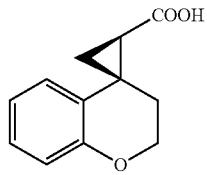

An aqueous solution (160 mL) of lithium hydroxide monohydrate (29.6 g) was added to a methanol (400 mL) and 1,2-dimethoxyethane (400 mL) solution of the compound (91.2 g) produced in Reference Example 2, and the mixture was stirred overnight at room temperature. A 10% aqueous solution of citric acid was added to the reaction mixture, and the mixture was then extracted with ethyl acetate. The resulting organic layer was washed with saturated brine, dried over anhydrous sodium sulfate and then concentrated under reduced pressure. The resulting residue was recrystallized with dichloromethane to obtain the title compound (55.2 g) having the following physical property values.

$^1$H-NMR (CDCl$_3$): δ 1.59-1.67, 1.68-1.76, 2.15, 2.21-2.29, 4.12-4.23, 4.25-4.36, 6.70, 6.80-6.92, 7.06-7.16;

HPLC retention time: 6.9 min (CHIRALPAK IC 4.6 mm×250 mm hexane:ethyl acetate:formic acid=97:3:1).

Reference Example 4: Methyl (2'R,4S)-2,3-dihydrospiro[chromene-4,1'-cyclopropane]-2'-carboxylate

[Chem. 42]

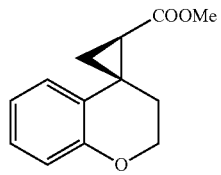

Under a stream of nitrogen, potassium carbonate (28.5 g) was added to an N,N-dimethylformamide (hereinafter, "DMF") solution (200 mL) of the compound (40.0 g) produced in Reference Example 3. Then, the mixture was stirred overnight at room temperature after dropping iodomethane (31.9 g). The reaction mixture was poured into ice water and extracted with a hexane-ethyl acetate mixed solution. The resulting organic layer was washed with water and saturated brine, dried over anhydrous sodium sulfate and then concentrated under reduced pressure to obtain the title compound (40.1 g) having the following physical property values.

TLC: Rf 0.30 (hexane:ethyl acetate=9:1);
$^1$H-NMR (CDCl$_3$): δ 1.57-1.69, 2.09-2.22, 3.71, 4.07-4.17, 4.27, 6.68, 6.78-6.90, 7.04-7.14.

Reference Example 5: Methyl (2'R,4S)-6-iodo-2,3-dihydrospiro[chromene-4,1'-cyclopropane]-2'-carboxylate

[Chem. 43]

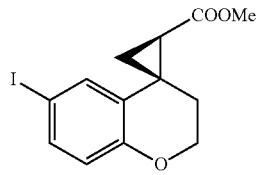

Under a stream of nitrogen, 1,3-diiodo-5,5-dimethylhydantoin (35.6 g) and three droplets of concentrated sulfuric acid were added to a methanol solution (320 mL) of the compound (40.1 g) produced in Reference Example 4, under ice-cooling. The mixture was then stirred for 1.5 h under the same condition and for 2.5 h at room temperature. The reaction mixture was diluted with a hexane-ethyl acetate mixed solution and then washed with a saturated sodium bicarbonate aqueous solution. The aqueous layer was subjected to extraction with a hexane-ethyl acetate mixed solution. The resulting organic layer was washed with water and saturated brine, dried over anhydrous sodium sulfate and then concentrated under reduced pressure to obtain the title compound (63.8 g) having the following physical property values.

TLC: Rf 0.33 (hexane:ethyl acetate=9:1);
$^1$H-NMR (CDCl$_3$): δ 1.60, 2.06-2.19, 3.71, 4.09, 4.20-4.31, 6.59, 6.93, 7.36.

Reference Example 6: (2'R,4S)-6-Iodo-2,3-dihydrospiro[chromene-4,1'-cyclopropane]-2'-carboxylic acid

[Chem. 44]

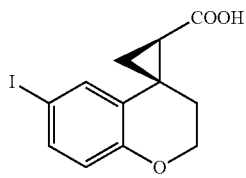

A sodium hydroxide aqueous solution (2 mol/L, 44 mL) was added to a methanol (60 mL) and 1,2-dimethoxyethane (60 mL) solution of the compound (15.0 g) produced in Reference Example 5, and the mixture was stirred at room temperature for 1.5 h. After adding hydrochloric acid to the reaction mixture, the mixture was extracted with ethyl acetate. The resulting organic layer was washed with water and saturated brine, dried over anhydrous sodium sulfate and then concentrated under reduced pressure to obtain the title compound (14.4 g) having the following physical property values.

TLC: Rf 0.42 (dichloromethane:methanol=9:1);
$^1$H-NMR (CDCl$_3$): δ 1.57-1.74, 2.11, 2.16-2.25, 4.10-4.20, 4.23-4.33, 6.59, 6.94, 7.37.

Reference Example 7: Ethyl 4-(4-formyl-2-nitrophenyl)butanoate

[Chem. 45]

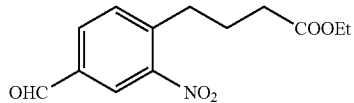

Iodine (26.0 g) was added to a 700-mL solution of a zinc powder (99.2 g) in N,N-dimethylacetamide (hereinafter, "DMA") under a stream of nitrogen, and the mixture was stirred for 10 min. After dropping ethyl 4-bromobutyrate (200 g), the mixture was stirred at 80° C. for 2 h to prepare a zinc reagent. Under a stream of nitrogen, 2-dicyclohexylphosphino-2',6'-dimethoxybiphenyl (7.14 g) and palladium acetate (1.96 g) were added to a 500-mL THF solution of 3-nitro-4-bromobenzaldehyde (100 g), and then the prepared zinc reagent (500 mL) was dropped into the mixture under ice-cooling. This was followed by stirring at room temperature for 30 min. A saturated ammonium chloride aqueous solution and water were added to the reaction mixture, and the mixture was then extracted with ethyl acetate. The resulting organic layer was washed with water and saturated brine, dried over anhydrous sodium sulfate and then concentrated under reduced pressure. The resulting residue was purified by silica gel column chromatography to obtain the title compound (91.2 g) having the following physical property values.

TLC: Rf 0.61 (hexane:ethyl acetate=2:1);

$^1$H-NMR (CDCl$_3$): δ 1.27, 1.97-2.09, 2.42, 3.01, 4.15, 7.57, 8.04, 8.38, 10.03.

Reference Example 8: Ethyl 4-(4-cyano-2-nitrophenyl)butanoate

[Chem. 46]

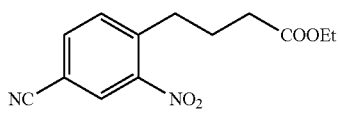

Hydroxylamine hydrochloride (26.0 g) was added to a 350-mL DMF solution of the compound (92.0 g) produced in Reference Example 7, and the mixture was stirred at 50° C. for 1 h. The mixture was stirred at 90° C. for 2 h after adding acetyl chloride (30 mL). Water was added to the reaction mixture, and then the mixture was extracted with ethyl acetate. The resulting organic layer was washed with water, a saturated sodium bicarbonate aqueous solution, and saturated brine, dried over anhydrous sodium sulfate and then concentrated under reduced pressure. The resulting residue was purified by silica gel column chromatography to obtain the title compound (81.0 g) having the following physical property values.

TLC: Rf 0.65 (hexane:ethyl acetate=2:1);

$^1$H-NMR (CDCl$_3$): δ 1.27, 1.92-2.10, 2.37-2.45, 2.91-3.06, 4.15, 7.55, 7.81, 8.21.

Reference Example 9: Ethyl 4-(2-amino-4-cyanophenyl)butanoate

[Chem. 47]

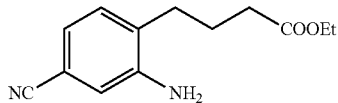

Palladium carbon (50% wet, 8.0 g) was added to an 80-mL ethanol solution of the compound (17.0 g) produced in Reference Example 8, and the mixture was stirred at room temperature for 9 h in a hydrogen atmosphere. After filtering the reaction mixture with Celite (trade name), the filtrate was concentrated to obtain the title compound (12.0 g) having the following physical property values.

TLC: Rf 0.56 (hexane:ethyl acetate=2:1);

$^1$H-NMR (CDCl$_3$): δ 1.28, 1.79-1.95, 2.38-2.45, 2.50-2.60, 4.09-4.30, 6.89, 6.93-6.98, 7.04-7.10.

Reference Example 10: Ethyl 4-[4-cyano-2-({[(2'R,4S)-6-iodo-2,3-dihydrospiro[chromene-4,1'-cyclopropan]-2'-yl]carbonyl}amino)phenyl]butanoate

[Chem. 48]

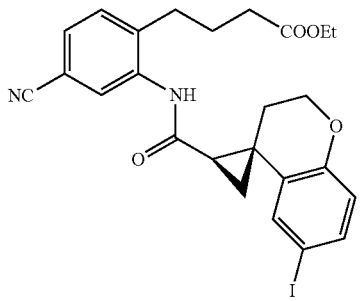

4-Methylmorpholine (24.0 mL), 4-dimethylaminopyridine (5.33 g), and a propylphosphonic acid anhydride cyclic trimer (hereinafter, "T3P"; 1.7 mol/L, 46.5 mL) were added to a 90-mL DMA solution of the compound (14.4 g) produced in Reference Example 6 and the compound (10.0 g) produced in Reference Example 9, and the mixture was stirred overnight at room temperature. Ethyl acetate, water, and a hydrochloric acid aqueous solution were added to the reaction mixture, and the mixture was extracted with ethyl acetate. The resulting organic layer was washed with water, a saturated sodium bicarbonate aqueous solution, and saturated brine, dried over anhydrous sodium sulfate and then concentrated under reduced pressure. The resulting residue was washed with a hexane-ethyl acetate mixed solution to obtain the title compound (19.3 g) having the following physical property values.

TLC: Rf 0.42 (hexane:ethyl acetate=2:1);

$^1$H-NMR (CDCl$_3$): δ 1.20, 1.61, 1.66-1.79, 1.83, 2.18-2.28, 2.39-2.49, 2.60, 3.66, 3.90, 4.00-4.12, 4.26, 6.58, 7.05, 7.15-7.22, 7.26-7.31, 7.33, 8.72, 9.39.

Reference Example 11: (2'R,4S)-2'-{[5-Cyano-2-(4-ethoxy-4-oxobutyl)phenyl]carbamoyl}-2,3-dihydrospiro[chromene-4,1'-cyclopropane]-6-carboxylic acid

[Chem. 49]

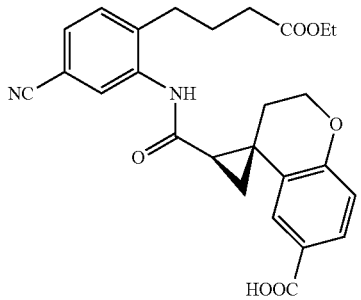

Sodium acetate (3.35 g) and a [1,1'-bis(diphenylphosphino)ferrocene]palladium(II) dichloride dichloromethane complex (555 mg) were added to a 60-mL DMF solution of the compound (7.40 g) produced in Reference Example 10, and the mixture was stirred at 80° C. for 6 h in a carbon monoxide atmosphere. A potassium carbonate aqueous solution was added to the reaction mixture, and the mixture was stirred for some time. Then, after adding tert-butyl methyl ether and water, the mixture was filtered with Celite (trade name). A hydrochloric acid aqueous solution was added to the filtrate, and then the mixture was extracted with ethyl acetate. The resulting organic layer was washed with water and saturated brine, dried over anhydrous sodium sulfate and then concentrated under reduced pressure. The resulting residue was purified by silica gel column chromatography (Yamazen Autopurification Device) to obtain the title compound (6.14 g) having the following physical property values.

TLC: Rf 0.48 (dichloromethane:ethyl acetate:methanol=8:4:1);

$^1$H-NMR (CDCl$_3$): δ 1.08, 1.65-1.80, 1.83-1.92, 2.25-2.36, 2.37-2.49, 2.55-2.66, 2.71, 3.55, 3.79, 4.12-4.23, 4.37, 6.88, 7.15-7.22, 7.27-7.32, 7.61, 7.83, 8.73, 9.40.

Reference Example 12: Ethyl 4-[4-cyano-2-({[(2'R,4S)-6-(methylcarbamoyl)-2,3-dihydrospiro[chromene-4,1'-cyclopropan]-2'-yl]carbonyl}amino)phenyl]butanoate

[Chem. 50]

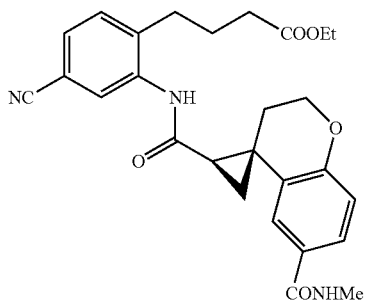

The title compound (53.0 mg) having the following physical property values was obtained by performing the same procedures as those of Reference Example 10, except that the compound (60.0 mg) produced in Reference Example 11 was used instead of the compound produced in Reference Example 6 and that methylamine hydrochloride (87.5 mg) was used instead of the compound produced in Reference Example 9.

$^1$H-NMR (CDCl$_3$): δ 1.07, 1.64-1.79, 1.81-1.89, 2.20-2.35, 2.40, 2.60, 2.69, 2.98, 3.44-3.59, 3.68-3.83, 4.07-4.19, 4.27-4.38, 6.05, 6.82, 7.15-7.22, 7.27-7.32, 7.35-7.44, 8.72, 9.37.

Example 1: 4-[4-cyano-2-({[(2'R,4S)-6-(methylcarbamoyl)-2,3-dihydrospiro[chromene-4,1'-cyclopropan]-2'-yl]carbonyl}amino)phenyl]butanoic acid

[Chem. 51]

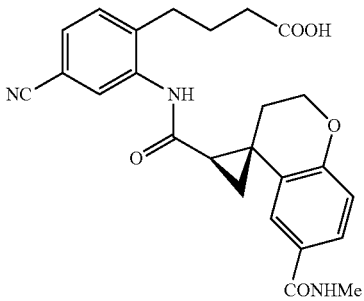

The title compound (45 mg) having the physical property values below was obtained by performing the same procedures as those of Reference Example 6 using the compound (53 mg) produced in Reference Example 12, using ethanol instead of methanol.

TLC: Rf 0.45 (dichloromethane:methanol=9:1);

$^1$H-NMR (CDCl$_3$): δ 1.21-1.30, 1.55, 1.65-1.82, 2.06-2.26, 2.38-2.67, 2.67-2.76, 3.02, 3.57, 4.33, 4.49-4.58, 6.25, 6.81, 7.19, 7.23-7.30, 7.94, 8.87, 9.93.

Example 2

The title compounds having the following physical property values were obtained by performing the same procedures as those of Reference Example 12→Example 1, except that the methylamine hydrochloride was replaced with a corresponding amine compound.

Example 2-1: 4-{4-cyano-2-[({(2'R,4S)-6-[(cyclopropylmethyl)carbamoyl-2,3-dihydrospiro[chromene-4,1'-cyclopropan]-2'-yl}carbonyl)amino]phenyl}butanoic acid

[Chem. 52]

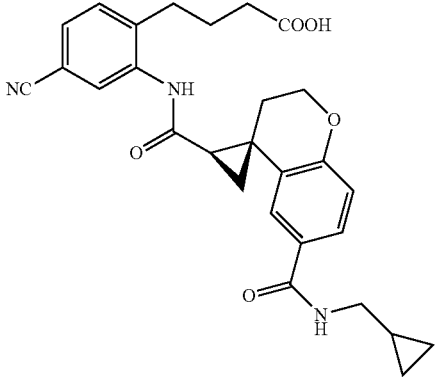

TLC: Rf 0.45 (dichloromethane:methanol=9:1);

$^1$H-NMR (CDCl$_3$): δ 0.23-0.31, 0.52-0.63, 0.96-1.14, 1.22-1.30, 1.55, 1.66-1.81, 2.06-2.24, 2.38-2.66, 2.66-2.76, 3.31, 3.57, 4.34, 4.49-4.59, 6.31, 6.83, 7.19, 7.24-7.29, 7.32, 7.95, 8.87, 9.93.

Example 2-2: 4-{4-cyano-2-[({(2'R,4S)-6-[(2-methoxyethyl}carbamoyl-2,3-dihydrospiro[chromene-4,1'-cyclopropan]-2'-yl}carbonyl)amino]phenyl}butanoic acid

[Chem. 53]

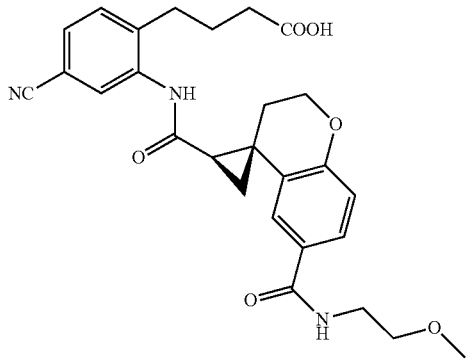

TLC: Rf 0.51 (dichloromethane:methanol=9:1);
¹H-NMR (CDCl₃): δ 1.26, 1.55, 1.67-1.84, 2.06-2.27, 2.39-2.67, 2.67-2.78, 3.39, 3.51-3.78, 4.33, 4.49-4.59, 6.62, 6.82, 7.19, 7.24-7.29, 7.32, 7.92, 8.86, 9.88.

Example 2-3: 4-[4-cyano-2-({(2'R,4S)-6-[(2-methyl-2-propanyl)carbamoyl]-2,3-dihydrospiro[chromene-4,1'-cyclopropan]-2'-yl}carbonyl)amino]phenyl}butanoic acid

[Chem. 54]

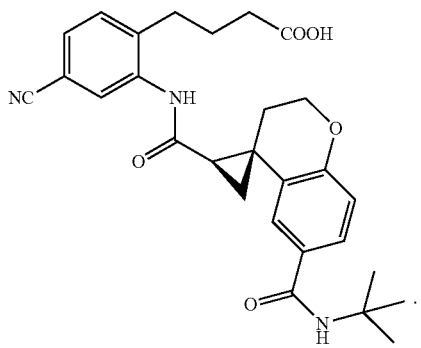

TLC: Rf 0.63 (chloroform:methanol=19:1);
¹H-NMR (DMSO-d₆): δ 1.37, 1.57, 1.64-1.85, 2.04-2.25, 2.42-2.48, 2.60-2.71, 4.01-4.15, 4.24-4.38, 6.80, 7.34-7.45, 7.52-7.66, 7.88, 9.89, 12.11.

Example 2-4: 4-[4-cyano-2-({[(2'R,4S)-6-{((2S)-1-methoxy-2-propanyl]carbamoyl}-2,3-dihydrospiro[chromene-4,1'-cyclopropan}-2'-yl]carbonyl}amino)phenyl]butanoic acid

[Chem. 55]

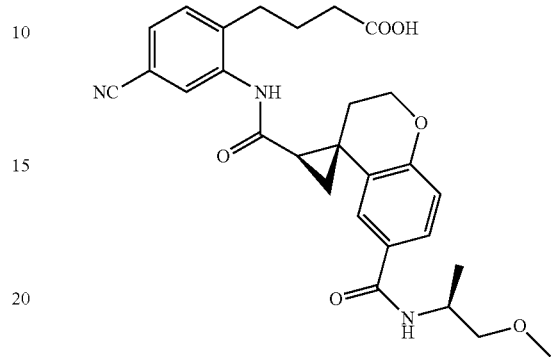

TLC: Rf 0.62 (ethyl acetate:methanol=19:1);
¹H-NMR (CD3OD): δ 1.22, 1.65-1.89, 2.12-2.26, 2.33, 2.62-2.77, 3.30-3.32, 3.37, 3.41, 3.47, 4.21-4.39, 6.82, 7.37-7.51, 7.58, 8.05.

Example 2-5: 4-{4-cyano-2-[((2'R,4S)-6-[(1-methyl-1H-pyrazol-4-yl)carbamoyl]-2,3-dihydrospiro[chromene-4,1'-cyclopropan]-2'-yl}carbonyl)amino]phenyl}butanoic acid TLC: Rf 0.51 (chloroform:methanol=9:1);
¹H-NMR (DMSO-d₆): δ 1.61, 1.66-1.87, 2.08-2.25, 2.50, 2.59-2.73, 3.81, 4.06-4.19, 4.28-4.42, 6.90, 7.41, 7.49-7.61, 7.73, 7.88, 7.99, 9.91, 10.19, 12.10.

Example 2-6: 4-{4-cyano-2-[({(2'R,4S)-6-[(3-methoxy-1-azetidinyl)carbamoyl]-2,3-dihydrospiro[chromene-4,1'-cyclopropan]-2'-yl}carbonyl)amino]phenyl}butanoic acid TLC: Rf 0.54 (ethyl acetate:methanol=19:1);
¹H-NMR (DMSO-d₆): δ 1.56, 1.67-1.80, 2.04-2.26, 2.45, 2.58-2.72, 3.21, 3.74-3.91, 4.06-4.27, 4.30, 4.37-4.51, 6.83, 7.15, 7.34-7.44, 7.57, 7.88, 9.89, 12.11.

Example 2-7: 4-{4-cyano-2-[({(2'R,4S)-6-[(1,3-oxazol-2-ylmethyl)carbamoyl]-2,3-dihydrospiro[chromene-4,1'-cyclopropan]-2'-yl}carbonyl)amino]phenyl}butanoic acid TLC: Rf 0.64 (chloroform:methanol=9:1);
¹H-NMR (DMSO-d₆): δ 1.53-1.63, 1.65-1.83, 2.07-2.25, 2.48, 2.58-2.70, 4.03-4.16, 4.27-4.40, 4.47-4.64, 6.87, 7.15, 7.40, 7.48, 7.56, 7.67, 7.87, 8.04, 9.02, 9.90, 12.10.

Example 2-8: 4-[4-cyano-2-({[(2'R,4S)-6-(1,3-oxazol-2-ylcarbamoyl)-2,3-dihydrospiro[chromene-4,1'-cyclopropan]-2'-yl]carbonyl}amino)phenyl]butanoic acid TLC: Rf 0.40 (chloroform:methanol=9:1);
¹H-NMR (DMSO-d₆): δ 1.61, 1.66-1.80, 1.86, 2.11-2.25, 2.52, 2.61-2.72, 4.14, 4.38, 6.93, 7.19, 7.42, 7.54-7.65, 7.76, 7.88, 7.96, 9.92, 11.38, 12.10.

Example 2-9: 4-{4-cyano-2-[({(2'R,4S)-6-[(1-methyl-1H-pyrazol-3-yl)carbamoyl]-2,3-dihydrospiro[chromene-4,1'-cyclopropan]-2'-yl}carbonyl)aminophenyl}butanoic acid

[Chem. 56]

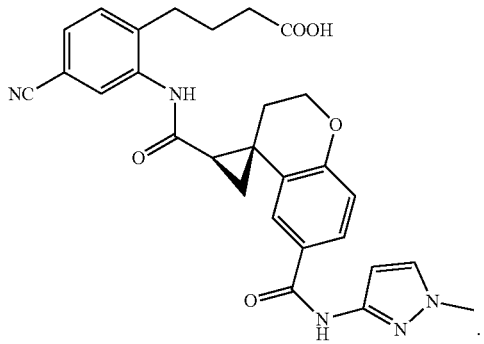

TLC: Rf 0.62 (chloroform:methanol=9:1);

$^1$H-NMR (DMSO-d$_6$): δ 1.59, 1.67-1.81, 1.92, 2.10-2.25, 2.54, 2.60-2.72, 3.77, 4.12, 4.35, 6.59, 6.89, 7.42, 7.55-7.62, 7.68, 7.77, 7.88, 9.92, 10.75, 12.10.

Example 2-10: 4-[4-cyano-2-({[(2'R,4S)-6-(cyclopropylcarbamoyl)-2,3-dihydrospiro[chromene-4,1'-cyclopropan]-2'-yl]carbonyl}amino)phenyl]butanoic acid

[Chem. 57]

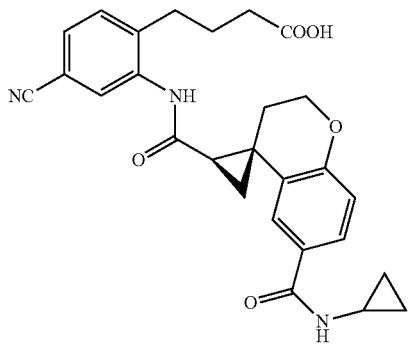

TLC: Rf 0.65 (ethyl acetate:methanol=19:1);

$^1$H-NMR (DMSO-d$_6$): δ 0.49-0.59, 0.65-0.75, 1.58, 1.66-1.82, 2.06-2.26, 2.47, 2.61-2.71, 2.81, 4.09, 4.34, 6.83, 7.36-7.45, 7.54-7.65, 7.88, 8.30, 9.89, 12.09.

Example 2-11: 4-[2-({[(2'R,4S)-6-(butylcarbamoyl)-2,3-dihydrospiro[chromene-4,1'-cyclopropan]-2'-yl]carbonyl}amino)-4-cyanophenyl]butanoic acid TLC: Rf 0.79 (ethyl acetate:methanol=19:1);

$^1$H-NMR (CDCl$_3$): δ 0.93-1.00, 1.21-1.83, 2.06-2.25, 2.37-2.77, 3.41-3.50, 3.51-3.63, 4.33, 4.54, 6.18, 6.81, 7.15-7.31, 7.94, 8.87, 9.93.

Example 2-12: 4-[4-cyano-2-({[(2'R,4S)-6-(cyclohexylcarbamoyl)-2,3-dihydrospiro[chromene-4,1'-cyclopropan-2'-yl]carbonyl}amino)phenyl]butanoic acid TLC: Rf 0.86 (ethyl acetate:methanol=19:1);

$^1$H-NMR (CDCl$_3$): δ 1.10-1.87, 1.94-2.26, 2.38-2.79, 3.50-3.64, 3.85-4.04, 4.33, 4.54, 6.04, 6.81, 7.14-7.31, 7.93, 8.87, 9.93.

Example 2-13: 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid

[Chem. 58]

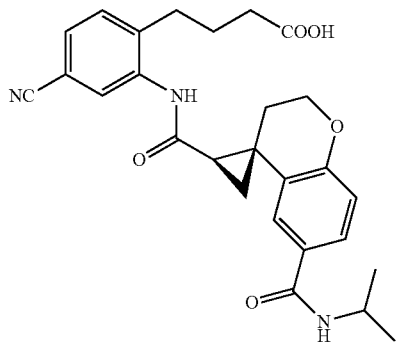

TLC: Rf 0.74 (ethyl acetate:methanol=19:1);

$^1$H-NMR (CDCl$_3$): δ 1.27, 1.34-1.92, 2.01-2.30, 2.38-2.80, 3.50-3.61, 4.18-4.43, 4.54, 6.00, 6.81, 7.15-7.31, 7.94, 8.87, 9.93.

Example 2-14: 4-[4-cyano-2-({[(2'R,4S)-6-(cyclopentylcarbamoyl)-2,3-dihydrospiro[chromene-4,1'-cyclopropan]-2'-yl]carbonyl}amino)phenyl]butanoic acid

[Chem. 59]

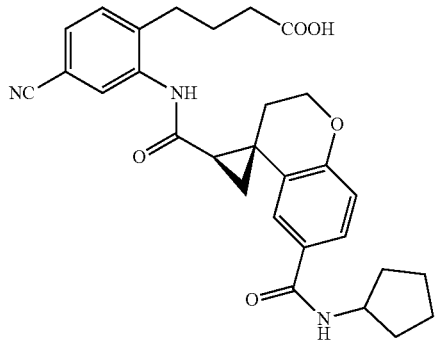

TLC: Rf 0.83 (ethyl acetate:methanol=19:1);

$^1$H-NMR (CDCl$_3$): δ 1.20-1.86, 2.00-2.26, 2.38-2.79, 3.50-3.64, 4.25-4.45, 4.46-4.61, 6.13, 6.81, 7.13-7.31, 7.94, 8.87, 9.93.

Example 2-15: 4-[4-cyano-2-({[(2'R,4S)-6-(isobutylcarbamoyl)-2,3-dihydrospiro[chromene-4,1'-cyclopropan]-2'-yl]carbonyl}amino)phenyl]butanoic acid TLC: Rf 0.83 (ethyl acetate:methanol=19:1);
$^1$H-NMR (CDCl$_3$): δ 0.84-1.03, 1.21-2.01, 2.06-2.26, 2.37-2.79, 3.20-3.38, 3.51-3.62, 4.34, 4.49-4.59, 6.18-6.32, 6.82, 7.14-7.32, 7.94, 8.87, 9.93.

Example 2-16: 4-{2-[({(2'R,4S)-6-[(2S)-2-butanylcarbamoyl]-2,3-dihydrospiro[chromene-4,1'-cyclopropan]-2'-yl}carbonyl)amino]-4-cyanophenyl}butanoic acid

[Chem. 60]

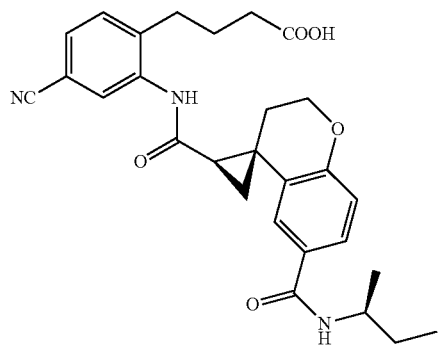

TLC: Rf 0.84 (ethyl acetate:methanol=20:1);
$^1$H-NMR (CDCl$_3$): δ 0.95, 1.18-1.91, 2.05-2.25, 2.39-2.78, 3.50-3.64, 4.03-4.20, 4.33, 4.48-4.60, 5.97, 6.81, 7.13-7.32, 7.94, 8.87, 9.93.

Example 2-17: 4-{2-[({(2'R,4S)-6-[(2R)-2-butanylcarbamoyl]-2,3-dihydrospiro[chromene-4,1'-cyclopropan]-2'-yl}carbonyl)amino]-4-cyanophenyl}butanoic acid TLC: Rf 0.84 (ethyl acetate:methanol=20:1);
$^1$H-NMR (CDCl$_3$): δ 0.98, 1.18-1.32, 1.49-1.86, 2.05-2.25, 2.39-2.81, 3.57, 4.11, 4.33, 4.54, 5.95, 6.81, 7.13-7.33, 7.93, 8.81, 8.86, 9.93.

Example 2-18: 4-[2-([(2'R,4S)-6-(benzylcarbamoyl)-2,3-dihydrospiro[chromene-4,1'-cyclopropan]-2'-yl]carbonyl}amino)-4-cyanophenyl]butanoic acid TLC: Rf 0.84 (ethyl acetate:methanol=20:1); 1H-NMR (CDCl$_3$): δ 1.20-1.86, 2.06-2.26, 2.40-2.79, 3.58, 4.34, 4.48-4.72, 6.47, 6.80, 7.15-7.42, 7.99, 8.87, 9.92.

Example 2-19: 4-{4-cyano-2-[((2'R,4S)-6-[(3R)-tetrahydro-3-furanylcarbamoyl]-2,3-dihydrospiro[chromene-4,1'-cyclopropan]-2'-yl}carbonyl)amino]phenyl}butanoic acid TLC: Rf 0.56 (ethyl acetate:methanol=19:1);
$^1$H-NMR (DMSO-d$_6$): δ 1.59, 1.67-1.83, 1.90, 2.07-2.26, 2.46, 2.61-2.71, 3.58, 3.72, 3.82-3.92, 4.10, 4.33, 4.48, 6.85, 7.38-7.48, 7.58, 7.67, 7.88, 8.39, 9.91, 12.11.

Example 2-20: 4-{4-cyano-2-[({(2'R,4S)-6-[(trans-4-hydroxycyclohexyl)carbamoyl]-2,3-dihydrospiro[chromene-4,1'-cyclopropan]-2'-yl}carbonyl)amino]phenyl}butanoic acid

[Chem. 61]

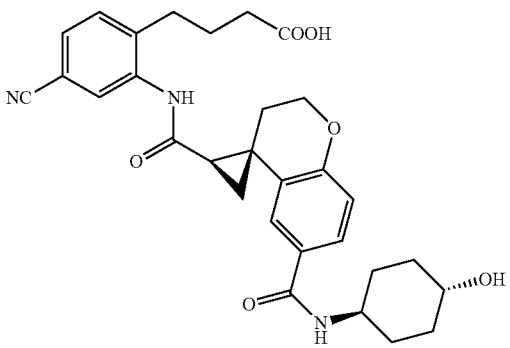

TLC: Rf 0.57 (ethyl acetate:methanol=9:1);
$^1$H-NMR (CDCl$_3$): δ 0.77-1.85, 1.95-2.26, 2.38-2.77, 3.48-3.77, 3.83-4.04, 4.33, 4.54, 5.97, 6.81, 7.15-7.35, 7.92, 8.87, 9.92.

Example 2-21: 4-{4-cyano-2-[({(2'R,4S)-6-[(cis-4-hydroxycyclohexyl)carbamoyl]-2,3-dihydrospiro[chromene-4,1'-cyclopropan]-2'-yl}carbonyl)amino]phenyl}butanoic acid

[Chem. 62]

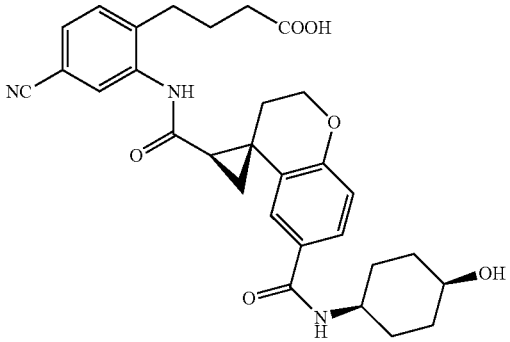

TLC: Rf 0.64 (ethyl acetate:methanol=9:1);
$^1$H-NMR (CDCl$_3$): δ 1.20-1.31, 1.51-1.86, 2.05-2.24, 2.38-2.79, 3.51-3.62, 3.94-4.09, 4.33, 4.54, 6.16, 6.82, 7.13-7.31, 7.92, 8.87, 9.92.

Example 2-22: 4-[4-cyano-2-(I [(2'R,4S)-6-[2-(dimethylamino)ethyl]carbamoyl]-2,3-dihydrospiro[chromene-4,1'-cyclopropan]-2'-yl]carbonyl}amino)phenyl]butanoic acid TLC: Rf 0.17 (ethyl acetate:methanol=9:1, Chromatorex diol TLC plate (Fuji Silysia Chemical Ltd.));
$^1$H-NMR (CDCl$_3$): δ 1.19-1.34, 1.59, 1.66-1.84, 2.09-3.16, 3.38, 3.62-3.81, 4.33, 4.52, 6.85, 7.15-7.31, 7.52-7.64, 7.87, 8.80, 9.55.

Example 2-23: 4-[4-cyano-2-({[(2'R,4S)-6-(2-pyridinylcarbamoyl)-2,3-dihydrospiro[chromene-4,1'-cyclopropan]-2'-yl]carbonyl}amino)phenyl]butanoic acid

[Chem. 63]

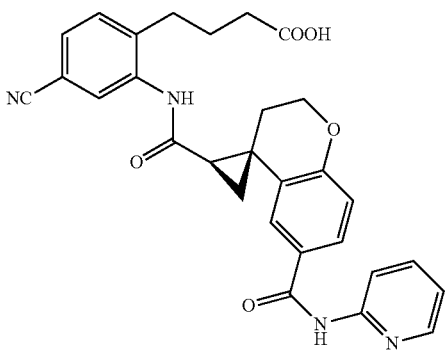

TLC: Rf 0.83 (ethyl acetate:methanol=19:1);
¹H-NMR (DMSO-$d_6$): δ 1.58, 1.73, 1.88-1.99, 2.10-2.24, 2.60-2.70, 4.06-4.18, 4.30-4.40, 6.90, 7.14, 7.41, 7.57, 7.72, 7.77-7.90, 8.18, 8.38, 9.91, 10.78, 12.09.

Example 2-24: 4-{4-cyano-2-[({(2'R,4S)-6-[(2-pyridinylmethyl)carbamoyl]-2,3-dihydrospiro[chromene-4,1'-cyclopropan]-2'-yl}carbonyl}amino]phenylbutanoic acid TLC: Rf 0.62 (ethyl acetate:methanol=9:1);
¹H-NMR (DMSO-$d_6$): δ 1.58, 1.63-1.84, 2.01-2.24, 2.59-2.69, 4.04-4.16, 4.27-4.39, 4.55, 6.87, 7.22-7.33, 7.40, 7.55, 7.66-7.80, 7.87, 8.45-8.55, 9.01, 9.90, 12.09.

Example 2-25: 4-[4-cyano-2-({[(2'R,4S)-6-{[(2R)-1-methoxy-2-propanyl]carbamoyl}-2,3-dihydrospiro[chromene-4,1'-cyclopropan]-2'-yl]carbonyl}amino)phenylbutanoic acid TLC: Rf 0.76 (ethyl acetate:methanol=19:1);
¹H-NMR (DMSO-$d_6$): δ 1.12, 1.59, 1.67-1.83, 2.08-2.25, 2.47, 2.61-2.70, 3.23-3.31, 3.40, 4.09, 4.20, 4.33, 6.85, 7.39-7.46, 7.58, 7.65, 7.89, 8.09, 9.90, 12.11.

Example 2-26: 4-[4-cyano-2-[((2'R,4S)-6-[(3-oxetanylmethyl)carbamoyl]-2,3-dihydrospiro[chromene-4,1'-cyclopropan]-2'-yl}carbonyl)amino]phenyl}butanoic acid TLC: Rf 0.56 (chloroform:methanol=9:1);
¹H-NMR (DMSO-$d_6$): δ 1.59, 1.66-1.80, 2.09-2.25, 2.46, 2.61-2.71, 3.15, 3.52, 4.10, 4.28-4.39, 4.63, 6.85, 7.37-7.47, 7.57-7.64, 7.89, 8.50, 9.92, 12.10.

Example 2-27: 4-{4-cyano-2-f[((2'R,4S)-6-[(3S)-tetrahydro-3-furanylcarbamoyl]-2,3-dihydrospiro[chromene-4,1'-cyclopropan]-2'-yl}carbonyl)amino]phenyl}butanoic acid TLC: Rf 0.50 (ethyl acetate:methanol=19:1);
¹H-NMR (DMSO-$d_6$): δ 1.51-1.63, 1.64-1.97, 2.04-2.28, 2.41-2.47, 2.60-2.70, 3.58, 3.64-3.77, 3.80-3.92, 4.02-4.16, 4.26-4.38, 4.38-4.53, 6.84, 7.36-7.48, 7.58, 7.67, 7.87, 8.37, 9.91, 12.10.

Example 2-28: 4-{4-cyano-2-[({(2'R,4S)-6-[(cyclobutylmethyl)carbamoyl]-2,3-dihydrospiro[chromene-4,1'-cyclopropan]-2'-yl}carbonyl)amino]phenyl}butanoic acid TLC: Rf 0.63 (dichloromethane:methanol=9:1);
¹H-NMR (DMSO-$d_6$): δ 1.52-1.62, 1.62-1.88, 1.88-2.06, 2.06-2.24, 2.60-2.70, 3.23-3.30, 4.01-4.14, 4.26-4.37, 6.83, 7.36-7.45, 7.59, 7.88, 8.31, 9.91, 12.10.

Example 2-29: 4-[4-cyano-2-({[(2'R,4S)-6-(3-pyridazinylcarbamoyl)-2,3-dihydrospiro[chromene-4,1'-cyclopropan]-2'-yl]carbonyl}amino)phenyl]butanoic acid

[Chem. 64]

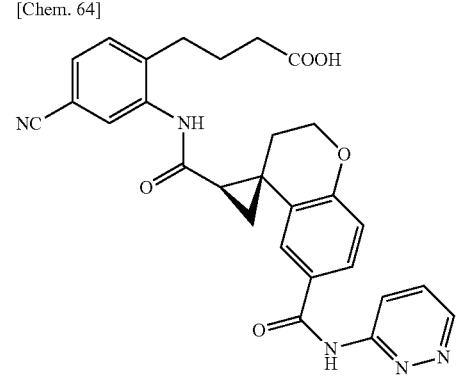

TLC: Rf 0.65 (dichloromethane:methanol=9:1);
¹H-NMR (DMSO-$d_6$): δ 1.59, 1.72, 1.87-1.99, 2.05-2.24, 2.54-2.70, 4.05-4.23, 4.30-4.44, 6.93, 7.41, 7.57, 7.72, 7.76-7.93, 8.38, 9.00, 9.99, 11.45, 12.11.

Example 2-30: 4-{4-cyano-2-[({(2'R,4S)-6-[(1-methyl-4-piperidinyl)carbamoyl]-2,3-dihydrospiro[chromene-4,1'-cyclopropan]-2'-yl}carbonyl)amino]phenyl}butanoic acid TLC: Rf 0.21 (dichloromethane:methanol:28% ammonia water=4:1:0.1);
¹H-NMR (DMSO-$d_6$): δ 1.49-1.83, 1.90-2.06, 2.06-2.24, 2.65, 2.81, 3.73, 4.02-4.15, 4.26-4.37, 6.83, 7.37-7.46, 7.56, 7.63, 7.90, 8.14, 10.01.

Example 2-31: 4-[4-cyano-2-({[(2'R,4S)-6-(1H-pyrazol-4-ylcarbamoyl)-2,3-dihydrospiro[chromene-4,1'-cyclopropan]-2'-yl]carbonyl}amino)phenyl]butanoic acid TLC: Rf 0.45 (dichloromethane:methanol=9:1);
$^1$H-NMR (CD3OD): δ 1.65-1.90, 2.24, 2.35, 2.60-2.80, 4.20-4.42, 6.89, 7.39-7.50, 7.59, 7.70, 7.89, 8.03.

Example 2-32: 4-{4-cyano-2-[({(2'R,4S)-6-[(2,2-difluoroethyl)carbamoyl]-2,3-dihydrospiro[chromene-4,1'-cyclopropan]-2'-yl}carbonyl)amino]phenyl}butanoic acid TLC: Rf 0.76 (ethyl acetate:methanol=19:1);
$^1$H-NMR (DMSO-$d_6$): δ 1.53-1.81, 2.06-2.25, 2.41-2.47, 2.58-2.71, 3.55-3.78, 4.04-4.17, 4.25-4.40, 5.84-6.36, 6.87, 7.41, 7.48, 7.55, 7.67, 7.87, 8.73, 9.91, 12.10.

Example 2-33: 4-[4-cyano-2-((([(2'R,4S)-6-{[(3S)-1-methyl-3-pyrrolidinyl]carbamoyl}-2,3-dihydrospiro[chromene-4,1'-cyclopropan]-2'-yl]carbonyl}amino)phenyl]butanoic acid TLC: Rf 0.33 (dichloromethane:methanol=9:1);
$^1$H-NMR (DMSO-$d_6$): δ 1.50-1.59, 1.62-1.84, 2.06-2.23, 2.37, 2.64, 2.74-2.84, 4.14, 4.24-4.36, 4.45, 6.83, 7.35-7.48, 7.55, 7.63, 7.98, 8.45, 10.09.

Example 2-34: 4-[4-cyano-2-({[(2'R,4S)-6-(1,3-thiazol-2-ylcarbamoyl)-2,3-dihydrospiro[chromene-4,1'-cyclopropan]-2'-yl]carbonyl}amino)phenyl]butanoic acid TLC: Rf 0.68 (dichloromethane:methanol=9:1);
$^1$H-NMR (DMSO-$d_6$): δ 1.56-1.64, 1.65-1.81, 1.86-1.96, 2.10-2.24, 2.60-2.70, 4.07-4.19, 4.32-4.43, 6.94, 7.26, 7.41, 7.53-7.60, 7.79, 7.82-7.90, 9.92, 12.11, 12.53.

Example 2-35: 4-[4-cyano-2-({[(2'R,4S)-6-(3-pyridinylcarbamoyl)-2,3-dihydrospiro[chromene-4,1'-cyclopropan]-2'-yl]carbonyl}amino)phenyl]butanoic acid TLC: Rf 0.53 (dichloromethane:methanol=9:1);
$^1$H-NMR (DMSO-$d_6$): δ 1.58-1.65, 1.72, 1.83, 2.08-2.24, 2.61-2.70, 4.30-4.43, 6.94, 7.35-7.45, 7.57, 7.79, 7.88, 8.11-8.18, 8.30, 8.90, 9.93, 10.24, 12.09.

Example 2-36: 4-[4-cyano-2-({[(2'R,4S)-6-(2-pyrimidinylcarbamoyl)-2,3-dihydrospiro[chromene-4,1'-cyclopropan]-2'-yl]carbonyl}amino)phenyl]butanoic acid TLC: Rf 0.56 (dichloromethane:methanol=9:1);
$^1$H-NMR (DMSO-$d_6$): δ 1.53-1.63, 1.63-1.80, 1.84-1.95, 2.07-2.24, 2.60-2.70, 4.06-4.19, 4.29-4.43, 6.90, 7.24, 7.41, 7.57, 7.64, 7.75, 7.86, 8.72, 9.91, 10.94, 12.08.

Example 2-37: 4-[4-cyano-2-({[(2'R,4S)-6-(1,2-oxazol-3-ylcarbamoyl)-2,3-dihydrospiro[chromene-4,1'-cyclopropan]-2'-yl]carbonyl}amino)phenyl]butanoic acid TLC: Rf 0.65 (dichloromethane:methanol=9:1);
$^1$H-NMR (DMSO-$d_6$): δ 1.36-1.50, 1.62, 1.86-2.15, 2.53-2.68, 2.68-2.89, 4.19-4.37, 6.85, 6.91, 7.31-7.41, 7.41-7.49, 7.62, 7.79, 8.36, 8.75, 11.61, 12.62.

Example 2-38: 4-[4-cyano-2-({[(2'R,4S)-6-(cyclobutylcarbamoyl)-2,3-dihydrospiro[chromene-4,1'-cyclopropan]-2'-yl]carbonyl}amino)phenyl]butanoic acid

[Chem. 65]

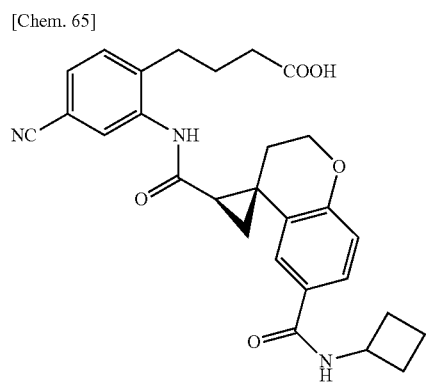

TLC: Rf 0.72 (ethyl acetate);
$^1$H-NMR (CD3OD): δ 1.62-1.90, 2.02-2.44, 2.59-2.80, 4.19-4.30, 4.33, 4.49, 6.82, 7.37-7.51, 7.58, 8.04.

Example 2-39: 4-[4-cyano-2-({[(2'R,4S)-6-{[1-(2-methyl-2-propanyl)-1H-pyrazol-4-yl]carbamoyl}-2,3-dihydrospiro[chromene-4,1'-cyclopropan]-2'-yl]carbonyl}amino)phenyl]butanoic acid

[Chem. 66]

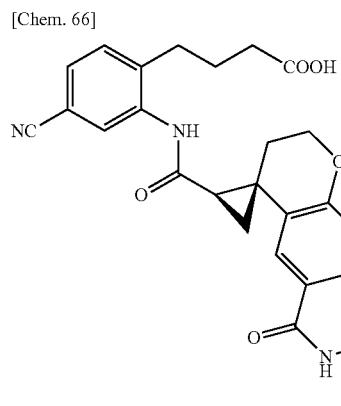

TLC: Rf 0.64 (ethyl acetate);
$^1$H-NMR (CD$_3$OD): δ 1.59, 1.67-1.92, 2.16-2.29, 2.30-2.41, 2.62-2.78, 4.21-4.32, 4.33-4.46, 6.88, 7.37-7.51, 7.58, 7.65-7.74, 8.03, 8.11.

Example 2-40: 4-[4-cyano-2-({[(2'R,4S)-6-(tetrahydro-2H-pyran-4-ylcarbamoyl)-2,3-dihydrospiro[chromene-4,1'-cyclopropan]-2'-yl]carbonyl}amino)phenyl]butanoic acid

[Chem. 67]

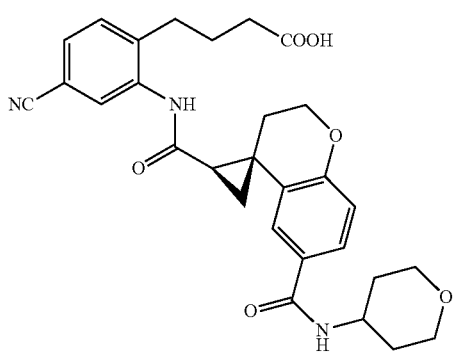

TLC: Rf 0.62 (ethyl acetate:methanol=9:1);

¹H-NMR (DMSO-d$_6$): δ 1.44-1.86, 2.02-2.24, 2.59-2.70, 3.35-3.44, 3.80-4.15, 4.25-4.37, 6.84, 7.37-7.46, 7.57, 7.64, 7.87, 8.13, 9.90, 12.09.

Example 2-41: 4-[4-cyano-2-({[(2'R,4S)-6-(1,2-oxazol-5-ylcarbamoyl)-2,3-dihydrospiro[chromene-4,1'-cyclopropan]-2'-yl]carbonyl}amino)phenyl]butanoic acid TLC: Rf 0.71 (ethyl acetate:methanol=9:1);

¹H-NMR (DMSO-ds): δ 1.56-1.66, 1.73, 1.87, 2.06-2.25, 2.60-2.70, 4.06-4.19, 4.31-4.44, 6.39, 6.94, 7.41, 7.57, 7.67, 7.81, 7.87, 8.50, 9.92, 11.90, 12.09.

Example 2-42: 4-[4-cyano-2-({[(2'R,4S)-6-(4-pyridinylcarbamoyl)-2,3-dihydrospiro[chromene-4,1'-cyclopropan]-2'-yl]carbonyl}amino)phenyl]butanoic acid TLC: Rf 0.53 (dichloromethane:methanol=4:1);

¹H-NMR (DMSO-d$_6$): δ 1.57-1.66, 1.73, 1.83, 2.09-2.24, 2.60-2.70, 4.08-4.21, 4.31-4.42, 6.95, 7.41, 7.52-7.61, 7.74-7.91, 8.42-8.52, 9.91, 10.38, 12.09.

Example 2-43: 4-{4-cyano-2-[({2'R,4S)-6-[(1-methyl-1H-pyrazol-5-yl)carbamoyl]-2,3-dihydrospiro[chromene-4,1'-cyclopropan]-2'-yl}carbonyl)amino]phenyl}butanoic acid TLC: Rf 0.58 (chloroform:methanol=9:1);

¹H-NMR (DMSO-d$_6$): δ 1.55-1.65, 1.66-1.90, 2.06-2.29, 2.50, 2.60-2.74, 3.66, 4.06-4.22, 4.30-4.46, 6.17, 6.93, 7.35-7.45, 7.52-7.61, 7.77, 7.88, 9.91, 10.15, 12.10.

Example 2-44: 4-[4-cyano-2-({[(2'R,4S)-6-(propylcarbamoyl)-2,3-dihydrospiro r[chromene-4,1'-cyclopropan]-2'-yl]carbonyl}amino)phenyl]butanoic acid

[Chem. 68]

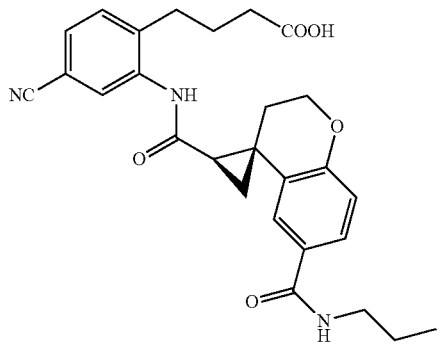

TLC: Rf 0.75 (ethyl acetate);

¹H-NMR (DMSO-d$_6$): δ 0.88, 1.45-1.63, 1.68-1.82, 2.07-2.25, 2.45, 2.61-2.72, 3.15-3.26, 4.10, 4.32, 6.85, 7.39-7.46, 7.57-7.63, 7.88, 8.32, 9.90, 12.11.

Example 2-45: 4-{4-cyano-2-[({(2'R,4S)-6-[(2-ethoxyethyl)carbamoyl]-2,3-dihydrospiro[chromene-4,1'-cyclopropan]-2'-yl}carbonyl)amino]phenyl}butanoic acid

[Chem. 69]

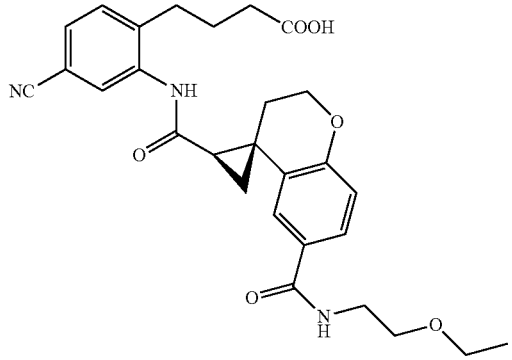

TLC: Rf 0.51 (ethyl acetate);

¹H-NMR (DMSO-d$_6$): δ 1.11, 1.59, 1.67-1.83, 2.07-2.26, 2.47, 2.61-2.71, 3.35-3.52, 4.10, 4.33, 6.85, 7.38-7.48, 7.57-7.64, 7.88, 8.42, 9.90, 12.09.

Example 2-46: 4-[4-cyano-2-({[(2'R,4S)-6-(ethyl-carbamoyl)-2,3-dihydrospiro[chromene-4,1'-cyclopropan]-2'-yl]carbonyl}amino)phenyl]butanoic acid

[Chem. 70]

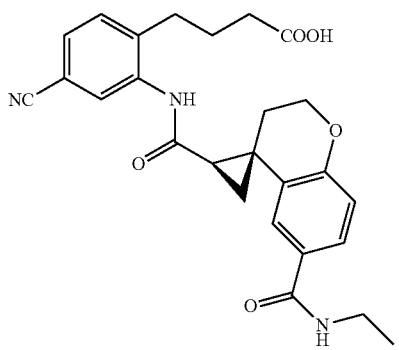

TLC: Rf 0.59 (ethyl acetate);
$^1$H-NMR (DMSO-d$_6$): δ 1.10, 1.58, 1.65-1.80, 2.07-2.24, 2.45, 2.58-2.69, 3.19-3.33, 4.09, 4.32, 6.84, 7.37-7.45, 7.57, 7.62, 7.88, 8.33, 9.89, 12.09.

Example 2-47: 4-{4-cyano-2-[({(2'R,4S)-6-[(1-methoxy-2-methyl-2-propanyl)carbamoyl]-2,3-dihydrospiro[chromene-4,1'-cyclopropan]-2'-yl}carbonyl)amino]phenyl}butanoic acid TLC: Rf 0.72 (hexane:ethyl acetate=1:3);
$^1$H-NMR (DMSO-d$_6$): δ 1.33, 1.57, 1.67-1.86, 2.08-2.25, 2.47, 2.62-2.71, 3.27, 3.53, 4.09, 4.32, 6.82, 7.35-7.45, 7.48, 7.57-7.62, 7.88, 9.89, 12.10.

Reference Example 13: Ethyl 4-[4-cyano-2-({[(2'R,4S)-6-(5-methyl-1,3,4-oxadiazol-2-yl)-2,3-dihydrospiro[chromene-4,1'-cyclopropan]-2'-yl]carbonyl}amino)phenyl]butanoate

[Chem. 71]

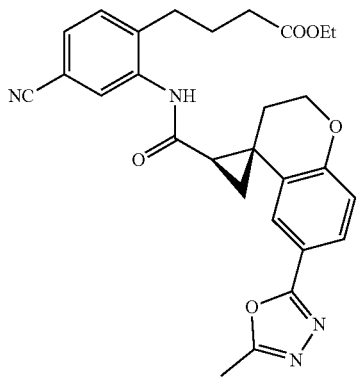

Triethylamine (60 μL) and T3P (a 1.7 mol/L ethyl acetate solution, 95 μL) were added at room temperature to a 0.5-mL dichloromethane solution of the compound (50 mg) produced in Reference Example 11 and acetylhydrazine (16 mg). The reaction mixture was stirred at room temperature for 1.5 h and then concentrated under reduced pressure. The Burgess reagent (Methyl N-(triethylammoniosulfonyl)carbamate, 117 mg) was added at room temperature to a 5-mL THF solution of the compound obtained by purifying the resulting residue by silica gel column chromatography (Yamazen Autopurification Device). The mixture was stirred at 100° C. for 1 h using a microwave reactor (Biotage, Ltd.). A saturated sodium bicarbonate aqueous solution was poured into the reaction mixture, and the mixture was extracted with ethyl acetate. The resulting organic layer was washed with saturated brine, dried over anhydrous magnesium sulfate and then concentrated under reduced pressure. The resulting residue was purified by silica gel column chromatography (Yamazen Autopurification Device) to obtain the title compound (22 mg) having the following physical property values.

TLC: Rf 0.53 (hexane:ethyl acetate=1:3);
$^1$H-NMR (CDCl$_3$): $0.94, 1.65-1.83, 1.89, 2.26-2.34, 2.35-2.44, 2.56-2.63, 2.66-2.76, 3.12-3.28, 3.36-3.55, 3.58-3.74, 4.07-4.23, 4.30-4.41, 6.92, 7.18, 7.28, 7.54, 7.70, 8.72, 9.39.

Example 3: 4-[4-cyano-2-({[(2'R,4S)-6-(5-methyl-1,3,4-oxadiazol-2-yl)-2,3-dihydrospiro[chromene-4,1'-cyclopropan]-2'-yl]carbonyl}amino)phenyl]butanoic acid

[Chem. 72]

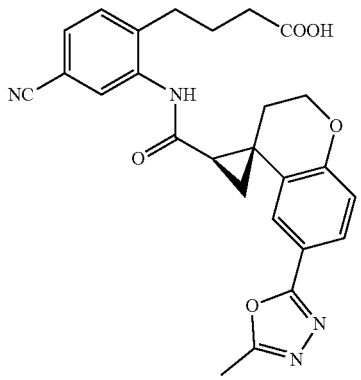

The title compound having the following physical property values was obtained by performing the same procedures as those of Example 1 using the compound produced in Reference Example 13, instead of the compound produced in Reference Example 12.

TLC: Rf 0.93 (dichloromethane:methanol=9:1);
$^1$H-NMR (CDCl$_3$): δ 1.27, 1.54, 1.70-1.91, 2.17, 2.32, 2.45-2.90, 3.64, 4.35-4.48, 4.56-4.66, 6.92, 7.20, 7.28, 7.58, 8.15, 8.92, 9.91, 12.68.

Example 4

The title compounds having the following physical property values were obtained by performing the same procedures as those of Reference Example 13→Example 1, except that the acetylhydrazine was replaced with a corresponding hydrazine compound.

Example 4-1: 4-[4-cyano-2-([(2'R,4S)-6-(5-cyclo-propyl-1,3,4-oxadiazol-2-yl)-2,3-dihydrospiro[chromene-4,1'-cyclopropan]-2'-yl]carbonyl}amino)phenyl]butanoic acid

[Chem. 73]

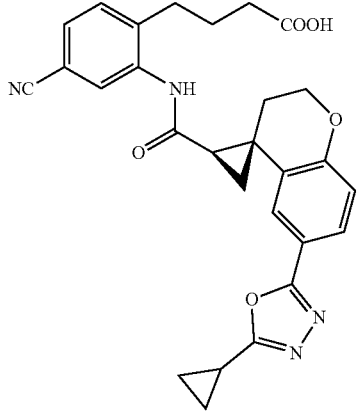

TLC: Rf 0.64 (ethyl acetate:methanol=19:1);
$^1$H-NMR (CDCl$_3$): δ 1.14-1.32, 1.78, 2.07-2.41, 2.43-2.91, 3.63, 4.33-4.49, 4.61, 6.86-6.96, 7.16-7.32, 7.54, 8.13, 8.92, 9.91.

Example 4-2: 4-{4-cyano-2-[({(2'R,4S)-6-[5-(2-methyl-2-propanyl)-1,3,4-oxadiazol-2-yl]-2,3-dihydrospiro[chromene-4,1'-cyclopropan]-2'-yl}carbonyl)amino]phenyl}butanoic acid TLC: Rf 0.83 (ethyl acetate:methanol=19:1);
$^1$H-NMR (CDCl$_3$): δ 1.19-1.32, 1.44-1.52, 1.64-1.87, 2.10-2.40, 2.44-2.90, 3.64, 4.35-4.49, 4.56-4.67, 6.93, 7.16-7.35, 7.60, 8.15, 8.92, 9.92.

Example 4-3: 4-[4-cyano-2-({[(2'R,4S)-6-(5-ethyl-1,3,4-oxadiazol-2-yl)-2,3-dihydrospiro[chromene-4,1'-cyclopropan]-2'-yl]carbonyl}amino)phenyl]butanoic acid TLC: Rf 0.53 (dichloromethane:methanol=9:1);
$^1$H-NMR (DMSO-d$_6$): δ 1.32, 1.60, 1.66-1.82, 2.10-2.24, 2.60-2.70, 2.92, 4.09-4.21, 4.31-4.42, 6.99, 7.41, 7.46, 7.57, 7.71, 7.88, 9.91, 12.08.

Reference Example 14: Ethyl 4-[4-cyano-2-({[(2'R,4S)-6-(3-methyl-1,2,4-oxadiazol-5-yl)-2,3-dihydrospiro[chromene-4,1'-cyclopropan]-2'-yl]carbonyl}amino)phenyl]butanoate

[Chem. 74]

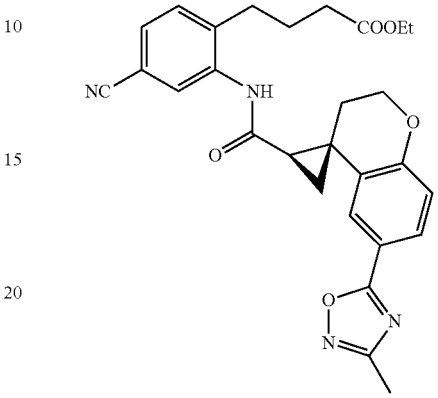

Triethylamine (0.144 mL) and T3P (a 1.7 mol/L ethyl acetate solution, 0.380 mL) were added at room temperature to a 0.5-mL ethyl acetate solution of the compound (80 mg) produced in Reference Example 11 and acetamideoxime (32 mg). The reaction mixture was heated under reflux for 4 days and then concentrated under reduced pressure. The resulting residue was purified by silica gel column chromatography (Yamazen Autopurification Device) to obtain the title compound (49 mg) having the following physical property values.
TLC: Rf 0.55 (hexane:ethyl acetate=1:1);
$^1$H-NMR (CDCl$_3$): δ 0.92, 1.64-1.83, 1.86-1.95, 2.22-2.35, 2.36-2.44, 2.45, 2.54-2.65, 2.72, 3.39-3.54, 3.59-3.73, 4.10-4.23, 4.32-4.44, 6.94, 7.20, 7.28, 7.59, 7.84, 8.74, 9.39.

Example 5: 4-[4-cyano-2-({[(2'R,4S)-6-(3-methyl-1,2,4-oxadiazol-5-yl)-2,3-dihydrospiro[chromene-4,1'-cyclopropan]-2'-yl]carbonyl}amino)phenyl]butanoic acid

[Chem. 75]

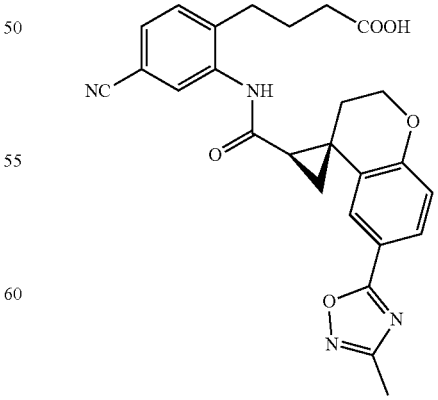

The title compound having the following physical property values was obtained by performing the same procedures as those of Example 1 using the compound produced in Reference Example 14, instead of the compound produced in Reference Example 12.

TLC: Rf 0.74 (ethyl acetate:methanol=20:1);

$^1$H-NMR (DMSO-d$_6$): δ 1.55-1.64, 1.67-1.83, 2.11-2.29, 2.39, 2.51-2.60, 2.61-2.73, 4.11-4.25, 4.31-4.44, 7.02, 7.41, 7.52-7.62, 7.83, 7.88, 9.90, 12.10.

Reference Example 15: Ethyl 4-[4-cyano-2-({[(2'R,4S)-6-(4-fluorophenyl)-2,3-dihydrospiro[chromene-4,1'-cyclopropan]-2'-yl]carbonyl}amino)phenyl]butanoate

[Chem. 76]

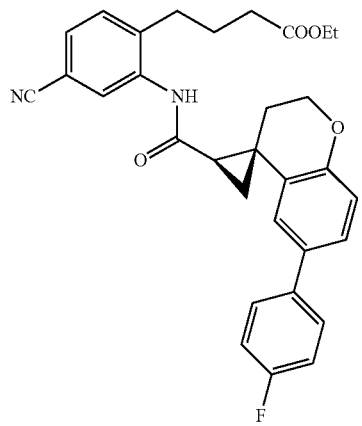

Cesium carbonate (84 mg), 4-fluorophenylboronic acid (36 mg), and purified water (0.4 mL) were added at room temperature to a 0.4-mL 1,2-dimethoxyethane solution of the compound (70 mg) produced in Reference Example 10, and the atmosphere was replaced with argon. A [1,1'-bis(diphenylphosphino)ferrocene]palladium(II) dichloride dichloromethane complex (5 mg) was added, and the mixture was stirred overnight at 85° C. The reaction mixture was diluted with ethyl acetate and then extracted with ethyl acetate after adding water. The resulting organic layer was washed with water and saturated brine, dried over anhydrous sodium sulfate and then concentrated under reduced pressure. The resulting residue was purified by silica gel column chromatography (Yamazen Autopurification Device) to obtain the title compound (54 mg) having the following physical property values.

TLC: Rf 0.48 (hexane:ethyl acetate=2:1);

$^1$H-NMR (CDCl$_3$): δ 0.83, 1.64-1.79, 1.82-1.93, 2.29, 2.33-2.43, 2.48-2.74, 3.30, 3.49, 4.06-4.19, 4.26-4.38, 6.84-6.91, 6.97, 7.04-7.15, 7.15-7.22, 7.22-7.32, 7.39-7.51, 8.73, 9.30.

Example 6: 4-[4-cyano-2-({[(2'R,4S)-6-(4-fluorophenyl)-2,3-dihydrospiro[chromene-4,1'-cyclopropan]-2'-yl]carbonyl}amino)phenyl]butanoic acid

[Chem. 77]

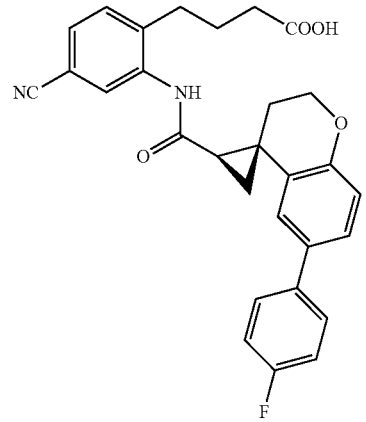

The title compound having the following physical property values was obtained by performing the same procedures as those of Example 1 using the compound produced in Reference Example 15, instead of the compound produced in Reference Example 12.

TLC: Rf 0.58 (dichloromethane:methanol=9:1);

$^1$H-NMR (DMSO-d$_6$): δ 1.50-1.60, 1.72, 1.87, 2.06-2.24, 2.60-2.69, 4.03-4.15, 4.24-4.35, 6.87, 7.11, 7.19-7.29, 7.32-7.44, 7.56, 7.61-7.70, 7.87, 9.88, 12.09.

Example 7

The title compounds having the following physical property values were obtained by performing the same procedures as those of Reference Example 15→Example 1, except that the 4-fluorophenylboronic acid was replaced with a corresponding boronic acid compound or a corresponding heterocyclic ring.

Example 7-1: 4-[4-cyano-2-({[(2'R,4S)-6-phenyl-2,3-dihydrospiro[chromene-4,1'-cyclopropan]-2'-yl]carbonyl}amino)phenyl]butanoic acid TLC: Rf 0.53 (dichloromethane:methanol=9:1)

$^1$H-NMR (CDCl$_3$): δ 1.58-1.81, 2.14-2.27, 2.36-2.46, 2.49-2.71, 2.78, 4.22-4.37, 6.92, 7.15, 7.16-7.22, 7.26-7.51, 7.52-7.61, 8.69, 8.95.

Example 7-2: 4-[4-cyano-2-({[(2'R,4S)-6-(4-pyridinyl)-2,3-dihydrospiro[chromene-4,1'-cyclopropan]-2'-yl]carbonyl}amino)phenyl]butanoic acid TLC: Rf 0.36 (dichloromethane:methanol=9:1);

$^1$H-NMR (DMSO-d$_6$): δ 1.52-1.63, 1.64-1.79, 1.87-1.99, 2.08-2.30, 2.43-2.73, 3.99-4.20, 4.25-4.41, 6.93, 7.31, 7.40, 7.56, 7.66-7.71, 7.87, 8.51-8.62, 9.88, 11.90-12.18.

Example 7-3: 4-[4-cyano-2-({[(2'R,4S)-6-(3-pyridinyl)-2,3-dihydrospiro[chromene-4,1'-cyclopropan]-2'-yl]carbonyl}amino)phenyl]butanoic acid

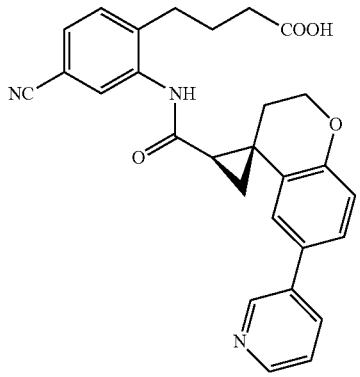

TLC: Rf 0.36 (dichloromethane:methanol=9:1);
$^1$H-NMR (DMSO-$d_6$): δ 1.56, 1.65-1.77, 1.88-2.00, 2.06-2.30, 2.34-2.75, 4.03-4.19, 4.25-4.39, 6.92, 7.22, 7.37-7.51, 7.57, 7.87, 7.99-8.09, 8.48-8.53, 8.87, 9.87.

Example 7-4: 4-[4-cyano-2-({[(2'R,4S)-6-(1H-pyrazol-1-yl)-2,3-dihydrospiro[chromene-4,1'-cyclopropan]-2'-yl]carbonyl}amino)phenyl]butanoic acid

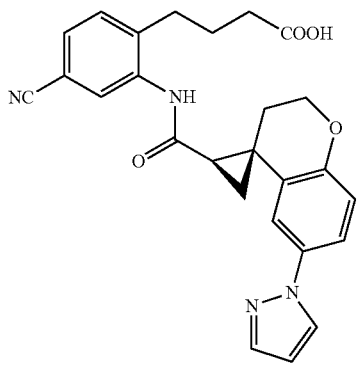

TLC: Rf 0.45 (dichloromethane:methanol=9:1);
$^1$H-NMR (CDCl$_3$): δ 1.23-1.34, 1.62, 1.66-1.83, 2.05-2.23, 2.40-2.59, 2.61-2.82, 3.37-3.47, 4.22-4.35, 4.44-4.52, 6.49, 6.88, 7.11, 7.20, 7.28, 7.41, 7.71, 8.86, 9.95.

Example 7-5: 4-[4-cyano-2-({[(2'R,4S)-6-(1H-pyrazol-5-yl)-2,3-dihydrospiro[chromene-4,1'-cyclopropan]-2'-yl]carbonyl}amino)phenyl]butanoic acid

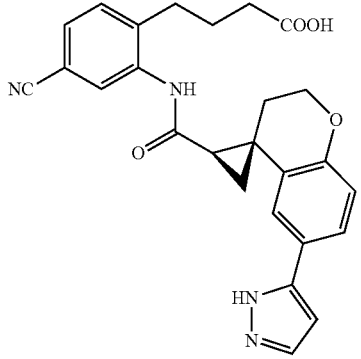

TLC: Rf 0.35 (dichloromethane:methanol=9:1);
$^1$H-NMR (DMSO-$d_6$): δ 1.51-1.62, 1.63-1.86, 2.04-2.33, 2.34-2.75, 3.98-4.14, 4.23-4.35, 6.65, 6.82, 7.29, 7.40, 7.48-7.60, 7.63, 7.87, 9.91, 12.47.

Example 7-6: 4-[4-cyano-2-({[(2'R,4S)-6-(4-pyridazinyl)-2,3-dihydrospiro[chromene-4,1'-cyclopropan]-2'-yl]carbonyl}amino)phenyl]butanoic acid

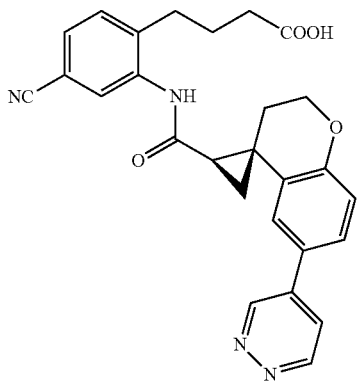

TLC: Rf 0.40 (dichloromethane:methanol=9:1);
$^1$H-NMR (DMSO-$d_6$): δ 1.53-1.62, 1.63-1.80, 1.95-2.06, 2.09-2.33, 2.34-2.78, 4.01-4.22, 4.28-4.42, 6.97, 7.42, 7.47, 7.57, 7.71, 7.87, 7.94-8.04, 9.20, 9.60, 9.87, 12.1.

Example 7-7: 4-[4-cyano-2-({[(2'R,4S)-6-(1-methyl-1H-pyrazol-4-yl)-2,3-dihydrospiro[chromene-4,1'-cyclopropan]-2'-yl]carbonyl}amino)phenyl]butanoic acid TLC: Rf 0.25 (ethyl acetate:methanol=19:1);
$^1$H-NMR (CDCl$_3$): δ 1.44-1.88, 2.22-2.33, 2.48, 2.58-2.76, 3.70, 4.16-4.36, 6.81-6.95, 7.11-7.34, 7.39, 7.56, 8.73, 9.16.

Example 7-8: 4-[4-cyano-2-({[(2'R,4S)-6-(5-pyrimidinyl)-2,3-dihydrospiro[chromene-4,1'-cyclopropan]-2'-yl]carbonyl}amino)phenyl]butanoic acid TLC: Rf 0.44 (dichloromethane:methanol=9:1);
$^1$H-NMR (DMSO-$d_6$): δ 1.57, 1.65-1.79, 1.92-2.03, 2.06-2.35, 2.36-2.77, 4.01-4.17, 4.27-4.40, 6.94, 7.33, 7.40, 7.50-7.61, 7.87, 9.12, 9.86, 12.08.

Example 7-9: 4-[4-cyano-2-({[(2'R,4S)-6-(2-thienyl)-2,3-dihydrospiro[chromene-4,1'-cyclopropan]-2'-yl]carbonyl}amino)phenyl]butanoic acid TLC: Rf 0.44 (dichloromethane:methanol=9:1);
$^1$H-NMR (DMSO-$d_6$): δ 1.51-1.61, 1.65-1.78, 1.79-1.88, 2.05-2.31, 2.40-2.76, 3.98-4.14, 4.23-4.36, 6.83, 7.04-7.16, 7.30-7.49, 7.57, 7.86, 9.90, 12.08.

Example 7-10: 4-[4-cyano-2-({[(2'R,4S)-6-(2-oxo-1-pyrrolidinyl)-2,3-dihydrospiro[chromene-4,1'-cyclopropan]-2'-yl]carbonyl}amino)phenyl]butanoic acid

[Chem. 82]

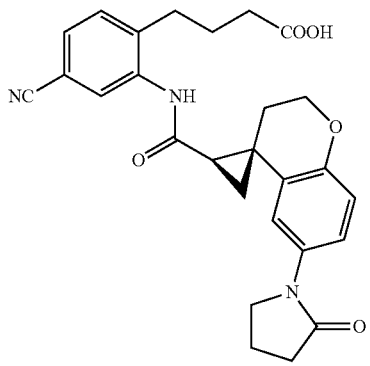

TLC: Rf 0.47 (dichloromethane:methanol=9:1);
$^1$H-NMR (DMSO-$d_6$): δ 1.50-1.59, 1.60-1.80, 1.93-2.12, 2.19, 2.31-2.51, 2.54-2.78, 3.78, 3.93-4.09, 4.19-4.31, 6.78, 7.09, 7.29, 7.40, 7.56, 7.85, 9.91, 12.08.

Example 7-11: 4-[4-cyano-2-({[(2'R,4S)-6-(1,3-thiazol-5-yl)-2,3-dihydrospiro[chromene-4,1'-cyclopropan]-2'-yl]carbonyl}amino)phenyl]butanoic acid TLC: Rf 0.53 (ethyl acetate:methanol=20:1);
$^1$H-NMR (CDCl$_3$): δ 1.20-1.30, 1.58, 1.73-1.90, 2.26-2.37, 2.52, 2.64-2.82, 4.19-4.41, 6.81-6.97, 7.13-7.35, 7.77, 8.60, 8.69, 9.25.

Example 7-12: 4-[4-cyano-2-({[(2'R,4S)-6-(pyrazolo[1,5-a]pyridin-3-yl)-2,3-dihydrospiro[chromene-4,1'-cyclopropan]-2'-yl]carbonyl}amino)phenyl]butanoic acid TLC: Rf 0.40 (dichloromethane:methanol=9:1);
$^1$H-NMR (CDCl$_3$): δ 1.59-1.70, 1.76-1.84, 2.31, 2.43-2.53, 2.60-2.80, 4.15-4.44, 6.72, 6.89, 6.97, 7.09-7.36, 7.68, 7.89, 8.43, 8.70, 9.15.

Example 7-13: 4-[4-cyano-2-({[(2'R,4S)-6-(6-methoxy-3-pyridinyl)-2,3-dihydrospiro[chromene-4,1'-cyclopropan]-2'-yl]carbonyl}amino)phenyl]butanoic acid

[Chem. 83]

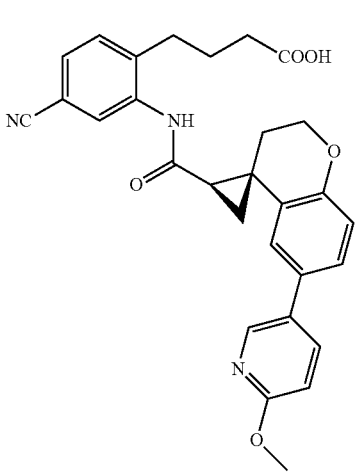

TLC: Rf 0.56 (ethyl acetate);
$^1$H-NMR (CD$_3$OD): δ 1.65-1.93, 2.14-2.29, 2.33, 2.58, 2.67-2.78, 3.92, 4.21, 4.32, 6.80-6.91, 7.06, 7.30, 7.42, 7.48, 7.84-7.95, 8.31.

Example 7-14: 4-{4-cyano-2-[({(2'R,4S)-6-[6-(1H-pyrazol-1-yl)-3-pyridinyl]-2,3-dihydrospiro[chromene-4,1'-cyclopropan]-2'-yl}carbonyl)amino]phenyl}butanoic acid

[Chem. 84]

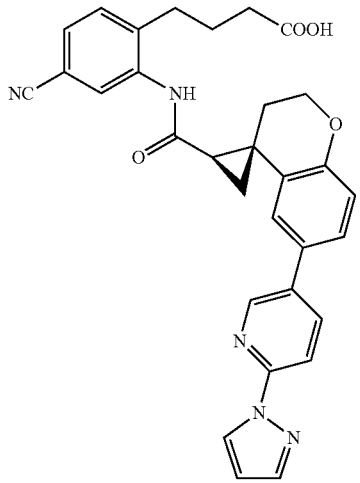

TLC: Rf 0.60 (chloroform:methanol=9:1);
$^1$H-NMR (DMSO-d$_6$): δ 1.57, 1.63-1.79, 1.89-2.01, 2.08-2.25, 2.50-2.56, 2.60-2.72, 4.03-4.18, 4.27-4.40, 6.59, 6.93, 7.27, 7.40, 7.47-7.60, 7.80-7.91, 7.96, 8.27, 8.63, 8.76, 9.88, 12.10.

Example 7-15: 4-{4-cyano-2-[({(2'R,4S)-6-[6-(dimethylamino)-3-pyridinyl]-2,3-dihydrospiro[chromene-4,1'-cyclopropan]-2'-yl}carbonyl)amino]phenyl}butanoic acid

[Chem. 85]

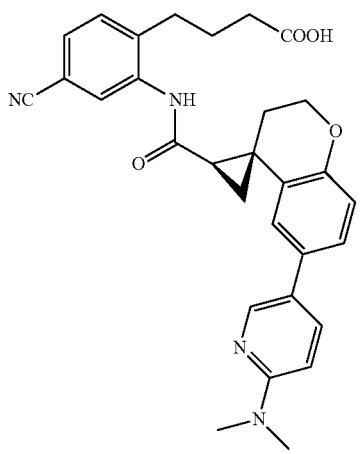

TLC: Rf 0.58 (chloroform:methanol=9:1);
$^1$H-NMR (DMSO-d$_6$): δ 1.51-1.62, 1.63-1.80, 1.84-1.95, 2.06-2.25, 2.51-2.57, 2.60-2.75, 3.18, 4.02-4.17, 4.23-4.39, 6.88, 7.01-7.21, 7.35-7.47, 7.55, 7.87, 8.10-8.29, 9.92, 12.10.

Example 7-16: 4-[4-cyano-2-({[(2'R,4S)-6-(6-methyl-3-pyridinyl)-2,3-dihydrospiro[chromene-4,1'-cyclopropan]-2'-yl]carbonyl}amino)phenyl]butanoic acid

[Chem. 86]

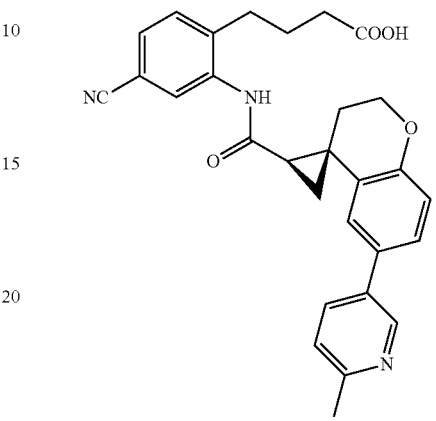

TLC: Rf 0.63 (dichloromethane:methanol=9:1);
$^1$H-NMR (DMSO-d$_6$): δ 1.46-1.56, 1.56-1.79, 2.03, 2.16, 2.66, 4.15, 4.22-4.33, 6.86, 7.20, 7.27, 7.33-7.44, 7.44-7.52, 8.08-8.21, 8.70, 11.11.

Example 7-17: 4-[4-cyano-2-({[(2'R,4S)-6-(6-fluoro-3-pyridinyl)-2,3-dihydrospiro[chromene-4,1'-cyclopropan]-2'-yl]carbonyl}amino)phenyl]butanoic acid TLC: Rf 0.59 (dichloromethane:methanol=9:1);
$^1$H-NMR (DMSO-d$_6$): δ 1.52-1.60, 1.65-1.79, 1.93, 2.07-2.23, 2.60-2.70, 4.03-4.15, 4.27-4.37, 6.90, 7.19-7.27, 7.40, 7.45, 7.56, 7.87, 8.25, 8.51, 9.87, 12.09.

Example 7-18: 4-{4-cyano-2-[({(2'R,4S)-6-[6-(methylsulfonyl)-3-pyridinyl]-2,3-dihydrospiro[chromene-4,1'-cyclopropan]-2'-yl}carbonyl)amino]phenyl}butanoic acid TLC: Rf 0.57 (dichloromethane:methanol=9:1);
$^1$H-NMR (DMSO-d$_6$): δ 1.58, 1.72, 1.92-2.01, 2.09-2.24, 2.60-2.70, 4.06-4.17, 4.30-4.40, 6.96, 7.33-7.45, 7.58, 7.88, 8.06, 8.41, 9.09, 9.90, 12.10.

Example 7-19: 4-[4-cyano-2-({[(2'R,4S)-6-(1H-pyrrolo[2,3-b]pyridin-5-yl)-2,3-dihydrospiro[chromene-4,1'-cyclopropan-2'-yl]carbonyl}amino)phenyl]butanoic acid TLC: Rf 0.55 (dichloromethane:methanol=9:1);
$^1$H-NMR (DMSO-d$_6$): δ 1.51-1.61, 1.65-1.80, 1.91, 2.09-2.24, 2.60-2.70, 4.09, 4.25-4.36, 6.47, 6.89, 7.18, 7.38-7.45, 7.45-7.50, 7.56, 7.88, 8.17, 8.47, 9.94, 11.65, 12.06.

Example 7-20: 4-[4-cyano-2-({[(2'R,4S)-6-(4-methyl-3,4-dihydro-2H-pyrido[3,2-b][1,4]oxazin-7-yl)-2,3-dihydrospiro[chromene-4,1'-cyclopropan]-2'-yl]carbonyl}amino)phenyl]butanoic acid TLC: Rf 0.65 (dichloromethane:methanol=9:1);
$^1$H-NMR (DMSO-$d_6$): δ 1.48-1.58, 1.65-1.79, 1.88, 2.06-2.14, 2.19, 2.59-2.70, 3.03, 3.40-3.47, 3.99-4.11, 4.19-4.33, 6.81, 7.03, 7.23, 7.29, 7.40, 7.56, 7.86, 7.95, 9.87, 12.08.

Example 7-21: 4-{4-cyano-2-[({(2'R,4S)-6-[6-(methylamino)-3-pyridinyl]-2,3-dihydrospiro[chromene-4,1'-cyclopropan]-2'-yl}carbonyl)amino]phenyl}butanoic acid

[Chem. 87]

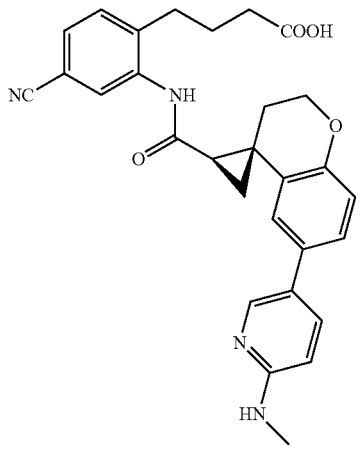

TLC: Rf 0.53 (dichloromethane:methanol=9:1);
$^1$H-NMR (DMSO-$d_6$): δ 1.52-1.61, 1.72, 1.84-1.94, 2.06-2.23, 2.60-2.70, 2.94, 4.02-4.13, 4.25-4.36, 6.88, 6.99, 7.14, 7.34-7.43, 7.56, 7.86, 8.09-8.21, 9.91, 12.13, 13.60.

Example 7-22: 4-{4-cyano-2-[({(2'R,4S)-6-[3-(2-hydroxy-2-propanyl)phenyl]-2,3-dihydrospiro[chromene-4,1'-cyclopropan]-2'-yl}carbonyl)amino]phenyl}butanoic acid TLC: Rf 0.56 (dichloromethane:methanol=9:1);
$^1$H-NMR (DMSO-$d_6$): δ 1.46, 1.54-1.62, 1.72, 1.79-1.88, 2.07-2.24, 2.60-2.70, 4.02-4.15, 4.25-4.36, 5.05, 6.88, 7.09, 7.29-7.46, 7.57, 7.66, 7.87, 9.90, 12.09.

Example 7-23: 4-[4-cyano-2-({[(2'R,4S)-6-(2-oxo-1-azetidinyl)-2,3-dihydrospiro[chromene-4,1'-cyclopropan]-2'-yl]carbonyl}amino)phenyl]butanoic acid TLC: Rf 0.47 (dichloromethane:methanol=20:1);
$^1$H-NMR (DMSO-$d_6$): δ 1.54-1.79, 2.02-2.11, 2.19, 2.39-2.68, 3.01-3.05, 3.55-3.61, 3.95-4.03, 4.20-4.29, 6.77-6.81, 7.16, 7.41, 7.56, 7.85, 9.90, 12.10.

Example 7-24: 4-[4-cyano-2-({[(2'R,4S)-6-(2-oxo-1,3-oxazolidin-3-yl)-2,3-dihydrospiro[chromene-4,1'-cyclopropan]-2'-yl]carbonyl}amino)phenyl]butanoic acid TLC: Rf 0.47 (dichloromethane:methanol=20:1);
$^1$H-NMR (DMSO-$d_6$): δ 1.54-1.79, 2.05-2.24, 2.39-2.68, 3.96-4.06, 4.23-4.31, 4.36-4.45, 6.81, 7.01, 7.27, 7.41, 7.56, 7.86, 9.92, 12.10.

Example 7-25: 4-{4-cyano-2-[({(2'R,4S)-6-[(4R)-4-hydroxy-2-oxo-1-pyrrolidinyl]-2,3-dihydrospiro[chromene-4,1'-cyclopropan]-2'-yl}carbonyl)amino]phenyl}butanoic acid TLC: Rf 0.40 (dichloromethane:methanol=20:1);
$^1$H-NMR (DMSO-$d_6$): δ 1.53-1.80, 2.06-2.13, 2.19, 2.37-2.81, 3.47-3.55, 4.00-4.08, 4.20-4.39, 5.29-5.37, 6.78, 7.14, 7.25, 7.40, 7.55, 7.87, 9.91, 12.10.

Example 7-26: 4-{4-cyano-2-[({(2'R,4S)-6-[4-(methylsulfonyl)phenyl]-2,3-dihydrospiro[chromene-4,1'-cyclopropan]-2'-yl}carbonyl)aminophenyl}butanoic acid TLC: Rf 0.49 (dichloromethane:methanol=9:1);
$^1$H-NMR (DMSO-$d_6$): δ 1.58, 1.72, 1.92, 2.08-2.24, 2.60-2.70, 3.23, 4.05-4.17, 4.27-4.39, 6.93, 7.25, 7.41, 7.50, 7.57, 7.84-7.99, 9.88, 12.09.

Example 7-27: 4-[4-cyano-2-({(2'R,4S)-6-(4-cyanophenyl)-2,3-dihydrospiro[chromene-4,1'-cyclopropan]-2'-yl]carbonyl}amino)phenyl]butanoic acid TLC: Rf 0.58 (dichloromethane:methanol=9:1);
$^1$H-NMR (DMSO-$d_6$): δ 1.56, 1.72, 1.93, 2.08-2.24, 2.59-2.69, 4.04-4.16, 4.27-4.38, 6.92, 7.25, 7.40, 7.51, 7.56, 7.87, 9.86, 12.08.

Example 7-28: 4-[4-cyano-2-({[(2'R,4S)-6-(1-methyl-1H-pyrazol-5-yl)-2,3-dihydrospiro[chromene-4,1'-cyclopropan]-2'-yl]carbonyl}amino)phenyl]butanoic acid TLC: Rf 0.59 (chloroform:methanol=9:1);
$^1$H-NMR (DMSO-$d_6$): δ 1.51-1.61, 1.64-1.88, 2.08-2.28, 2.39-2.46, 2.58-2.71, 3.82, 4.05-4.17, 4.27-4.39, 6.32, 6.90, 7.00, 7.25, 7.37-7.45, 7.55, 7.86, 9.89, 12.10.

Reference Example 16: Ethyl 4-{4-cyano-2-[({(2'R, 4S)-6-[1-(tetrahydro-2H-pyran-2-yl)-1H-pyrazol-4-yl]-2,3-dihydrospiro[chromene-4,1'-cyclopropan]-2'-yl}carbonyl)amino]phenyl}butanoate

[Chem. 88]

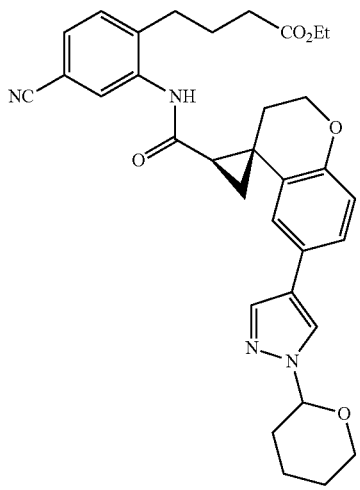

The title compound having the following physical property values was obtained by performing the same procedures as those of Reference Example 15 using a 1-(2-tetrahydropyranyl)-1H-pyrazole-4-boronic acid pinacol ester, instead of 4-fluorophenylboronic acid.

TLC: Rf 0.62 (hexane:ethyl acetate=1:2);

$^1$H-NMR (CDCl$_3$): δ 0.86, 1.64-1.79, 1.82-1.90, 2.02-2.16, 2.21-2.29, 2.34-2.43, 2.52-2.72, 3.28-3.42, 3.45-3.60, 3.65-3.80, 4.03-4.16, 4.25-4.40, 5.35-5.45, 6.81, 6.90, 7.13-7.23, 7.28, 7.71, 7.76, 8.74, 9.36.

Example 8: 4-[4-cyano-2-({[(2'R,4S)-6-(1H-pyrazol-4-yl)-2,3-dihydrospiro[chromene-4,1'-cyclopropan]-2'-yl]carbonyl}amino)phenyl]butanoic acid

[Chem. 89]

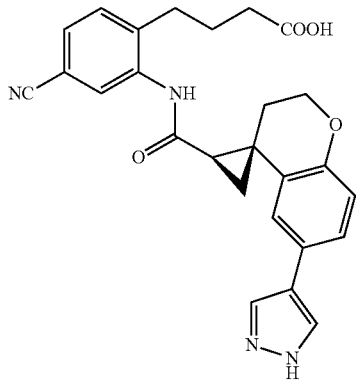

A hydrochloric acid-1,4-dioxane solution (4 mol/L, 0.1 mL) was added at room temperature to a 1-mL 1,4-dioxane solution of the compound (30 mg) produced in Reference Example 16. The reaction mixture was stirred at 60° C. for 3 h. After concentrating the reaction mixture under reduced pressure, the same procedures as those of Example 1 were performed to obtain the title compound having the following physical property values.

TLC: Rf 0.40 (ethyl acetate:methanol=20:1);

$^1$H-NMR (DMSO-d$_6$): δ 1.55, 1.64-1.79, 1.81-1.92, 2.04-2.27, 2.35-2.47, 2.52-2.74, 4.02, 4.27, 6.76, 7.09, 7.32, 7.40, 7.56, 7.85, 7.99, 9.89.

Reference Example 17: Ethyl 4-[4-cyano-2-([(2'R, 4S)-6-(4,4,5,5-tetramethyl-1,3,2-dioxaborolan-2-yl)-2,3-dihydrospiro[chromene-4,1'-cyclopropan]-2'-yl]carbonyl}amino)phenyl]butanoate

[Chem. 90]

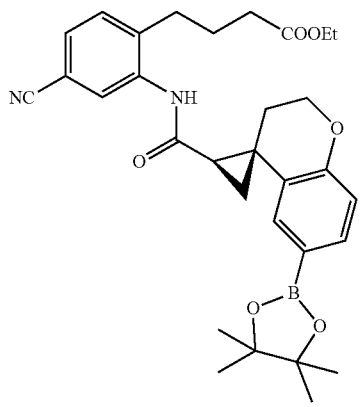

While replacing the atmosphere with argon, potassium acetate (1.44 g), bis(pinacolato)diboron (2.43 g), and a [1,1'-bis(diphenylphosphino)ferrocene]palladium(II) dichloride dichloromethane complex (300 mg) were added to a 40-mL dimethyl sulfoxide solution of the compound (4.00 g) produced in Reference Example 10, and the mixture was stirred at 90° C. for 4 h. After diluting the reaction mixture with ethyl acetate, water was added, and the mixture was extracted with ethyl acetate. The resulting organic layer was washed with water and saturated brine, dried over anhydrous sodium sulfate and then concentrated under reduced pressure. The resulting residue was purified by silica gel column chromatography (Yamazen Autopurification Device) to obtain the title compound (3.54 g) having the following physical property values.

TLC: Rf 0.37 (hexane:ethyl acetate=2:1);

$^1$H-NMR (CDCl$_3$): δ 1.01, 1.20-1.29, 1.31, 1.63-1.77, 1.84, 2.18-2.27, 2.33-2.42, 2.53-2.60, 3.20-3.34, 3.45-3.60, 4.00-4.10, 4.25-4.37, 6.78, 7.18, 7.28, 7.52, 8.68, 9.37.

Example 9: 4-[4-cyano-2-({[(2'R,4S)-6-(2-pyridinyl)-2,3-dihydrospiro[chromene-4,1'-cyclopropan]-2'-yl]carbonyl}amino)phenyl]butanoic acid

[Chem. 91]

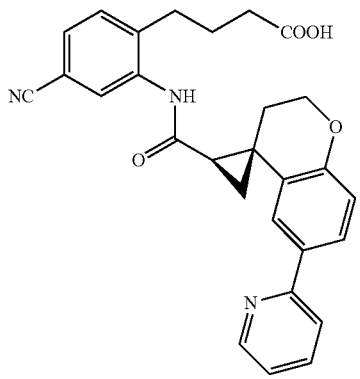

While replacing the atmosphere with argon, 2-bromopyridine (36 DL), cesium carbonate (120 mg), and a [1,1'-bis(diphenylphosphino)ferrocene]palladium(II) dichloride dichloromethane complex (7.5 mg) were added to a solution of the compound (100 mg) produced in Reference Example 17 in 1,2-dimethoxyethane (0.3 mL) and water (0.3 mL), and the mixture was stirred at 95° C. for 17 h. The reaction mixture was extracted with ethyl acetate, and the resulting organic layer was washed with water and saturated brine, dried over anhydrous sodium sulfate and then concentrated under reduced pressure. The resulting residue was purified by silica gel column chromatography (Yamazen Autopurification Device) to obtain ethyl 4-[4-cyano-2-({[(2'R,4S)-6-(2-pyridinyl)-2,3-dihydrospiro[chromene-4,1'-cyclopropan]-2'-yl]carbonyl}amino)phenyl]butanoate, and the same procedures as those of Example 1 were performed using this compound to obtain the title compound having the following physical property values.

TLC: Rf 0.44 (dichloromethane:methanol=9:1);

$^1$H-NMR (DMSO-$d_6$): δ 1.54-1.66, 1.68-1.88, 2.07-2.29, 2.54-2.76, 4.04-4.17, 4.26-4.38, 6.89, 7.23-7.33, 7.40, 7.52-7.64, 7.77-7.99, 8.61, 9.90, 12.10.

Example 10

The title compounds having the following physical property values were obtained by performing the same procedures as those of Example 9, except that the 2-bromopyridine was replaced with a corresponding halogen-containing heterocyclic ring.

Example 10-1: 4-[4-cyano-2-({[(2'R,4S)-6-(2-pyrimidinyl)-2,3-dihydrospiro[chromene-4,1'-cyclopropan]-2'-yl]carbonyl}amino)phenyl]butanoic acid TLC: Rf 0.45 (dichloromethane:methanol=9:1);

$^1$H-NMR (DMSO-$d_6$): δ 1.54-1.83, 2.07-2.28, 2.35-2.77, 4.05-4.22, 4.26-4.42, 6.93, 7.29-7.45, 7.56, 7.88, 7.94, 8.15, 8.84, 9.93, 12.10.

Example 10-2: 4-[4-cyano-2-({[(2'R,4S)-6-(1,3-thiazol-2-yl)-2,3-dihydrospiro[chromene-4,1'-cyclopropan-2'-yl]carbonyl}amino)phenyl]butanoic acid

[Chem. 92]

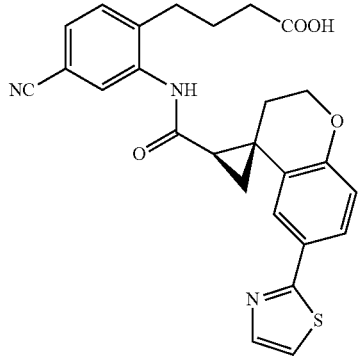

TLC: Rf 0.81 (ethyl acetate:methanol=20:1);

$^1$H-NMR (CDCl$_3$): δ 1.19-1.32, 1.34-1.85, 2.10-2.25, 2.40-2.79, 3.61, 4.35, 4.48-4.62, 6.88, 7.15-7.30, 7.35, 7.38-7.47, 7.68-7.77, 7.85, 8.88, 10.00.

Example 10-3: 4-[4-cyano-2-({[(2'R,4S)-6-(1,3-oxazol-2-yl)-2,3-dihydrospiro[chromene-4,1'-cyclopropan]-2'-yl]carbonyl}amino)phenyl]butanoic acid

[Chem. 93]

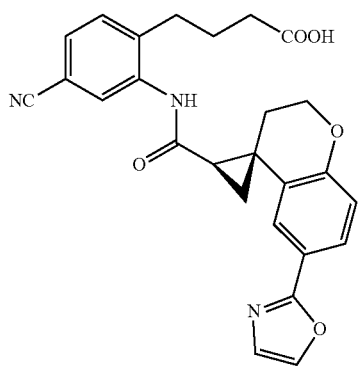

TLC: Rf 0.81 (ethyl acetate:methanol=20:1);

$^1$H-NMR (CDCl$_3$): δ 1.18-1.29, 1.53, 1.68-1.86, 2.09-2.33, 2.43-2.87, 3.60, 4.39, 4.52-4.64, 6.90, 7.15, 7.17, 7.28, 7.67, 7.72, 8.05, 8.92, 9.95.

Example 10-4: 4-[4-cyano-2-([{(2'R,4S)-6-(1-methyl-1H-1,2,3-triazol-4-yl)-2,3-dihydrospiro[chromene-4,1'-cyclopropan]-2'-yl]carbonyl}amino)phenyl]butanoic acid

[Chem. 94]

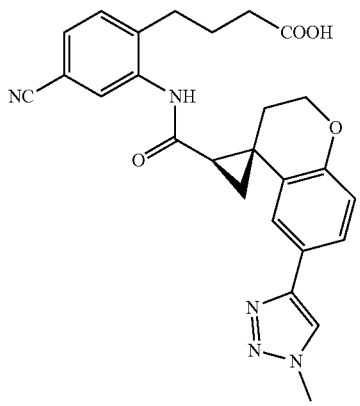

TLC: Rf 0.58 (ethyl acetate:methanol=20:1);
$^1$H-NMR (CDCl$_3$): δ 1.21-1.32, 1.56, 1.69-1.86, 2.14-2.31, 2.44-2.88, 3.64, 4.15-4.20, 4.34, 4.53, 6.86, 7.13-7.31, 7.63, 7.68, 7.79, 8.92, 10.01.

Example 10-5: 4-[4-cyano-2-({[(2'R,4S)-6-(3-pyridazinyl)-2,3-dihydrospiro[chromene-4,1'-cyclopropan]-2'-yl]carbonyl}amino)phenyl]butanoic acid

[Chem. 95]

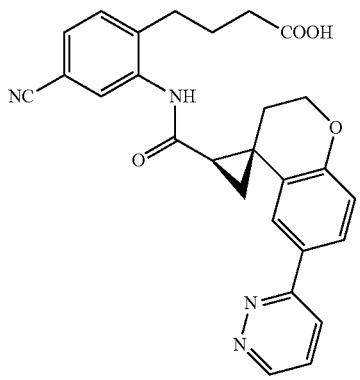

TLC: Rf 0.40 (dichloromethane:methanol=9:1);
$^1$H-NMR (CDCl$_3$): δ 1.17-1.31, 1.61, 1.66-1.90, 2.11-2.32, 2.36-2.82, 3.48-3.71, 4.35, 4.54, 6.98, 7.21, 7.28, 7.36, 7.66, 7.83, 7.80-7.83, 8.87, 9.15, 10.07.

Example 10-6: 4-[4-cyano-2-({[(2'R,4S)-6-(2-pyrazinyl)-2,3-dihydrospiro[chromene-4,1'-cyclopropan]-2'-yl]carbonyl}amino)phenyl]butanoic acid TLC: Rf 0.40 (dichloromethane:methanol=9:1);
$^1$H-NMR (CDCl$_3$): δ 1.25, 1.61, 1.68-1.88, 2.08-2.29, 2.40-2.87, 3.49, 4.25-4.41, 4.52, 6.97, 7.21, 7.29, 7.46, 7.61, 8.45, 8.62, 8.85, 8.97, 9.93.

Example 10-7: 4-{4-cyano-2-[({(2'R,4S)-6-[5-(methylsulfonyl)-2-pyridinyl]-2,3-dihydrospiro[chromene-4,1'-cyclopropan]-2'-yl}carbonyl)amino]phenyl}butanoic acid TLC: Rf 0.48 (dichloromethane:methanol=9:1);
$^1$H-NMR (DMSO-d$_6$): δ 1.61, 1.73, 1.80-1.92, 2.07-2.28, 2.38-2.75, 3.34, 4.06-4.20, 4.26-4.44, 6.96, 7.41, 7.57, 7.71, 7.88, 7.97, 8.18-8.36, 9.06, 9.91, 12.08.

Example 10-8: 4-{4-cyano-2-[({(2'R,4S)-6-[5-(hydroxymethyl)-2-pyridinyl]-2,3-dihydrospiro[chromene-4,1'-cyclopropan]-2'-yl}carbonyl)amino]phenyl}butanoic acid TLC: Rf 0.42 (dichloromethane:methanol=9:1);
$^1$H-NMR (DMSO-d$_6$): δ 1.51-1.62, 1.63-1.87, 2.07-2.30, 2.53-2.75, 4.03-4.19, 4.25-4.39, 4.54, 5.29, 6.88, 7.40, 7.52-7.64, 7.70-7.94, 8.53, 9.92, 12.07.

Example 10-9: 4-[4-cyano-2-({[(2'R,4S)-6-(5-fluoro-2-pyridinyl)-2,3-dihydrospiro[chromene-4,1'-cyclopropan]-2'-yl]carbonyl}amino)phenyl]butanoic acid TLC: Rf 0.64 (dichloromethane:methanol=9:1);
$^1$H-NMR (DMSO-d$_6$): δ 1.53-1.64, 1.65-1.88, 2.06-2.32, 2.40-2.80, 4.00-4.19, 4.24-4.40, 6.89, 7.40, 7.51-7.65, 7.71-7.84, 7.88, 8.00-8.05, 8.60, 9.92, 12.08.

Example 10-10: 4-[4-cyano-2-({[(2'R,4S)-6-(6-methoxy-2-pyridinyl)-2,3-dihydrospiro[chromene-4,1'-cyclopropan]-2'-yl]carbonyl}amino)phenyl]butanoic acid TLC: Rf 0.50 (dichloromethane:methanol=9:1);
$^1$H-NMR (DMSO-d$_6$): δ 1.53-1.64, 1.66-1.79, 1.79-1.91, 2.03-2.30, 2.40-2.79, 3.94, 4.02-4.16, 4.26-4.40, 6.70, 6.89, 7.40, 7.48-7.62, 7.73, 7.80-7.89, 9.89, 12.07.

Example 10-11: 4-[4-cyano-2-({[(2'R,4S)-6-(5-methoxy-2-pyridinyl)-2,3-dihydrospiro[chromene-4,1'-cyclopropan]-2'-yl]carbonyl}amino)phenyl]butanoic acid TLC: Rf 0.70 (dichloromethane:methanol=9:1);
$^1$H-NMR (CDCl$_3$): δ 1.16-1.30, 1.57, 1.70-1.83, 2.04-2.27, 2.52, 2.59-2.73, 2.74-2.92, 3.54, 3.92, 4.30, 4.48, 6.89, 7.19, 7.24-7.31, 7.38, 7.49, 7.52, 8.18, 8.83, 10.06.

Example 10-12: 4-[4-cyano-2-({[(2'R,4S)-6-(5-methyl-1,2,4-oxadiazol-3-yl)-2,3-dihydrospiro[chromene-4,1'-cyclopropan]-2'-yl]carbonyl}amino)phenyl]butanoic acid TLC: Rf 0.69 (ethyl acetate:methanol=9:1);
$^1$H-NMR (CDCl$_3$): δ 1.19-1.31, 1.56, 1.70-1.88, 2.12-2.32, 2.42-2.84, 3.54, 4.37, 4.56, 6.92, 7.16-7.31, 7.71-7.82, 8.91, 9.84.

Example 11: 4-(4-cyano-2-{[(2'R,4S)-2,3-dihydrospiro 1-benzopyran-4,1'-cyclopropane]-2'-carbonyl]amino}phenyl) butanoic acid The title compound having the following physical property values was obtained by performing the same procedures as those of Reference Example 10→Example 1 using the compound produced in Reference Example 9 and the compound produced in Reference Example 3.

TLC: Rf 0.62 (chloroform:methanol=9:1);
$^1$H-NMR (CD$_3$OD): δ 1.66, 1.77-1.91, 2.08-2.28, 2.34, 2.48, 2.71, 4.16, 4.28, 6.74, 6.82-6.91, 7.06, 7.42, 7.48, 7.91.

Reference Example 18: (2'R,4S)-2'-{[2-(4-ethoxy-4-oxobutyl)-5-fluorophenyl]carbamoyl}-2,3-dihydrospiro[1-benzopyran-4,1'-cyclopropane]-6-carboxylic acid The title compound having the following physical property values was obtained by performing the same procedures as those of Reference Example 7→Reference Example 9→Reference Example 10→Example 1, except that 5-fluoro-2-iodonitrobenzene was used instead of 3-nitro-4-bromobenzaldehyde.

$^1$H-NMR (DMSO-d&): δ 1.12, 1.52-1.77, 2.12, 2.26, 2.51-2.62, 3.87-4.02, 4.12, 4.34, 6.86, 6.92, 7.20, 7.41, 7.47, 7.68, 9.68, 12.68.

Example 12

The title compounds having the following physical property values were obtained by performing the same procedures as those of Reference Example 12→Example 1 using the compound produced in Reference Example 18 instead of the compound produced in Reference Example 11, using methylamine hydrochloride or a corresponding amine compound.

Example 12-1: 4-[4-fluoro-2-({[(2'R,4S)-6-(methylcarbamoyl)-2,3-dihydrospiro[chromene-4,1'-cyclopropan]-2'-yl]carbonyl}amino)phenyl]butanoic acid TLC: Rf 0.69 (ethyl acetate:methanol=19:1);
$^1$H-NMR (CD$_3$OD): δ 1.62-1.87, 2.12-2.28, 2.32, 2.56-2.78, 2.90, 4.23, 4.34, 6.76-6.89, 7.20, 7.38-7.51, 7.54.

Example 12-2: 4-{4-fluoro-2-[({(2'R,4S)-6-[(2-methoxyethyl)carbamoyl]-2,3-dihydrospiro [chromene-4,1'-cyclopropan]-2'-yl}carbonyl)amino] phenyl}butanoic acid TLC: Rf 0.67 (ethyl acetate:methanol=19:1);
$^1$H-NMR (DMSO-d$_6$): δ 1.51-1.79, 2.06-2.22, 2.41-2.61, 3.25, 3.36-3.46, 4.07, 4.31, 6.83, 6.95, 7.19, 7.33, 7.43, 7.63, 8.42, 9.74, 12.06.

Example 12-3: 4-{4-fluoro-2-[({(2'R,4S)-6-[(1-methyl-1H-pyrazol-4-yl)carbamoyl]-2,3-dihydrospiro[chromene-4,1'-cyclopropan]-2'-yl}carbonyl)amino]phenyl}butanoic acid TLC: Rf 0.64 (ethyl acetate:methanol=9:1);
$^1$H-NMR (CD30OD): δ 1.66-1.86, 2.12-2.37, 2.57-2.70, 3.88, 4.25, 4.37, 6.81-6.92, 7.21, 7.45, 7.58, 7.63, 7.68, 8.00.

Reference Example 19: Ethyl 4-(2-{[(1R,2R)-6'-(benzyloxy)-2',3'-dihydrospiro[cyclopropane-1,1'-indene]-2-carbonyl]amino}-4-cyanophenyl)butanoate The title compound having the following physical property values was obtained by performing the same procedures as those of Reference Example 1→Reference Example 2→Reference Example 3→Reference Example 10, using 6-(benzyloxy)-2,3-dihydro-1H-inden-1-one instead of 4-chromanone.

[Chem. 96]

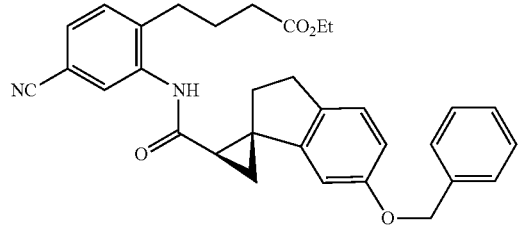

$^1$H-NMR (CDCl$_3$): δ 1.25, 1.38-1.45, 1.68-1.81, 1.82-1.87, 2.32-2.46, 2.57-2.67, 2.86-3.08, 3.82-3.92, 3.97-4.07, 5.00, 6.46, 6.77, 7.12, 7.17, 7.25-7.31, 7.32-7.43, 8.78, 9.15.

Example 13: 4-[2-({[(1R,2R)-6'-(benzyloxy)-2',3'-dihydrospiro[cyclopropane-1,1'-inden]-2-yl]carbonyl}amino)-4-cyanophenyl]butanoic acid The title compound having the following physical property values was obtained by performing the same procedures as those of Example 1 using the compound produced in Reference Example 19, instead of the compound produced in Reference Example 12.

TLC: Rf 0.53 (dichloromethane:methanol=10:1);
$^1$H-NMR (CDCl$_3$): δ 1.36-1.43, 1.66-1.77, 1.79-1.85, 2.31, 2.42-2.73, 2.84-3.09, 5.05, 6.49, 6.81, 7.13-7.21, 7.24-7.30, 7.32-7.47, 8.72, 8.92.

Example 14: 4-[4-cyano-2-({[(1R,2R)-6'-hydroxy-2',3'-dihydrospiro cyclopropane-1,1'-inden]-2-yl] carbonyl}amino)phenyl]butanoic acid 10% Palladium/carbon (12 mg) was added to a solution of the compound (40 mg) produced in Example 13 in ethyl acetate (3 mL) and 1,4-dioxane (1 mL). After replacing the atmosphere with hydrogen, the mixture was stirred at room temperature for 9 h. The reaction mixture was filtered using Celite, and the filtrate was concentrated under reduced pressure. The resulting residue was purified by silica gel column chromatography to obtain the title compound (32 mg) having the following physical property values.

TLC: Rf 0.40 (dichloromethane:methanol=10:1);
$^1$H-NMR (CDCl$_3$): δ 1.36-1.43, 1.65-1.85, 2.32, 2.47-2.55, 2.58-2.76, 2.83-3.08, 6.37, 6.62, 7.06, 7.22, 7.25-7.37, 8.74, 8.92.

Reference Example 20: Ethyl 4-(4-cyano-2-{[(1R, 2R)-6'-hydroxy-2',3'-dihydrospiro[cyclopropane-1, 1'-indene]-2-carbonyl]amino}phenyl)butanoate The title compound having the following physical property values was obtained by performing the same procedures as those of Example 14 using the compound produced in Reference Example 19, instead of the compound produced in Example 13.

$^1$H-NMR (CDCl$_3$): δ 1.24, 1.38-1.43, 1.70-1.87, 2.31-2.49, 2.58-2.67, 2.85-3.07, 3.89-4.01, 4.04-4.16, 4.49, 6.31, 6.58, 7.04, 7.17, 7.26-7.31, 8.78, 9.18.

Reference Example 21: Ethyl 4-[4-cyano-2-({[(1R, 2R)-6'-[(1-methyl-1H-pyrazol-4-yl)methoxy]-2',3'-dihydrospiro[cyclopropane-1,1'-indene]-2-carbonyl}amino)phenyl]butanoate Under a stream of nitrogen, cyanomethylenetributylphosphorane (0.06 mL) was dropped into a 0.2-mL toluene solution of the compound (30 mg) produced in Reference Example 20 and (1-methylpyrazol-4-yl)methanol (9.6 mg), and the mixture was stirred overnight at 100° C. The reaction mixture was concentrated under reduced pressure. The resulting residue was purified by silica gel column chromatography to obtain the title compound (7 mg) having the following physical property values.

$^1$H-NMR (CDCl$_3$): δ 1.26, 1.39-1.42, 1.68-1.85, 2.28-2.51, 2.55-2.65, 2.83-3.05, 3.87-4.01, 4.04-4.18, 4.89, 6.40, 6.72-6.79, 7.06-7.38, 7.41, 7.51, 8.77, 9.13.

Example 15: 4-{4-cyano-2-[({(1R,2R)-6'-[(1-methyl-1H-pyrazol-4-yl)methoxy-2',3'-dihydrospiro[cyclopropane-1,1'-inden]-2-yl}carbonyl)amino]phenyl}butanoic acid The title compound having the following physical property values was obtained by performing the same procedures as those of Example 1 using the compound produced in Reference Example 21, instead of the compound produced in Reference Example 12.

TLC: Rf 0.26 (dichloromethane:methanol=20:1);

$^1$H-NMR (DMSO-d$_6$): δ 1.45-1.57, 1.66-1.79, 2.13-2.25, 2.26-2.75, 2.84-2.92, 3.81, 4.90, 6.51, 6.77, 7.09, 7.39, 7.47, 7.55, 7.77, 7.96.

Reference Example 22: Ethyl 4-[4-cyano-2-((1R, 2R)-6'-[2-(methylamino)-2-oxoethoxy]-2',3'-dihydrospiro[cyclopropane-1,1'-indene]-2-carbonyl}amino)phenyl]butanoate Potassium carbonate (33 mg) and tetrabutylammonium iodide (4.4 mg) and subsequently 2-chloro-N-methylacetamide (25.7 mg) were added at room temperature to a 0.5-mL DMF solution of the compound (50 mg) produced in Reference Example 20. The reaction mixture was stirred overnight at 50° C. The reaction mixture was diluted with ethyl acetate and, after adding a saturated ammonium chloride aqueous solution and water, extracted with ethyl acetate. The resulting organic layer was washed with water and 20% brine, dried over anhydrous sodium sulfate and then concentrated under reduced pressure. The resulting residue was purified by silica gel column chromatography (Yamazen Autopurification Device) to obtain the title compound (51 mg) having the following physical property values.

TLC: Rf 0.26 (hexane:ethyl acetate=4:1);

$^1$H-NMR (CDCl$_3$): δ 1.19, 1.39-1.44, 1.68-1.84, 1.86-1.89, 2.27-2.70, 2.84-3.08, 3.79-3.93, 3.95-4.06, 4.07, 4.44, 6.38, 6.55, 6.70, 7.13-7.20, 7.26-7.30, 8.75, 9.07.

Example 16: 4-{4-cyano-2-[({(1R,2R)-6'-2-(methylamino)-2-oxoethoxy]-2',3'-dihydrospiro[cyclopropane-1,1'-inden]-2-yl}carbonyl)amino]phenyl}butanoic acid The title compound having the following physical property values was obtained by performing the same procedures as those of Example 1 using the compound produced in Reference Example 22, instead of the compound produced in Reference Example 12.

TLC: Rf 0.59 (ethyl acetate:methanol=9:1);

$^1$H-NMR (DMSO-d$_6$): δ 1.44-1.51, 1.56, 2.07-2.34, 2.66, 2.87, 6.54, 6.76, 7.12, 7.41, 7.56, 7.92, 8.01, 9.75, 12.12.

Example 17: 4-{4-cyano-2-[({(1R,2R)-6'-[2-(dimethylamino)-2-oxoethoxy]-2',3'-dihydrospiro[cyclopropane-1,1'-inden]-2-yl}carbonyl)amino]phenyl}butanoic acid The title compound having the following physical property values was obtained by performing the same procedures as those of Reference Example 22→Example 1, using 2-chloro-N,N-dimethylacetamide instead of 2-chloro-N-methylacetamide.

TLC: Rf 0.54 (ethyl acetate:methanol=9:1);

$^1$H-NMR (DMSO-d$_6$): δ 1.47-1.58, 1.71, 2.08-2.32, 2.33-2.70, 2.82-2.91, 3.00, 4.74, 6.49, 6.70, 7.10, 7.41, 7.57, 7.91, 9.79, 12.16.

Reference Example 23: Ethyl 4-[4-cyano-2-({[(1R, 2R)-6'-[(trifluoromethanesulfonyl)oxyl]-2',3'-dihydrospiro[cyclopropane-1,1'-indene]-2-carbonyl}amino)phenyl]butanoate

[Chem. 97]

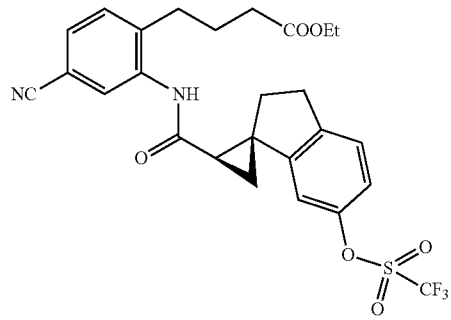

In a nitrogen atmosphere, triethylamine (0.1 mL) and 1,1,1-trifluoro-N-phenyl-N-(trifluoromethylsulfonyl)methanesulfoneamide (128 mg) were added to a 2-mL dichloromethane solution of the compound (100 mg) produced in Reference Example 20, and the mixture was stirred at room temperature for 3 h. The mixture was further stirred at room temperature for 2 h after adding 1,1,1-trifluoro-N-phenyl-N-(trifluoromethylsulfonyl)methanesulfoneamide (128 mg) to the reaction liquid. The reaction liquid was purified by silica gel column chromatography to obtain the title compound (130 mg) having the following physical property values.

$^1$H-NMR (CDCl$_3$): δ 1.22-1.29, 1.39-1.44, 1.70-1.83, 1.86-1.91, 2.34-2.51, 2.60-2.67, 2.95-3.14, 3.90-4.02, 4.05-4.16, 6.67, 7.03, 7.19, 7.21-7.31, 8.78, 9.19.

Reference Example 24: (1R,2R)-2-{[5-cyano-2-(4-ethoxy-4-oxobutyl)phenyl]carbamoyl}-2',3'-dihydrospiro[cyclopropane-1,1'-indene]-6'-carboxylic acid

[Chem. 98]

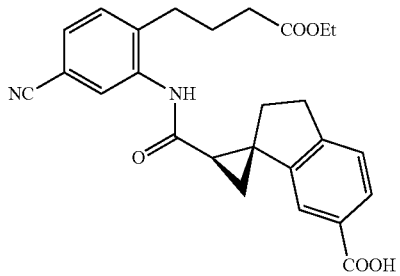

The compound (120 mg) produced in Reference Example 23 was dissolved in DMSO (3 mL) and ultrasonically deaerated under reduced pressure. 1,3-Bis(diphenylphosphino)propane (dppp; 18 mg), palladium(II) acetate (10 mg), lithium chloride (92 mg), sodium formate (148 mg), diisopropylethylamine (0.34 mL), and an acetic anhydride (0.19 mL) were added to the reaction liquid. The mixture was stirred at 90° C. for 4 h while replacing the atmosphere with carbon monoxide. After adding a 0.1 N hydrochloric acid aqueous solution, the reaction mixture was extracted with ethyl acetate, and the resulting organic layer was dried over anhydrous sodium sulfate and then concentrated under reduced pressure. The resulting residue was purified by silica gel column chromatography to obtain the title compound (40 mg) having the following physical property values.

$^1$H-NMR (CDCl$_3$): δ 1.18, 1.44-1.51, 1.64-1.79, 1.85-1.90, 2.35-2.48, 2.57-2.78, 2.99-3.17, 3.84-3.91, 4.03-4.11, 7.18, 7.24-7.36, 7.52, 7.89, 8.81, 9.29.

Example 18

The title compounds having the following physical property values were obtained by performing the same procedures as those of Reference Example 12→Example 1 using the compound produced in Reference Example 24 instead of the compound produced in Reference Example 11, using methylamine hydrochloride or a corresponding amine compound.

Example 18-1: 4-[4-cyano-2-({[(1R,2R)-6'-(methylcarbamoyl)-2',3'-dihydrospiro[cyclopropane-1,1'-inden]-2-yl]carbonyl}amino)phenyl}butanoic acid

[Chem. 99]

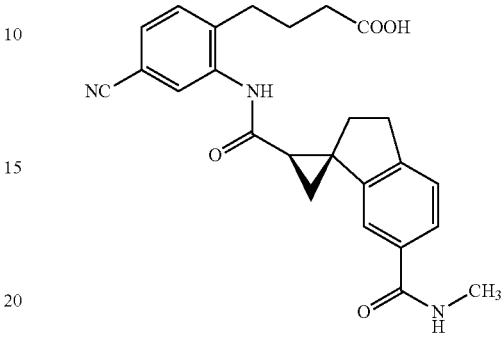

TLC: Rf 0.29 (dichloromethane:methanol=20:1);

$^1$H-NMR (CDCl$_3$): δ 1.26-1.31, 1.66-1.78, 1.82-1.87, 2.23-2.30, 2.34-2.48, 2.52-2.71, 2.91-3.03, 3.04, 3.13-3.27, 6.21-6.29, 7.17, 7.19-7.35, 7.70, 8.82, 9.56.

Example 18-2: 4-{4-cyano-2-[({(1R,2R)-6'-[(2-methoxyethyl)carbamoyl]-2',3'-dihydrospiro[cyclopropane-1,1'-inden]-2-yl}carbonyl)amino]phenyl}butanoic acid

[Chem. 100]

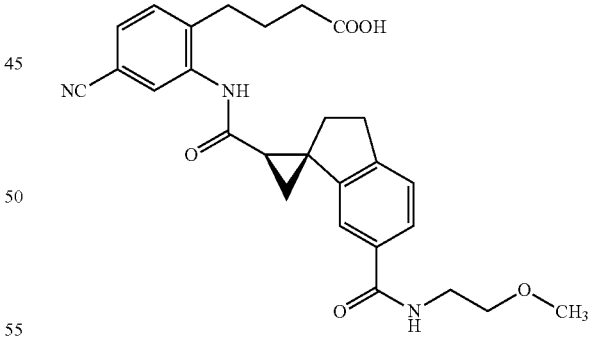

TLC: Rf 0.50 (dichloromethane:methanol=20:1);

$^1$H-NMR (CDCl$_3$): δ 1.25-1.31, 1.65-1.77, 1.81-1.86, 2.23-2.30, 2.35-2.47, 2.51-2.71, 2.91-3.03, 3.13-3.27, 3.41, 3.54-3.78, 6.62-6.67, 7.17, 7.19-7.30, 7.34, 7.66, 8.82, 9.51.

Example 18-3: 4-{4-cyano-2-[({(1R,2R)-6'-[(1-methyl-1H-pyrazol-4-yl)carbamoyl]-2',3'-dihydrospiro[cyclopropane-1,1'-inden]-2-yl}carbonyl)amino]phenyl}butanoic acid

[Chem. 101]

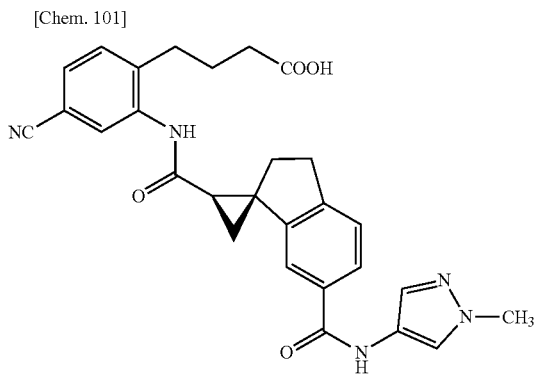

TLC: Rf 0.28 (dichloromethane:methanol=20:1);
¹H-NMR (CDCl₃): δ 1.26-1.34, 1.68-1.78, 1.81-1.88, 2.25-2.31, 2.43-2.72, 2.95-3.06, 3.17-3.23, 3.92, 7.16-7.33, 7.42, 7.52, 7.75, 7.86, 7.99, 8.83, 9.54.

Example 19: 4-[4-cyano-2-([(1R,2R)-6'-(3-pyridinyl)-2',3'-dihydrospiro[cyclopropane-1,1'-inden]-2-yl]carbonyl}amino)phenyl]butanoic acid The title compound having the following physical property values was obtained by performing the same procedures as those of Reference Example 15→Example 1 using the compound produced in Reference Example 23, using pyridine-3-boronic acid instead of 4-fluorophenylboronic acid.
TLC: Rf 0.30 (dichloromethane:methanol=20:1);
¹H-NMR (CD₃OD): δ 1.58-1.66, 1.75-1.90, 2.25-2.45, 2.47-2.55, 2.68-2.79, 3.07-3.16, 7.15, 7.34-7.56, 7.98, 8.10, 8.52, 8.78.

Reference Example 25: (2'R,4S)-2'-{[5-cyano-2-(4-ethoxy-4-oxobutyl)phenylcarbamoyl}-7-fluoro-2,3-dihydrospiro[1-benzopyran-4,1'-cyclopropane]-6-carboxylic acid

[Chem. 102]

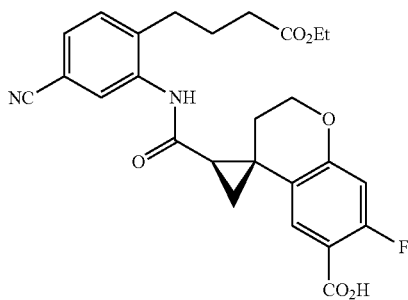

The title compound having the following physical property values was obtained by performing the same procedures as those of Reference Example 1→Reference Example 2→Reference Example 3→Reference Example 4→Reference Example 5→Reference Example 6→Reference Example 10→Reference Example 11, using 7-fluorochroman-4-one instead of 4-chromanone.
¹H-NMR (CDCl₃): δ 1.13, 1.66-1.78, 1.84-1.90, 2.25-2.35, 2.42-2.47, 2.58-2.67, 3.60-3.73, 3.78-3.90, 4.10-4.22, 4.35-4.44, 6.60, 7.19, 7.26-7.33, 7.50, 8.71, 9.37.

Example 20

The title compounds having the following physical property values were obtained by performing the same procedures as those of Reference Example 12→Example 1 using the compound produced in Reference Example 25 instead of the compound produced in Reference Example 11, using methylamine hydrochloride or a corresponding amine compound.

Example 20-1: 4-[4-cyano-2-({[(2'R,4S)-7-fluoro-6-(methylcarbamoyl-2,3-dihydrospiro[chromene-4,1'-cyclopropan-2'-yl]carbonyl}amino)phenylbutanoic acid

[Chem. 103]

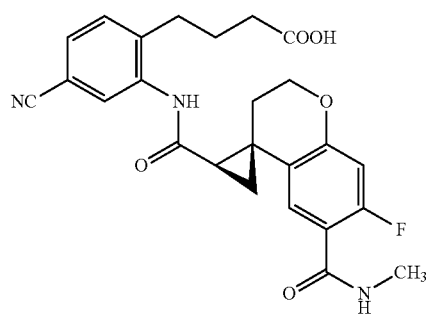

TLC: Rf 0.74 (dichloromethane:methanol=10:1);
¹H-NMR (CDCl₃): δ 1.18-1.29, 1.50-1.62, 1.70-1.80, 2.05-2.15, 2.20-2.27, 2.44-2.76, 3.03, 3.54-3.60, 4.31-4.40, 4.54-4.59, 6.57, 6.82-6.95, 7.20, 7.24-7.33, 8.06, 8.88, 9.94.

Example 20-2: 4-{4-cyano-2-[({(2'R,4S)-7-fluoro-6-[(2-methoxyethyl)carbamoyl]-2,3-dihydrospiro[chromene-4,1'-cyclopropan]-2'-yl}carbonyl)amino]phenyl}butanoic acid

[Chem. 104]

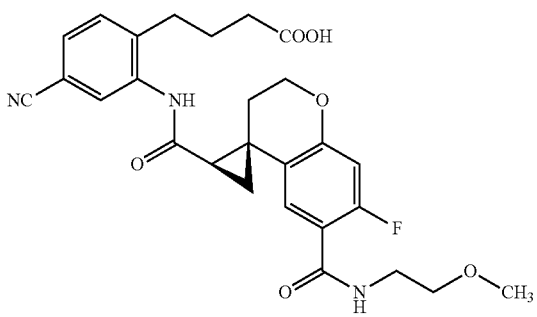

TLC: Rf 0.49 (dichloromethane:methanol=10:1);
¹H-NMR (CDCl₃): δ 1.19-1.26, 1.58-1.64, 1.68-1.84, 2.05-2.29, 2.45-2.77, 3.39, 3.53-3.64, 3.65-3.72, 4.31-4.43, 4.54-4.62, 6.57, 7.17-7.34, 8.05, 8.88, 9.93.

Example 20-3: 4-[4-cyano-2-({[(2'R,4S)-6-(ethyl-carbamoyl)-7-fluoro-2,3-dihydrospiro[chromene-4,1'-cyclopropan]-2'-yl]carbonyl}amino)phenyl]butanoic acid TLC: Rf 0.62 (hexane:ethyl acetate=1:3);
$^1$H-NMR (DMSO-d$_6$): δ 1.09, 1.55, 1.65-1.78, 2.02-2.28, 2.47, 2.60-2.71, 3.17-3.33, 4.12, 4.33, 6.73, 7.19, 7.41, 7.56, 7.88, 8.07, 9.89, 12.11.

Example 20-4: 4-[4-cyano-2-({[(2'R,4S)-7-fluoro-6-(propylcarbamoyl)-2,3-dihydrospiro[chromene-4,1'-cyclopropan]-2'-yl]carbonyl}amino)phenyl]butanoic acid TLC: Rf 0.56 (hexane:ethyl acetate=1:2);
$^1$H-NMR (DMSO-d$_6$): δ 0.87, 1.42-1.58, 1.62-1.78, 2.04-2.23, 2.42, 2.60-2.69, 3.11-3.23, 4.12, 4.31, 6.73, 7.18, 7.41, 7.56, 7.88, 8.06, 9.90, 12.11.

Example 20-5: 4-[4-cyano-2-({[(2'R,4S)-7-fluoro-6-(isopropylcarbamoyl)-2,3-dihydrospiro[chromene-4,1'-cyclopropan]-2'-yl]carbonyl}amino)phenyl]butanoic acid

[Chem. 105]

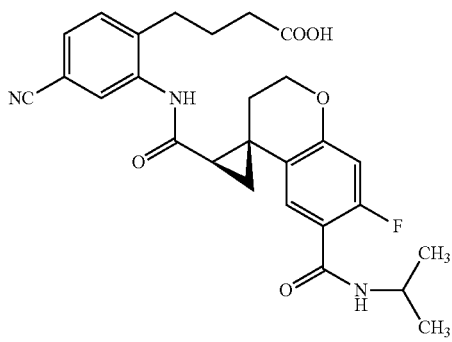

TLC: Rf 0.68 (hexane:ethyl acetate=1:3);
$^1$H-NMR (DMSO-d$_6$): δ 1.13, 1.53, 1.63-1.79, 2.02-2.24, 2.46, 2.61-2.69, 3.96-4.18, 4.33, 6.72, 7.14, 7.41, 7.56, 7.80-7.92, 9.89, 12.11.

Example 21: 4-[4-cyano-2-({[(2'R,4S)-6-fluoro-2,3-dihydrospiro[chromene-4,1'-cyclopropan]-2'-yl]carbonyl}amino)phenyl]butanoic acid The title compound having the following physical property values was obtained by performing the same procedures as those of Reference Example 1→Reference Example 2→Reference Example 3→Reference Example 10→Example 1 using 6-fluoro-4-chromanone instead of 4-chromanone.

TLC: Rf 0.38 (dichloromethane:methanol=10:1);
$^1$H-NMR (CDCl$_3$): δ 1.46-1.80, 2.18-2.24, 2.48-2.75, 4.09-4.32, 6.55, 6.75-6.87, 7.21, 7.25-7.34, 8.66, 9.00.

Reference Example 26: Ethyl 4-(2-{[(2'R,4S)-6-benzoyl-2,3-dihydrospiro[1-benzopyran-4,1'-cyclpropane]-2'-carbonyl]amino}-4-cyanophenyl)butanoate Phenylboronic acid (10 mg), potassium carbonate (22 mg), and a [1,1'-bis(diphenylphosphino)ferrocene]palladium(I) dichloride dichloromethane complex (9 mg) were added to a 1-mL anisole solution of the compound (30 mg) produced in Reference Example 10, and the mixture was stirred at 80° C. for 3 h in a carbon monoxide atmosphere. A saturated sodium bicarbonate aqueous solution was poured into the reaction mixture, and the mixture was extracted with ethyl acetate. The resulting organic layer was washed with saturated brine, dried over anhydrous magnesium sulfate and then concentrated under reduced pressure. The resulting residue was purified by silica gel column chromatography (Yamazen Autopurification Device) to obtain the title compound (18 mg) having the following physical property values.

TLC: Rf 0.38 (hexane:ethyl acetate=1:1);
$^1$H-NMR (CDCl$_3$): δ 0.99, 1.61-1.80, 1.87, 2.27-2.36, 2.37-2.44, 2.61, 2.71, 3.43-3.56, 3.66, 3.81, 4.11-4.23, 4.32-4.42, 6.86, 7.19, 7.27, 7.42-7.62, 7.73, 8.73, 9.38.

Example 22: 4-[2-({[(2'R,4S)-6-benzoyl-2,3-dihydrospiro[chromene-4,1'-cyclopropan]-2'-yl]carbonyl}amino)-4-cyanophenyl]butanoic acid The title compound having the following physical property values was obtained by performing the same procedures as those of Example 1 using the compound produced in Reference Example 26, instead of the compound produced in Reference Example 12.

TLC: Rf 0.42 (dichloromethane:methanol=9:1);
$^1$H-NMR (DMSO-d$_6$): δ 1.53-1.64, 1.64-1.78, 2.10-2.30, 2.41-2.75, 3.20-3.49, 4.10-4.23, 4.33-4.45, 6.94, 7.36-7.45, 7.46-7.59, 7.60-7.73, 7.87, 9.89, 12.09.

Example 23

The title compounds having the following physical property values were obtained by performing the same procedures as those of Reference Example 26→Example 1, except that the phenylboronic acid was replaced with a corresponding boronic acid.

Example 23-1: 4-[4-cyano-2-({[(2'R,4S)-6-(cyclopropylcarbonyl)-2,3-dihydrospiro[chromene-4,1'-cyclopropan]-2'-yl]carbonyl}amino)phenyl]butanoic acid TLC: Rf 0.41 (dichloromethane:methanol=9:1);
$^1$H-NMR (CDCl$_3$): δ 1.02-1.38, 1.67-1.83, 2.06-2.38, 2.45-2.78, 4.33-4.45, 4.53-4.67, 6.89, 7.19, 7.25-7.30, 7.87, 7.98, 8.88, 9.85.

Example 23-2: 4-[2-({[(2'R,4S)-6-acetyl-2,3-dihydrospiro[chromene-4,1'-cyclopropan]-2'-yl]carbonyl}amino)-4-cyanophenyl]butanoic acid TLC: Rf 0.40 (dichloromethane:methanol=9:1);
$^1$H-NMR (CDCl$_3$): δ 1.20-1.31, 1.70-1.85, 2.05-2.20, 2.23-2.33, 2.44-2.83, 4.33-4.45, 4.53-4.65, 6.85, 7.20, 7.28, 7.70, 8.06, 8.89, 9.83.

Reference Example 27: Ethyl 4-(4-cyano-2-{[(2'R,4S)-6-(methanesulfonyl)-2,3-dihydrospiro[1-benzopyran-4,1'-cyclopropane]-2'-carbonyl]amino}phenyl)butanoate In an argon atmosphere, sodium hydroxide (2.3 mg) was added to a 2-mL DMSO solution of L-proline (7 mg), and the mixture was stirred at room temperature for 30 min. To the resulting reaction mixture, the compound (40 mg) produced in Reference Example 10, copper iodide (11 mg), and sodium methanesulfinate (37 mg) were added, and the mixture was stirred at 100° C. for 1 h using a microwave reactor (Biotage, Ltd.). The reaction mixture was purified by silica gel column chromatography (Yamazen Autopurification Device) to obtain the title compound (33 mg) having the following physical property values.

TLC: Rf 0.58 (hexane:ethyl acetate=1:3);
$^1$H-NMR (CDCl$_3$): δ 1.13, 1.66-1.80, 1.91, 2.20-2.45, 2.53-2.64, 2.67, 3.01, 3.45-3.60, 3.73-3.86, 4.11-4.20, 4.40, 6.96, 7.20, 7.30, 7.40, 7.63, 8.71, 9.44.

Example 24: 4-[4-cyano-2-([(2'R,4S)-6-(methylsulfonyl)-2,3-dihydrospiro[chromene-4,1'-cyclopropan]-2'-yl]carbonyl}amino)phenyl]butanoic acid The title compound having the following physical property values was obtained by performing the same procedures as those of Example 1 using the compound produced in Reference Example 27, instead of the compound produced in Reference Example 12.

TLC: Rf 0.42 (dichloromethane:methanol=9:1);
$^1$H-NMR (DMSO-d$_6$): δ 1.53-1.64, 1.72, 1.80-1.87, 2.08-2.29, 2.35-2.74, 3.18, 4.05-4.20, 4.32-4.44, 7.02, 7.40, 7.42, 7.57, 7.64, 7.87, 9.95, 12.10.

Example 25: 4-[4-cyano-2-({[(2'R,4S)-6-(cyclopropylsulfonyl)-2,3-dihydrospiro[chromene-4,1'-cyclopropan]-2'-yl]carbonyl}amino)phenyl]butanoic acid The title compound having the following physical property values was obtained by performing the same procedures as those of Reference Example 27→Example 1, using sodium cyclopropanesulfinate instead of sodium methanesulfinate.

TLC: Rf 0.40 (dichloromethane:methanol=9:1);
$^1$H-NMR (CDCl$_3$): δ 1.00-1.15, 1.20-1.43, 1.60-1.82, 2.09-2.35, 2.38-2.60, 2.63-2.75, 3.39, 4.35, 4.57, 6.95, 7.20, 7.29, 7.59, 7.71, 8.90, 9.64.

Reference Example 28: (2'R,4S)-7-(benzyloxy)-2,3-dihydrospiro[1-benzopyran-4,1'-cyclopropane]-2'-carboxylic acid

[Chem. 106]

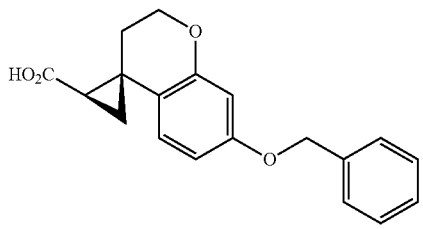

The title compound having the following physical property values was obtained by performing the same procedures as those of Reference Example 1→Reference Example 2→Reference Example 3, using 7-(benzyloxy)-2,3-dihydro-4H-chromen-4-one instead of 4-chromanone.

TLC: Rf 0.21 (hexane:ethyl acetate=1:1);
$^1$H-NMR (CDCl$_3$): δ 1.53-1.70, 2.07, 2.20, 4.20-4.09, 4.23-4.33, 5.01, 6.46, 6.52, 6.60, 7.27-7.44.

HPLC retention time: 12.2 min (CHIRALPAK IC 4.6 mm×250 mm hexane:ethyl acetate:formic acid=97:3:1).

Reference Example 29: Ethyl 4-(2-{[(2'R,4S)-7-(benzyloxy)-2,3-dihydrospiro[1-benzopyran-4,1'-cyclopropane]-2'-carbonyl]amino}-4-cyanophenyl)butanoate

[Chem. 107]

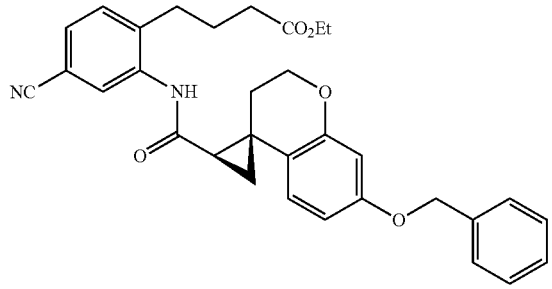

The title compound having the following physical property values was obtained by performing the same procedures as those of Reference Example 10 using the compound produced in Reference Example 28, instead of the compound produced in Reference Example 6.

$^1$H-NMR (CDCl$_3$): δ 1.13, 1.54-1.61, 1.64-1.81, 2.22, 2.37-2.45, 2.51-2.66, 3.55-3.68, 3.72-3.86, 4.03, 4.16, 4.22-4.32, 4.99, 6.42-6.51, 6.73, 7.18, 7.28, 7.29-7.44, 8.72, 9.28.

Example 26: 4-[2-({[(2'R,4S)-7-(benzyloxy)-2,3-dihydrospiro[chromene-4,1'-cyclopropan]-2'-yl]carbonyl}amino)-4-cyanophenyl]butanoic acid

[Chem. 108]

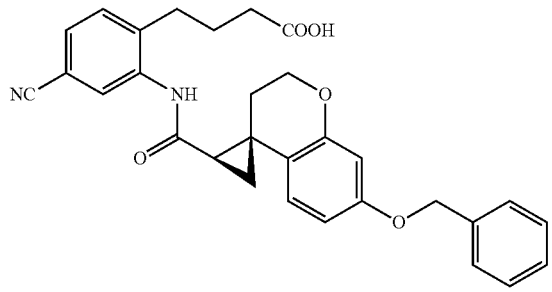

The title compound having the following physical property values was obtained by performing the same procedures as those of Example 1 using the compound produced in Reference Example 29, instead of the compound produced in Reference Example 12.

TLC: Rf 0.42 (dichloromethane:methanol=9:1);
$^1$H-NMR (CDCl$_3$): δ 1.58, 1.68-1.84, 2.10-2.20, 2.36, 2.46, 2.50-2.75, 4.03-4.16, 4.20-4.32, 5.02, 6.48, 6.54, 6.71, 7.20, 7.27-7.45, 8.54, 8.82.

Reference Example 30: Ethyl 4-(4-cyano-2-{[(2'R, 4S)-7-hydroxy-2,3-dihydrospiro[1-benzopyran-4,1'-cyclopropane]-2'-carbonyl]amino}phenyl)butanoate

[Chem. 109]

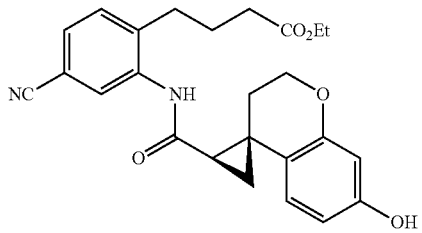

ASCA-2 (trade name, 50% wet, 300 mg) was added to a mixed solution of the compound (650 mg) produced in Reference Example 29 in ethanol (50 mL) and ethyl acetate (10 mL), and the mixture was stirred at room temperature for 8 h in a hydrogen atmosphere. The reaction mixture was filtered using Celite (trade name), and then the filtrate was concentrated under reduced pressure. The resulting residue was purified by silica gel column chromatography (Yamazen Autopurification Device) and then washed with tert-butyl methyl ether and hexane to obtain the title compound (368 mg) having the following physical property values.

TLC: Rf 0.28 (hexane:ethyl acetate=1:1);

$^1$H-NMR (CDCl$_3$): δ 1.16, 1.55-1.62, 1.66-1.80, 2.16-2.25, 2.38-2.47, 2.52-2.66, 3.60-3.73, 3.76-3.87, 4.04-4.15, 4.22-4.32, 4.63, 6.28-6.37, 6.69, 7.18, 7.28, 8.71, 9.28.

Example 27: 4-[4-cyano-2-({[(2'R,4S)-7-(3-pyridinyl)-2,3-dihydrospiro[chromene-4,1'-cyclopropan]-2'-yl]carbonyl}amino)phenyl]butanoic acid The title compound having the following physical property values was obtained by performing the same procedures as those of Reference Example 23→Reference Example 15→Example 1 using the compound produced in Reference Example 30 instead of the compound produced in Reference Example 20, using pyridine-3-boronic acid instead of 4-fluorophenylboronic acid.

TLC: Rf 0.39 (dichloromethane:methanol=9:1);

$^1$H-NMR (DMSO-d$_6$): δ 1.55-1.63, 1.65-1.80, 2.09-2.18, 2.21, 2.40-2.47, 2.53-2.77, 4.04-4.16, 4.28-4.38, 7.05, 7.15, 7.25, 7.41, 7.43-7.50, 7.57, 7.88, 8.02-8.08, 8.55, 8.85, 9.90, 12.10.

Example 28

The title compounds having the following physical property values were obtained by performing the same procedures as those of Reference Example 23→Reference Example 24→Reference Example 12→Example 1 using the compound produced in Reference Example 30 instead of the compound produced in Reference Example 20, using methylamine hydrochloride or 2-methoxyethylamine.

Example 28-1: 4-[4-cyano-2-({[(2'R,4S)-7-(methylcarbamoyl)-2,3-dihydrospiro[chromene-4,1'-cyclopropan]-2'-yl]carbonyl}amino)phenyl]butanoic acid

[Chem. 110]

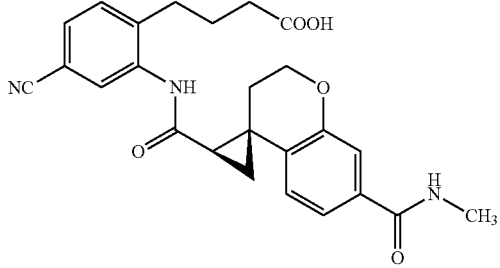

TLC: Rf 0.40 (dichloromethane:methanol=9:1);

$^1$H-NMR (DMSO-d$_6$): δ 1.56, 1.63-1.80, 2.02-2.15, 2.20, 2.42, 2.57-2.69, 2.74, 4.01-4.13, 4.23-4.37, 6.99, 7.24, 7.36, 7.40, 7.56, 7.86, 8.34, 9.89, 12.11.

Example 28-2: 4-[4-cyano-2-[({(2'R,4S)-7-[(2-methoxyethyl)carbamoyl]-2,3-dihydrospiro[chromene-4,1'-cyclopropan]-2'-yl}carbonyl)amino]phenyl}butanoic acid

[Chem. 111]

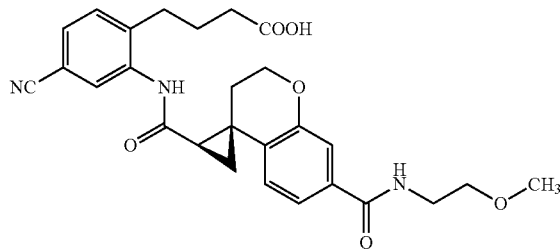

TLC: Rf 0.40 (dichloromethane:methanol=9:1);

$^1$H-NMR (CDCl$_3$): δ 1.63-1.89, 2.00-2.13, 2.25-2.47, 2.48-2.73, 2.78-2.93, 3.24-3.39, 3.51, 3.55-3.65, 3.85-4.06, 6.68, 6.79, 7.06, 7.20, 7.29, 7.98, 8.78, 9.84.

Example 29: 4-[2-({[(2'R,4S)-6-(benzyloxy)-2,3-dihydrospiro[chromene-4,1'-cyclopropan]-2'-yl]carbonyl}amino)-4-cyanophenyl]butanoic acid The title compound having the following physical property values was obtained by performing the same procedures as those of Reference Example 1→Reference Example 2→Reference Example 3→Reference Example 4→Reference Example 6→Reference Example 10→Example 1, using 6-(benzyloxy)-3,4-dihydro-2H-1-benzopyran-4-one instead of 4-chromanone, using iodoethane instead of iodomethane.

TLC: Rf 0.47 (dichloromethane:methanol=9:1);

$^1$H-NMR (CDCl$_3$): δ 1.46-1.55, 1.62-1.80, 2.12-2.18, 2.43-2.48, 2.51-2.76, 4.18-4.26, 4.95-5.07, 6.62, 6.75-6.80, 7.18, 7.28, 7.31-7.45, 8.68, 9.14.

Reference Example 31: Ethyl 4-(4-cyano-2-{[(2'R, 4S)-6-hydroxy-2,3-dihydrospiro[1-benzopyran-4,1'-cyclopropane]-2'-carbonyl]amino}phenyl)butanoate The title compound having the following physical property values was obtained by performing the same procedures as those of Reference Example 1→Reference Example 2→Reference Example 3→Reference Example 4→Reference Example 6→Reference Example 10→Reference Example 30, using 6-(benzyloxy)-3,4-dihydro-2H-1-benzopyran-4-one instead of 4-chromanone.

TLC: Rf 0.66 (hexane:ethyl acetate=1:2);
$^1$H-NMR (CDCl$_3$): δ 1.16, 1.52-1.58, 1.66-1.83, 2.21, 2.41, 2.55-2.73, 3.65-3.78, 3.84-3.98, 4.02-4.13, 4.17-4.27, 4.54, 6.33, 6.55, 6.68, 7.19, 7.28, 8.74, 9.38.

Example 30: 4-[4-cyano-2-({[(2'R,4S)-6-hydroxy-2,3-dihydrospiro[chromene-4,1'-cyclopropan]-2'-yl]carbonyl}amino)phenyl]butanoic acid The title compound having the following physical property values was obtained by performing the same procedures as those of Example 1, using the compound produced in Reference Example 31 instead of the compound produced in Reference Example 12.

TLC: Rf 0.38 (dichloromethane:methanol=9:1);
$^1$H-NMR (CD3OD): δ 1.55-1.70, 1.77-1.90, 2.11-2.20, 2.33, 2.40-2.48, 2.67-2.78, 4.04-4.15, 4.17-4.26, 6.28, 6.53, 6.64, 7.41, 7.48, 7.90.

Example 31

The title compounds having the following physical property values were obtained by performing the same procedures as those of Reference Example 21→Example 1, using the compound produced in Reference Example 31 instead of the compound produced in Reference Example 20, using 2-oxazolemethanol or methanol instead of (1-methylpyrazol-4-yl)methanol.

Example 31-1: 4-[4-cyano-2-({[(2'R,4S)-6-(1,3-oxazol-2-ylmethoxy)-2,3-dihydrospiro[chromene-4,1'-cyclopropan]-2'-yl]carbonyl}amino)phenyl]butanoic acid TLC: Rf 0.45 (dichloromethane:methanol=9:1);
$^1$H-NMR (CD3OD): δ 1.58-1.76, 1.77-1.90, 2.09-2.21, 2.33, 2.47, 2.72, 4.08-4.17, 4.18-4.29, 5.11, 6.53, 6.70, 6.77, 7.21, 7.42, 7.48, 7.92, 7.96.

Example 31-2: 4-(4-cyano-2-{(2'R,4S)-6-methoxy-2,3-dihydrospiro[1-benzopyran-4,1'-cyclopropane]-2'-carbonyl]amino}phenyl)butanoic acid TLC: Rf 0.35 (ethyl acetate);
$^1$H-NMR (DMSO-d$_6$) δ 1.50-1.56, 1.65-1.80, 2.00-2.09, 2.20, 2.35-2.47, 2.55-2.60, 2.61-2.69, 2.70-2.75, 3.69, 3.92-4.04, 4.15-4.26, 6.43, 6.71, 7.40, 7.56, 7.85, 9.86, 12.11.

Example 32: 4-[4-cyano-2-({[(2'R,4S)-7-(1,3-oxazol-2-ylmethoxy)-2,3-dihydrospiro[chromene-4,1'-cyclopropan]-2'-yl]carbonyl}amino)phenyl]butanoic acid The title compound having the following physical property values was obtained by performing the same procedures as those of Reference Example 21→Example 1, using the compound produced in Reference Example 30 instead of the compound produced in Reference Example 20, using 2-oxazolemethanol instead of (1-methylpyrazol-4-yl)methanol.

TLC: Rf 0.47 (dichloromethane:methanol=9:1);
$^1$H-NMR (CDCl$_3$): δ 1.58-1.68, 1.68-1.80, 2.03-2.15, 2.18-2.46, 2.41-2.50, 2.50-2.63, 2.64-2.83, 4.00-4.13, 4.20-4.31, 5.05, 5.17, 6.33, 6.48, 6.63, 7.10, 7.20, 7.28, 7.73, 8.62, 8.91.

Reference Example 32: Ethyl (2'R,4S)-7-methoxy-2,3-dihydrospiro[1-benzopyran-4,1'-cyclopropane]-2'-carboxylate

[Chem. 112]

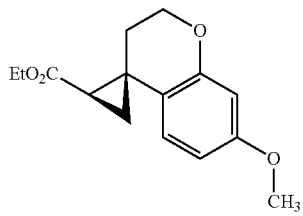

The same procedures as those of Reference Example 4 were performed using the compound produced in Reference Example 28 instead of the compound produced in Reference Example 3, using iodoethane instead of iodomethane. Palladium hydroxide/carbon (10% wet, 0.2 g) was added to a 5-mL ethyl acetate solution of the resulting compound (2.1 g), and the mixture was stirred at room temperature for 30 min in a hydrogen atmosphere. The reaction mixture was filtered using Celite (trade name), and then the filtrate was concentrated under reduced pressure. After adding potassium carbonate (1.46 g) to a 5-mL DMF solution of the resulting residue (1.31 g), iodomethane (1.5 g) was dropped, and the mixture was stirred overnight at room temperature. The reaction mixture was poured into ice water and extracted with a hexane-ethyl acetate mixed solution. The resulting organic layer was washed with water and saturated brine, dried over anhydrous sodium sulfate and then concentrated under reduced pressure to obtain the title compound (1.38 g) having the following physical property values.

TLC: Rf 0.69 (hexane:ethyl acetate=1:1);
$^1$H-NMR (CDCl$_3$): δ 1.25, 1.55-1.60, 2.05, 2.13-2.20, 3.75, 4.05-4.20, 4.23-4.31, 6.38, 6.45, 6.59.

Example 33

The title compounds having the following physical property values were obtained by performing the same procedures as those of Reference Example 5→Reference Example 6→Reference Example 10→Reference Example 11→Reference Example 12→Example 1, using the compound produced in Reference Example 32 instead of the compound produced in Reference Example 4, using methylamine hydrochloride or a corresponding amine compound.

Example 33-1: 4-[4-cyano-2-({[(2'R,4S)-7-methoxy-6-(methylcarbamoyl)-2,3-dihydrospiro[chromene-4,1'-cyclopropan]-2'-yl]carbonyl}amino)phenyl]butanoic acid

[Chem. 113]

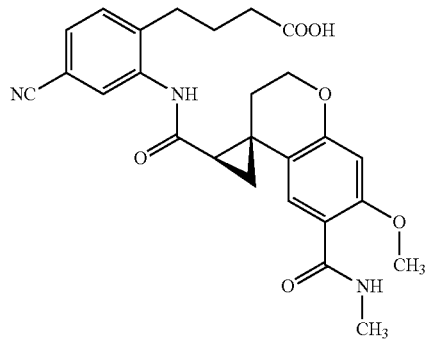

TLC: Rf 0.39 (dichloromethane:methanol=9:1);

$^1$H-NMR (DMSO-$d_6$): δ 1.42-1.60, 1.65-1.79, 2.00-2.29, 2.32-2.74, 2.77, 3.83, 4.05-4.17, 4.24-4.38, 6.54, 7.35-7.45, 7.55, 7.89, 7.98, 9.88, 12.12.

Example 33-2: 4-{4-cyano-2-[({(2'R,4S)-7-methoxy-6-[(2-methoxyethyl)carbamoyl]-2,3-dihydrospiro[chromene-4,1'-cyclopropan-2'-yl}carbonyl)amino]phenyl}butanoic acid

[Chem. 114]

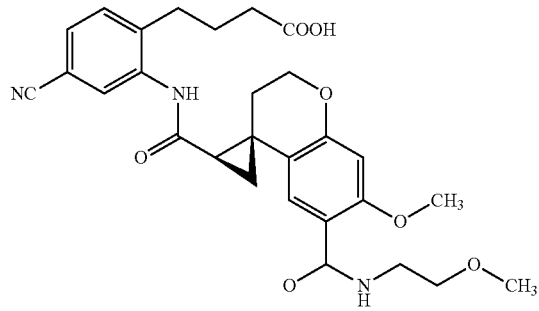

TLC: Rf 0.39 (dichloromethane:methanol=9:1);

$^1$H-NMR (DMSO-$d_6$): δ 1.46-1.60, 1.64-1.81, 2.00-2.29, 2.36-2.76, 3.27, 3.38-3.48, 3.85, 4.06-4.18, 4.25-4.36, 6.56, 7.40, 7.41, 7.55, 7.89, 8.09, 9.87, 12.10.

Example 33-3: 4-[4-cyano-2-({[(2'R,4S)-6-(ethylcarbamoyl)-7-methoxy-2,3-dihydrospiro[chromene-4,1'-cyclopropan]-2'-yl]carbonyl}amino)phenyl]butanoic acid TLC: Rf 0.54 (hexane:ethyl acetate=1:3);

$^1$H-NMR (DMSO-$d_6$): δ 1.09, 1.47-1.58, 1.65-1.78, 2.04-2.23, 2.47, 2.60-2.69, 3.21-3.30, 3.84, 4.11, 4.30, 6.54, 7.35-7.44, 7.56, 7.89, 8.04, 9.88, 12.11.

Example 33-4: 4-[4-cyano-2-({[(2'R,4S)-7-methoxy-6-(propylcarbamoyl)-2,3-dihydrospiro[chromene-4,1'-cyclopropan]-2'-yl]carbonyl}amino)phenyl]butanoic acid TLC: Rf 0.70 (hexane:ethyl acetate=1:3);

$^1$H-NMR (DMSO-$d_6$): δ 0.87, 1.41-1.58, 1.63-1.76, 2.00-2.23, 2.43, 2.59-2.70, 3.13-3.28, 3.84, 4.11, 4.29, 6.55, 7.32-7.42, 7.56, 7.90, 8.02, 9.88, 12.11.

Example 33-5: 4-[4-cyano-2-({[(2'R,4S)-6-(isopropylcarbamoyl)-7-methoxy-2,3-dihydrospiro[chromene-4,1'-cyclopropan]-2'-yl]carbonyl}amino)phenyl]butanoic acid TLC: Rf 0.68 (hexane:ethyl acetate=1:3);

$^1$H-NMR (DMSO-$d_6$): δ 1.14, 1.46-1.58, 1.63-1.78, 2.01-2.22, 2.46, 2.58-2.69, 3.84, 3.97-4.16, 4.31, 6.55, 7.34-7.43, 7.56, 7.74, 7.89, 9.87, 12.09.

Example 34: 4-[4-cyano-2-({[(2'R,4S)-7-methoxy-6-(5-methyl-1,3,4-oxadiazol-2-yl)-2,3-dihydrospiro[chromene-4,1'-cyclopropan]-2'-yl]carbonyl}amino)phenyl]butanoic acid The title compound having the following physical property values was obtained by performing the same procedures as those of Reference Example 5→Reference Example 6→Reference Example 10→Reference Example 11→Reference Example 13→Example 1, using the compound produced in Reference Example 32 instead of the compound produced in Reference Example 4.

TLC: Rf 0.38 (dichloromethane:methanol=9:1);

$^1$H-NMR (CDCl$_3$): δ 1.16-1.27, 1.50-1.58, 1.66-1.85, 2.09-2.30, 2.42-2.83, 3.46, 3.85, 4.35, 4.55, 6.48, 7.19, 7.27, 7.68, 8.88, 9.90.

Example 35: 4-[4-cyano-2-({[(2'R,4S)-6-(4-morpholinyl)-2,3-dihydrospiro[chromene-4,1'-cyclopropan]-2'-yl]carbonyl}amino)phenyl]butanoic acid Cesium carbonate (129 mg), [(2-dicyclohexylphosphino-2',4',6'-triisopropyl-1,1'-biphenyl)[2-(2-aminoethyl)phenyl]palladium(II) chloride (9 mg), and morpholine (34 mg) were added to a 1-mL DMF solution of the compound (72 mg) produced in Reference Example 10, and the mixture was stirred at 110° C. for 1 h using a microwave reactor (Biotage, Ltd.). A potassium carbonate aqueous solution was poured into the reaction mixture, and the mixture was extracted with ethyl acetate. The resulting organic layer was washed with saturated brine, dried over anhydrous magnesium sulfate and then concentrated under reduced pressure. The resulting residue was purified by silica gel column chromatography (Yamazen Autopurification Device) to obtain an ethyl ester (46 mg). The title compound was obtained by performing the same reaction as that of Example 1 using the resulting ethyl ester, instead of the compound produced in Reference Example 12.

TLC: Rf 0.36 (dichloromethane:methanol=9:1);

$^1$H-NMR (DMSO-$d_6$): δ 1.45-1.55, 1.62-1.80, 2.00-2.10, 2.16-2.26, 2.32-2.77, 2.89-3.06, 3.65-3.78, 3.90-4.05, 4.13-4.26, 6.39, 6.67, 6.74, 7.40, 7.56, 7.84, 9.87, 12.08.

Reference Example 33: Ethyl 4-(4-cyano-2-{[(2'R,3S)-5-iodo-2H-spiro[1-benzofuran-3,1'-cyclopropane]-2'-carbonyl]amino}phenyl)butanoate

[Chem. 115]

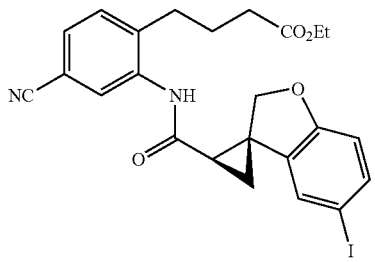

The title compound having the following physical property values was obtained by performing the same procedures as those of Reference Example 1→Reference Example 2→Reference Example 3→Reference Example 4→Reference Example 5→Reference Example 6→Reference Example 10, using 3-coumaranone instead of 4-chromanone, using iodoethane instead of iodomethane.

$^1$H-NMR (CDCl$_3$): δ 1.32, 1.57, 1.66-1.82, 2.36-2.70, 2.79, 3.95-4.22, 4.70, 6.60, 7.02, 7.20, 7.24-7.32, 7.38, 8.74, 9.40.

Example 36: 4-[4-cyano-2-({[(2'R,3S)-5-(3-pyridinyl)-2H-spiro[1-benzofuran-3,1'-cyclopropan]-2'-yl]carbonyl}amino)phenyl]butanoic acid

[Chem. 116]

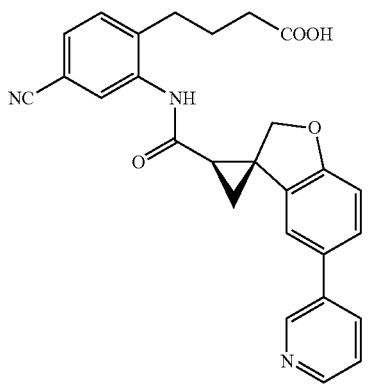

The title compound having the following physical property values was obtained by performing the same procedures as those of Reference Example 15→Example 1 using the compound produced in Reference Example 33 instead of the compound produced in Reference Example 10, using pyridine-3-boronic acid instead of 4-fluorophenylboronic acid.

TLC: Rf 0.42 (dichloromethane:methanol=9:1);

$^1$H-NMR (CDCl$_3$): δ 1.06, 1.62-1.92, 2.58, 2.78, 2.94, 4.85, 6.47, 6.87, 7.01-7.40, 8.41, 8.61, 8.79, 9.75.

Example 37

The title compounds having the following physical property values were obtained by performing the same procedures as those of Reference Example 11→Reference Example 12→Example 1, using the compound produced in Reference Example 33 instead of the compound produced in Reference Example 10, using methylamine hydrochloride or 2-methoxyethylamine.

Example 37-1: 4-[4-cyano-2-({[(2'R,3S)-5-(methylcarbamoyl)-2H-spiro[1-benzofuran-3,1'-cyclopropan]-2'-yl]carbonyl}amino)phenyl]butanoic acid

[Chem. 117]

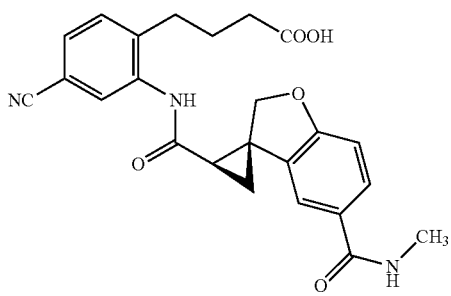

TLC: Rf 0.47 (dichloromethane:methanol=9:1);

$^1$H-NMR (CDCl$_3$): δ 1.57, 1.61-1.86, 2.30-2.73, 3.02, 3.22, 4.59, 4.73, 6.18, 6.76, 7.18, 7.20-7.32, 7.59, 8.70, 9.51.

Example 37-2: 4-{4-cyano-2-[({(2'R,3S)-5-[(2-methoxyethyl)carbamoyl]-2H-spiro[1-benzofuran-3,1'-cyclopropan]-2'-yl}carbonyl)amino]phenyl}butanoic acid

[Chem. 118]

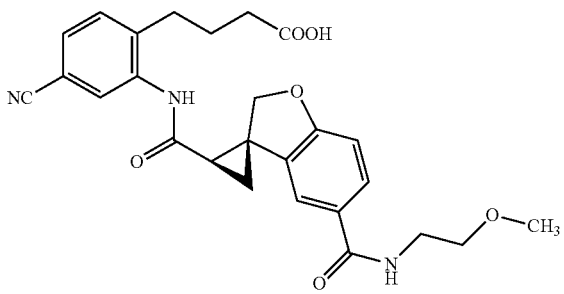

TLC: Rf 0.57 (dichloromethane:methanol=9:1);

$^1$H-NMR (CDCl$_3$): δ 1.58, 1.60-1.85, 2.30-2.75, 3.19, 3.41, 3.50-3.73, 4.61, 4.74, 6.47-6.62, 6.77, 7.19, 7.21-7.40, 7.56, 8.72, 9.47.

Reference Example 34:
6-iodo-3,3-dimethyl-2,3-dihydro-1H-inden-1-one

[Chem. 119]

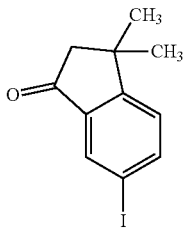

A sodium nitrite aqueous solution (4.5 mol/L, 4 mL) was dropped into a hydrochloric acid aqueous solution (5 mol/L, 15 mL) of 6-amino-3,3-dimethyl-indan-1-one (2.1 g) under ice-cooling, and then the mixture was stirred for 30 min. After confirming the disappearance of the raw materials, a potassium iodide aqueous solution (4 mol/L, 6 mL) was dropped into the mixture under ice-cooling. The mixture was then stirred at room temperature for 1 h after adding acetonitrile (20 mL). A saturated sodium bicarbonate aqueous solution was added to the reaction mixture under ice-cooling, and then the mixture was extracted with ethyl acetate. The resulting organic layer was washed with a saturated sodium thiosulfate aqueous solution, dried over anhydrous sodium sulfate and then concentrated under reduced pressure. The resulting residue was purified by silica gel column chromatography to obtain the title compound (2.66 g) having the following physical property values.

TLC: Rf 0.86 (hexane:ethyl acetate=1:1);
$^1$H-NMR (CDCl$_3$): δ 1.38-1.44, 2.59, 7.25-7.30, 7.90, 8.03.

Reference Example 35: Ethyl 4-(4-cyano-2-{[(1S,2R)-6'-iodo-3',3'-dimethyl-2',3'-dihydrospiro[cyclopropane-1,1'-indene]-2-carbonyl]amino}phenyl)butanoate

[Chem. 120]

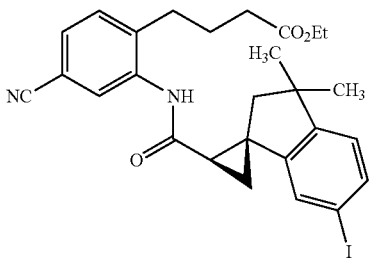

The title compound having the following physical property values was obtained by performing the same procedures as those of Reference Example 1→Reference Example 2→Reference Example 3→Reference Example 10, using the compound produced in Reference Example 34 instead of 4-chromanone.

$^1$H-NMR (CDCl$_3$): δ 1.14-1.35, 1.44, 1.64-1.79, 1.79-1.88, 2.17, 2.28-2.50, 2.50-2.71, 3.83, 4.05, 6.91, 7.11, 7.19, 7.22-7.31, 7.45-7.53, 8.79, 9.28.

Example 38

The title compounds having the following physical property values were obtained by performing the same procedures as those of Reference Example 11→Reference Example 12→Example 1, using the compound produced in Reference Example 35 instead of the compound produced in Reference Example 10, using methylamine hydrochloride or 2-methoxyethylamine.

Example 38-1: 4-[4-cyano-2-({[(1S,2R)-6'-[(2-methoxyethyl)carbamoyl-3',3'-dimethyl-2',3'-dihydrospiro[cyclopropane-1,1'-inden]-2-yl]carbonyl}amino)phenyl]butanoic acid

[Chem. 121]

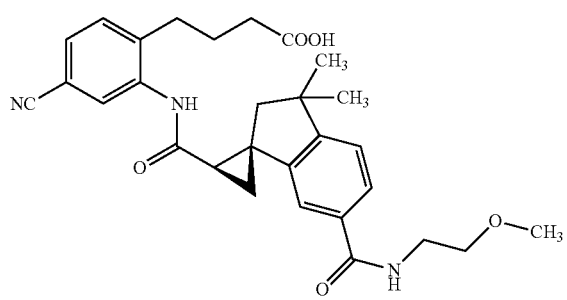

TLC: Rf 0.64 (ethyl acetate:methanol=9:1);
$^1$H-NMR (CDCl$_3$): δ 1.28-1.40, 1.72, 1.86, 2.01-2.10, 2.14-2.23, 2.63, 3.16, 3.40, 3.53-3.81, 6.64, 7.17, 7.22-7.31, 7.33-7.44, 7.70, 8.82, 9.51.

Example 38-2: 4-[4-cyano-2-({[(1S,2R)-3',3'-dimethyl-6'-(methylcarbamoyl-2',3'-dihydrospiro[cyclopropane-1,1'-inden]-2-yl]carbonyl}amino)phenyl]butanoic acid

[Chem. 122]

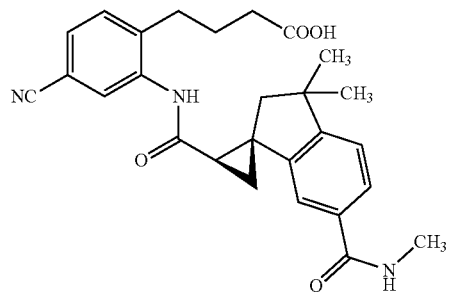

TLC: Rf 0.55 (ethyl acetate:methanol=9:1);
$^1$H-NMR (CDCl$_3$): δ 1.29-1.42, 1.63-1.80, 1.83-1.90, 1.98-2.11, 2.11-2.24, 2.32-2.56, 2.57-2.69, 3.04, 3.19, 6.24, 7.11-7.19, 7.21-7.34, 7.72, 8.82, 9.57.

Example 39: 4-[4-cyano-2-({[(1S,2R)-3',3'-dimethyl-6'-(3-pyridinyl)-2',3'-dihydrospiro[cyclopropane-1,1'-inden]-2-yl]carbonyl}amino)phenyl]butanoic acid

[Chem. 123]

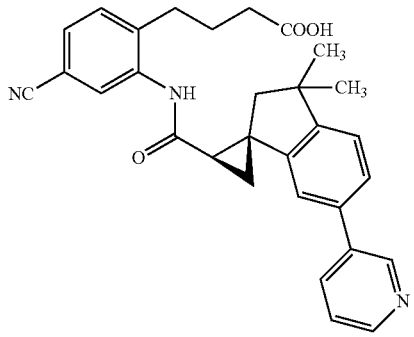

The title compound having the following physical property values was obtained by performing the same procedures as those of Reference Example 15→Example 1 using the compound produced in Reference Example 35 instead of the compound produced in Reference Example 10, using pyridine-3-boronic acid instead of 4-fluorophenylboronic acid.

TLC: Rf 0.62 (ethyl acetate:methanol=9:1);

$^1$H-NMR (CDCl$_3$): δ 0.59, 1.27-1.43, 1.55-1.69, 1.79, 2.18-2.38, 2.52-2.64, 2.64-2.91, 6.53, 7.16-7.35, 7.54, 8.39-8.50, 8.75-8.84, 9.35.

PHARMACOLOGICAL EXAMPLES

Pharmacological Example 1: EP$_4$ Antagonistic Activity Measurement Experiment Using Prostanoid Receptor Subtype-Expressing Cells CHO cells expressing rat EP$_4$ receptor subtypes were prepared according to the methods of Nishigaki et al. (Non-Patent Document 4) and used for experiment. Cultured subconfluent cells were detached and suspended in an assay medium (MEM containing 1 mmol/L IBMX, 1% HSA) in a concentration of 1×10$^6$ cells/mL. To start the reaction, PGE$_2$ was added to the cell suspension (25 μL) in a final concentration of 10 nmol/L, either alone or as a 25-μL PGE$_2$ solution containing a test compound. After 30 minutes of reaction at room temperature, the amount of cAMP in the cells was quantified according to the method in the descriptions of the cAMP assay kit (CISBIO).

The antagonistic effect (IC$_{50}$ value) of the test compound was calculated as a value that represents an inhibition rate against a reaction with PGE$_2$ alone at 10 nM, a concentration that produces a submaximal cAMP producing effect.

As a result, the compounds used for the present invention were shown to have strong EP$_4$ receptor antagonistic activity. For example, the IC$_{50}$ values of some of the compounds used for the present invention were as shown in Table 1 below. The EP$_4$ receptor antagonistic activity of Example 8-128 of Patent Document 2 was very weak, 2,800 nM.

TABLE 1

| Example | EP4 antagonistic activity (IC$_{50}$, nM) |
|---|---|
| 1 | 2.5 |
| 2-2 | 5.3 |
| 2-3 | 3.5 |
| 2-4 | 3.3 |
| 2-5 | 1.3 |
| 2-9 | 4.5 |
| 2-10 | 4.0 |
| 2-13 | 7.8 |
| 2-14 | 4.5 |
| 2-23 | 4.5 |
| 2-29 | 2.5 |
| 2-32 | 3.7 |
| 2-33 | 9.7 |
| 2-36 | 5.4 |
| 2-37 | 3.4 |
| 2-38 | 4.7 |
| 2-39 | 3.4 |
| 2-40 | 7.2 |
| 2-41 | 3.4 |
| 2-43 | 3.6 |
| 2-44 | 2.5 |
| 2-45 | 8.3 |
| 2-46 | 3.0 |
| 3 | 2.7 |
| 5 | 2.8 |
| 7-1 | 17 |
| 7-3 | 3.8 |
| 7-4 | 2.4 |
| 7-10 | 8.6 |
| 7-13 | 3.5 |
| 7-16 | 5.7 |
| 7-17 | 6.1 |
| 7-19 | 4.5 |
| 7-21 | 10 |
| 10-3 | 5.7 |
| 10-4 | 3.5 |
| 10-5 | 4.1 |
| 10-9 | 6.7 |
| 18-1 | 1.2 |
| 18-2 | 3.0 |
| 18-3 | 2.7 |
| 20-1 | 8.5 |
| 20-2 | 1.6 |
| 20-5 | 9.5 |
| 28-1 | 6.4 |
| 28-2 | 6.9 |
| 33-1 | 10 |
| 33-2 | 8.4 |
| 36 | 4.5 |
| 37-1 | 7.2 |
| 37-2 | 6.2 |
| 38-1 | 5.4 |
| 38-2 | 4.3 |
| 39 | 5.7 |

The following test was conducted using 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid (the compound of Example 2-13) as an EP$_4$ receptor antagonist represented by formula (I).

Pharmacological Example 2-1: Effect of Combination Therapy with Compound of Example 2-13 and Anti-Mouse PD-1 Antibody in Allograft Model of Mouse Colorectal Cancer Cell Line MC38

The effect of the combination therapy with the compound of Example 2-13 and an anti-mouse PD-1 antibody was evaluated in an allograft model of a mouse colorectal cancer cell line, MC38 (Cancer Res. (1975), 35(9), p 2434-9). The MC38 cells were cultured in a DMEM medium containing 10 vol % FBS, 100 units/mL penicillin, and 100}μg/mL streptomycin in a $CO_2$ incubator. On the day of transplantation, the culture supernatant was removed, and then the MC38 cells were washed with PBS and collected. The collected MC38 cells were suspended in PBS and used as transplant cells. Under anesthesia, 200,000 transplant cells were subcutaneously transplanted into the right lateral abdominal regions of female C57BL/6 mice. On day 7 after the transplantation, the mice were divided into four groups of a vehicle group, an Example 2-13 compound-single therapy group, an anti-mouse PD-1 antibody-single therapy group, and a combination therapy group (the compound of Example 2-13 and the anti-mouse PD-1 antibody), each containing 10 individuals. The compound of Example 2-13 was repeatedly orally administered to the mice of the Example 2-13 compound-single therapy group and the combination therapy group at 3 mg/kg, once on day 7 after the transplantation and twice a day from day 8 after the transplantation to day 28 after the transplantation. The anti-mouse PD-1 antibody was intraperitoneally administered to the mice of the anti-mouse PD-1 antibody-single therapy group and the combination therapy group at a dose of 20 mg/kg on day 7 after the transplantation and at a dose of 10 mg/kg on day 13 and day 19 after the transplantation. Distilled water was repeatedly orally administered to the mice of the vehicle group and the anti-mouse PD-1 antibody group for the same period as that of the compound of Example 2-13. PBS was intraperitoneally administered to the mice of the vehicle group and the Example 2-13 compound group at the same timings as those of the anti-mouse PD-1 antibody. The tumor volumes (mm$^3$) were calculated by the following equation from the tumor lengths along the minor axis and the major axis which were measured using a digital caliper.

$$\text{Tumor Volume}=[(\text{Minor Axis})^2 \times \text{Major Axis}]/2 \qquad [\text{Math. 1}]$$

The changes in the tumor volumes of the groups with time are shown in FIG. 1. The results of the cases in which the tumor disappeared are shown in Table 2.

TABLE 2

| Administration Group | Cases of Disappearance of Tumor/Cases |
|---|---|
| Vehicle | 0/10 |
| Compound of Example 2-13 | 0/10 |
| Anti-Mouse PD-1 Antibody | 3/10 |
| Combination Therapy with Compound of Example 2-13 and Anti-Mouse PD-1 Antibody | 8/10 |

The above results show that the compound of Example 2-13 inhibited the tumor growth alone and further strongly inhibited the tumor growth when used in combination with the anti-mouse PD-1 antibody.

Pharmacological Example 2-2: Effect of Combination Therapy with Compound of Example 2-2 and Anti-Mouse PD-1 Antibody in Allograft Model of Mouse Colorectal Cancer Cell Line MC38

The effect of the combination therapy with the compound of Example 2-2 and an anti-mouse PD-1 antibody was evaluated in an allograft model of a mouse colorectal cancer cell line, MC38 (Cancer Res. (1975), 35(9), p 2434-9). The MC38 cells were cultured in a DMEM medium containing 10 vol % FBS, 100 units/mL penicillin, and 100 μg/mL streptomycin in a $CO_2$ incubator. On the day of transplantation, the culture supernatant was removed, and then the MC38 cells were washed with PBS and collected. The collected MC38 cells were suspended in PBS and used as transplant cells. Under anesthesia, 1,000,000 transplant cells were subcutaneously transplanted into the right lateral abdominal regions of female C57BL/6 mice. On day 8 after the transplantation, the mice were divided into four groups of a vehicle group, an Example 2-2 compound-single therapy group, an anti-mouse PD-1 antibody-single therapy group, and a combination therapy group (the compound of Example 2-2 and the anti-mouse PD-1 antibody), each containing 10 individuals. The compound of Example 2-2 was repeatedly orally administered to the mice of the Example 2-2 compound-single therapy group and the combination therapy group at 3 mg/kg twice a day from day 8 after the transplantation to day 24 after the transplantation. The anti-mouse PD-1 antibody was intraperitoneally administered to the mice of the anti-mouse PD-1 antibody-single therapy group and the combination therapy group at a dose of 20 mg/kg on day 8 after the transplantation and at a dose of 10 mg/kg on day 14 and day 20 after the transplantation. Distilled water was repeatedly orally administered to the mice of the vehicle group and the anti-mouse PD-1 antibody group for the same period as that of the compound of Example 2-2. PBS was intraperitoneally administered to the mice of the vehicle group and the Example 2-2 compound group at the same timings as those of the anti-mouse PD-1 antibody. The tumor volumes (mm$^3$) were calculated by the following equation from the tumor lengths along the minor axis and the major axis which were measured using a digital caliper.

$$\text{Tumor Volume}=[(\text{Minor Axis})^2 \times \text{Major Axis}]/2 \qquad [\text{Math. 2}]$$

The changes in the tumor volumes of the groups with time are shown in FIG. 2. The results show that the compound of Example 2-2 inhibited the tumor growth alone and further strongly inhibited the tumor growth when used in combination with the anti-mouse PD-1 antibody.

Pharmacological Example 3: Effect of Combination Therapy with Compound of Example 2-13 and Anti-Mouse CTLA-4 Antibody in Allograft Model of Mouse Colorectal Cancer Cell Line MC38

The effect of the combination therapy with the compound of Example 2-13 and an anti-mouse CTLA-4 antibody was evaluated in an allograft model of a mouse colorectal cancer cell line, MC38. The MC38 cells were cultured using a DMEM medium containing 10 vol % FBS, 2 mmol/L Glutamax, 100 units/mL penicillin, and 100 μg/mL streptomycin in a $CO_2$ incubator. On the day of transplantation, the culture supernatant was removed, and then the MC38 cells were washed with PBS and collected. The collected MC38 cells were suspended in PBS and used as transplant cells. Under anesthesia, 1,000,000 transplant cells were subcutaneously transplanted into the right lateral abdominal regions of female C57BL/6 mice. On day 7 after the transplantation, the mice were divided into four groups of a vehicle group, an Example 2-13 compound-single therapy group, an anti-mouse CTLA-4 antibody-single therapy group, and a combination therapy group (the compound of Example 2-13 and the anti-mouse CTLA-4 antibody), each containing 15 individuals. The compound of Example 2-13 was repeatedly orally administered to the mice of the Example 2-13 compound-single therapy group and the combination therapy group at 5 mg/kg twice a day from day 7 after the transplantation to day 28 after the transplantation. The anti-mouse CTLA-4 antibody was intraperitoneally administered to the mice of the anti-mouse CTLA-4 antibody-single therapy group and the combination therapy group at a dose of 10 mg/kg on day 7, day 10, day 14, and day 17 after the transplantation. Distilled water was repeatedly orally administered to the mice of the vehicle group and the anti-mouse CTLA-4 antibody group for the same period as that of the compound of Example 2-13. A mouse IgG1 antibody was intraperitoneally administered to the mice of the vehicle group at the same timings as those of the anti-CTLA-4 antibody. The tumor volumes ($mm^3$) were calculated by the following equation from the tumor lengths along the minor axis and the major axis and the tumor height which were measured using a digital caliper.

Tumor Volume=Minor Axis×Major Axis×Height× 0.52 [Math. 3]

The changes in the tumor volumes of the groups with time are shown in FIG. 3. The results show that the compound of Example 2-13 inhibited the tumor growth alone and further strongly inhibited the tumor growth when used in combination with the anti-mouse CTLA-4 antibody.

Pharmacological Example 4: Effect of Combination Therapy with Compound of Example 2-13 and Anti-Mouse PD-1 Antibody in Allograft Model of Mouse Fibrosarcoma Cell Line SalN The effect of the combination therapy with the compound of Example 2-13 and an anti-mouse PD-1 antibody was evaluated in an allograft model of a mouse fibrosarcoma cell line, SalN (Cancer Res. (2012), 72(4), p 917-27). The SalN cells were cultured using a DMEM medium containing 10 vol % FBS, 2 mmol/L Glutamax, 100 units/mL penicillin, and 100 μg/mL streptomycin in a $CO_2$ incubator. On the day of transplantation, the culture supernatant was removed, and then the SalN cells were washed with PBS and collected. The collected SalN cells were suspended in PBS and used as transplant cells. Under anesthesia, 2,000,000 transplant cells were subcutaneously transplanted into the right lateral abdominal regions of female A/J mice. On day 7 after the transplantation, the mice were divided into four groups of a vehicle group, an Example 2-13 compound-single therapy group, an anti-mouse PD-1 antibody-single therapy group, and a combination therapy group (the compound of Example 2-13 and the anti-mouse PD-1 antibody), each containing 15 individuals. The compound of Example 2-13 was repeatedly orally administered to the mice of the Example 2-13 compound-single therapy group and the combination therapy group at 5 mg/kg twice a day from day 7 after the transplantation to day 21 after the transplantation. The anti-mouse PD-1 antibody was intraperitoneally administered to the mice of the anti-mouse PD-1 antibody-single therapy group and the combination therapy group at a dose of 3 mg/kg on day 7, day 10, day 14, and day 17 after the transplantation. Distilled water was repeatedly orally administered to the mice of the vehicle group and the anti-mouse PD-1 antibody-single therapy group for the same period as that of the compound of Example 2-13. A mouse IgG1 antibody was intraperitoneally administered to the mice of the vehicle group and the Example 2-13 compound-single therapy group at the same timings as those of the anti-mouse PD-1 antibody. The tumor volumes ($mm^3$) were calculated by the following equation from the tumor lengths along the minor axis and the major axis and the tumor height which were measured using a digital caliper.

Tumor Volume=Minor Axis×Major Axis×Height× 0.52 [Math. 4]

The changes in the tumor volumes of the groups with time are shown in FIG. 4. As a result, the compound of Example 2-13 inhibited the tumor growth alone and further strongly inhibited the tumor growth when used in combination with the anti-mouse PD-1 antibody.

Pharmacological Example 5: Effect of Combination Therapy with Compound of Example 2-13 and Anti-Mouse PD-1 Antibody in Allograft Model of Mouse Colorectal Cancer Cell Line CT26

The effect of the combination therapy with the compound of Example 2-13 and an anti-mouse PD-1 antibody was evaluated in an allograft model of a mouse colorectal cancer cell line, CT26 (Cancer Res. (2013), 73(12), p3591-603). The CT26 cells were cultured using a RPMI medium containing 10 vol % FBS, 2 mmol/L Glutamax, 100 units/mL penicillin, and 100 μg/mL streptomycin in a CO2 incubator. On the day of transplantation, the culture supernatant was removed, and then the CT26 cells were washed with PBS and collected. The collected CT26 cells were suspended in PBS and used as transplant cells. Under anesthesia, 1,000,000 transplant cells were subcutaneously transplanted into the right lateral abdominal regions of female BALB/c mice. On day 7 after the transplantation, the mice were divided into four groups of a vehicle group, an Example 2-13 compound-single therapy group, an anti-mouse PD-1 antibody-single therapy group, and a combination therapy group (the compound of Example 2-13 and the anti-mouse PD-1 antibody), each containing 15 to 18 individuals. The compound of Example 2-13 was repeatedly orally administered to the mice of the Example 2-13 compound-single therapy group and the combination therapy group at 5 mg/kg twice a day from day 7 after the transplantation to day 21 after the transplantation. The anti-mouse PD-1 antibody was intraperitoneally administered to the mice of the anti-mouse PD-1 antibody-single therapy group and the combination therapy group at a dose of 3 mg/kg on day 7, day 10, day 14, and day 17 after the transplantation. Distilled water was repeatedly orally administered to the mice of the vehicle group and the anti-mouse PD-1 antibody-single therapy group for the same period as that of the compound of Example 2-13. A mouse IgG1 antibody was intraperitoneally administered to the mice of the vehicle group and the Example 2-13 compound-single therapy group at the same timings as those of the anti-mouse PD-1 antibody. The tumor volumes ($mm^3$) were calculated by the following equation from the tumor lengths along the minor axis and the major axis and the tumor height which were measured using a digital caliper.

Tumor Volume=Minor Axis×Major Axis×Height× 0.52 [Math. 5]

The changes in the tumor volumes of the groups with time are shown in FIG. 5.

As a result, the compound of Example 2-13 inhibited the tumor growth alone and further strongly inhibited the tumor growth when used in combination with the anti-mouse PD-1 antibody.

INDUSTRIAL APPLICABILITY

The combination of the present invention exhibits a strong anti-tumor effect and thus is useful for the treatment of cancer.

The invention claimed is:

1. A method for treating cancer comprising administering effective amounts of the compound represented by formula (I), a salt thereof, a solvate thereof, or an N-oxide thereof and an immune checkpoint inhibitor to a mammal in need thereof, wherein formula (I) represents

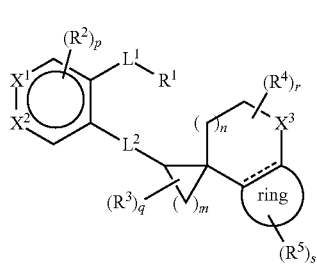

wherein $R^1$ represents $COOR^8$, tetrazole, $SO_3H$, $SO_2NH_2$, $SO_2NHR^{8-1}$, $CONHSO_2R^{8-1}$, $SO_2NHCOR^{8-1}$, or hydroxamic acid, wherein $R^8$ represents a hydrogen atom, C1-4 alkyl, or benzyl, and $R^{8-1}$ represents C1-4 alkyl, C1-4 haloalkyl, a C3-10 carbon ring, or a three- to ten-membered heterocyclic ring, wherein the C3-10 carbon ring and the three- to ten-membered heterocyclic ring each may be substituted with C1-4 alkyl, C1-4 haloalkyl, C1-4 alkoxy, —O(C1-4 haloalkyl), C1-4 alkylthio, —S(C1-4 haloalkyl), halogen, or nitrile, $L^1$ represents C1-5 alkylene, C2-5 alkenylene, or C2-5 alkynylene, $R^2$ represents halogen, C1-4 alkyl, C1-4 alkoxy, C1-4 alkylthio, C2-4 alkenyl, C2-4 alkynyl, —O(C1-4 haloalkyl), —S(C1-4 haloalkyl), —C(O)(C1-4 alkyl), —SO_2(C1-4 alkyl), —CONH(C1-4 alkyl), —CON(C1-4 alkyl)_2, —NHC(O)(C1-4 alkyl), —N(C 1-4 alkyl)C(O)(C1-4 alkyl), —NHSO_2(C1-4 alkyl), —N(C 1-4 alkyl)SO_2(C 1-4 alkyl), —SO_2NH(C 1-4 alkyl), —SO_2N(C 1-4 alkyl)_2, —NR^{17}R^{17}, nitro, nitrile, a hydroxyl group, aldehyde, or carboxyl, wherein the C1-4 alkyl groups each may be substituted with halogen, and the (C1-4 alkyl)$_2$ in R$^2$ represents two independent C1-4 alkyl groups which may be the same or different, X$^1$ represents CR$^6$, wherein R$^6$ represents a hydrogen atom, X$^2$ represents CR$^7$, wherein R$^7$ represents halogen or nitrile, L$^2$ represents —NHCO—, —CONH—, R$^3$ represents C1-4 alkyl or halogen, R$^4$ represents halogen, C1-4 alkyl, or C1-4 haloalkyl, X$^3$ represents methylene or an oxygen atom, the ring represents a benzene,

- - - - - represents a single bond or a double bond,

R$^5$ represents halogen, C1-4 alkyl, carboxyl, nitrile, —CONHR$^{11}$, —C(O)R$^{12}$, —OR$^{14}$, —S(O)$_r$R$^{15}$, —CH$_2$R$^{16}$, —NR$^{17}$R$^{17}$, NHCOR$^{11}$, a C4-10 carbon ring, or a four- to ten-membered heterocyclic ring, wherein the C4-10 carbon ring or the four- to ten-membered heterocyclic ring may be substituted with one to three R$^{18}$, wherein, when a plurality of R$^{18}$ exists, the plurality of R$^{18}$ each independently may be the same or different, R$^{11}$ represents C1-6 alkyl, C3-6 cycloalkyl, phenyl, or a four- to six-membered heterocyclic ring and may be substituted with one to three R$^{13}$, wherein, when a plurality of R$^{13}$ exists, the plurality of R$^{13}$ each independently may be the same or different, and R$^{13}$ represents halogen, C1-6 alkyl, C3-6 cycloalkyl, C1-4 alkoxy, a hydroxyl group, —NR$^{20}$R$^{21}$, benzene, or a four- to six-membered heterocyclic ring, wherein R$^{20}$ and R$^{21}$ each independently represent a hydrogen atom or C1-4 alkyl, R$^{12}$ represents C1-6 alkyl, C3-6 cycloalkyl, benzene, or a four- to six-membered heterocyclic ring, wherein the C3-6 cycloalkyl, the benzene, and the four- to six-membered heterocyclic ring each independently may be substituted with halogen, C1-4 alkyl, or C1-4 alkoxy, R$^{14}$ represents a hydrogen atom, C1-6 alkyl, C3-6 cycloalkyl, benzene, or benzyl, wherein the C1-6 alkyl may be substituted with one to three R$^{19}$, wherein, when a plurality of R$^{19}$ exists, the plurality of R$^{19}$ each independently may be the same or different, and R$^{19}$ represents C1-4 alkoxy, —CONH(C1-4 alkyl), —CON(C1-4 alkyl)$_2$, or a five- or six-membered monocyclic aromatic heterocyclic ring which may be substituted with a substituent selected from the group consisting of C1-4 alkyl and C1-4 haloalkyl, wherein the (C1-4 alkyl)$_2$ in R$^{19}$ represents two independent C1-4 alkyl groups which may be the same or different, R$^{15}$ represents C1-6 alkyl, C3-6 cycloalkyl, benzene, or benzyl, R$^{16}$ represents a hydroxyl group or C1-4 alkoxy, each R$^{17}$ independently represents a hydrogen atom, C1-6 alkyl, or C3-6 cycloalkyl, and R$^{18}$ represents halogen, C1-6 alkyl, C3-6 cycloalkyl, C1-4 alkoxy, oxo, nitrile, a hydroxyl group, hydroxymethyl, 1-methyl-1-hydroxyethyl, (C1-4 alkyl)SO$_2$—, a four- to six-membered heterocyclic ring, (C1-4 alkyl)NH—, or (C1-4 alkyl)$_2$N—, wherein the (C1-4 alkyl)$_2$ in R$^{18}$ represents two independent C1-4 alkyl groups which may be the same or different, m represents an integer of 1 to 4, n represents an integer of 0 to 4, p represents an integer of 0 to 2, q represents an integer of 0 to 6, r represents an integer of 0 to 6, s represents an integer of 0 to 4, t represents an integer of 0 to 2, and R$^2$, R$^3$, R$^4$, and R$^5$ each independently may be the same or different when p, q, r, and s are each an integer of 2 or more, wherein the cancer is treated by inhibiting prostaglandin E2 receptor 4 (EP4) and by inhibiting an immune checkpoint molecules; and wherein the cancer is leukemia, malignant lymphoma, multiple myeloma, myelodysplastic syndrome, head and neck cancer, esophageal cancer, esophageal adenocarcinoma, stomach cancer, duodenal cancer, colorectal cancer, colon cancer, rectal cancer, liver cancer, gallbladder/bile duct cancer, biliary tract cancer, pancreatic cancer, thyroid cancer, lung cancer, breast cancer, ovarian cancer, cervical cancer, corpus uteri cancer, endometrial cancer, vaginal cancer, vulvar cancer, renal cancer, renal pelvis/ureter cancer, urothelial cancer, penile cancer, prostate cancer, testicular tumor, osteosarcoma/soft tissue sarcoma, malignant bone tumor, skin cancer, thymoma, mesothelioma, or blood cancer.

2. The method according to claim 1, wherein the compound represented by formula (I) is a compound represented by formula (I-1),

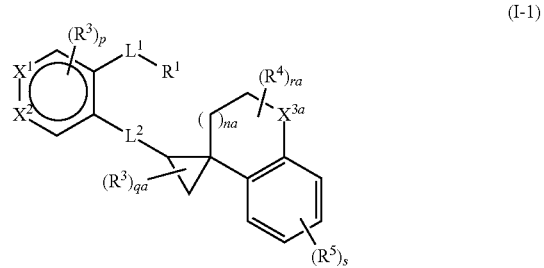

(I-1)

wherein na represents an integer of 0 or 1, qa represents an integer of 0 to 3, ra represents an integer of 0 to 4, X$^{3a}$a represents methylene or an oxygen atom, and the other symbols have the same meanings as the symbols defined in claim 1.

3. The method according to claim 1, wherein s is an integer of 1 to 4, and at least one R$^5$ is —CONHR$^{11}$.

4. The method according to claim 1, wherein the compound represented by formula (I) is a compound represented by formula (I-2),

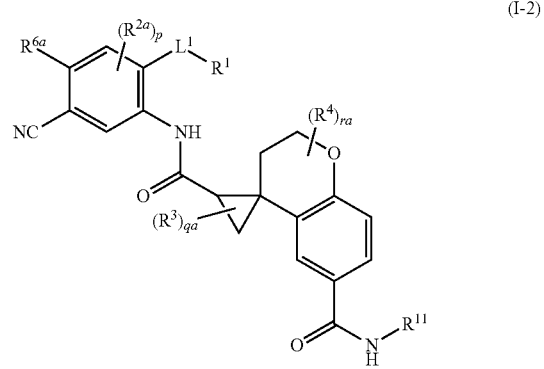

(I-2)

wherein R²ª represents halogen, R⁶ª represents a hydrogen atom, qa represents an integer of 0 to 3, ra represents an integer of 0 to 4, and the other symbols have the same meanings as the symbols defined in claim 1.

5. A method for treating cancer comprising administering an effective amount of 4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, or a solvate thereof and an immune checkpoint inhibitor to a mammal in need thereof,
wherein the cancer is treated by inhibiting prostaglandin E2 receptor 4 (EP4) and by inhibiting an immune checkpoint molecules, and
wherein the cancer is leukemia, malignant lymphoma, multiple myeloma, myelodysplastic syndrome, head and neck cancer, esophageal cancer, esophageal adenocarcinoma, stomach cancer, duodenal cancer, colorectal cancer, colon cancer, rectal cancer, liver cancer, gallbladder/bile duct cancer, biliary tract cancer, pancreatic cancer, thyroid cancer, lung cancer, breast cancer, ovarian cancer, cervical cancer, corpus uteri cancer, endometrial cancer, vaginal cancer, vulvar cancer, renal cancer, renal pelvis/ureter cancer, urothelial cancer, penile cancer, prostate cancer, testicular tumor, osteosarcoma/soft tissue sarcoma, malignant bone tumor, skin cancer, thymoma, mesothelioma, or blood cancer.

6. A method for treating cancer characterized by administering an effective amount of 4-[cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, or a solvate thereof to a patient, wherein the patient further receives treatment with an immune checkpoint inhibitor,
wherein the cancer is treated by inhibiting prostaglandin E2 receptor 4 (EP4) and by inhibiting an immune checkpoint molecules, and
wherein the cancer is leukemia, malignant lymphoma, multiple myeloma, myelodysplastic syndrome, head and neck cancer, esophageal cancer, esophageal adenocarcinoma, stomach cancer, duodenal cancer, colorectal cancer, colon cancer, rectal cancer, liver cancer, gallbladder/bile duct cancer, biliary tract cancer, pancreatic cancer, thyroid cancer, lung cancer, breast cancer, ovarian cancer, cervical cancer, corpus uteri cancer, endometrial cancer, vaginal cancer, vulvar cancer, renal cancer, renal pelvis/ureter cancer, urothelial cancer, penile cancer, prostate cancer, testicular tumor, osteosarcoma/soft tissue sarcoma, malignant bone tumor, skin cancer, thymoma, mesothelioma, or blood cancer.

7. A method for treating cancer characterized by administering an effective amount of an immune checkpoint inhibitor to a patient, wherein the patient further receives treatment with 4-[cyano-2-({[(2'R,4S)-6-(isopropylcarbamoyl)-2,3-dihydrospiro[chromene-4,1'-cyclopropan]-2'-yl]carbonyl}amino)phenyl]butanoic acid, a salt thereof, or a solvate thereof,
wherein the cancer is treated by inhibiting prostaglandin E2 receptor 4 (EP4) and by inhibiting an immune checkpoint molecules, and
wherein the cancer is leukemia, malignant lymphoma, multiple myeloma, myelodysplastic syndrome, head and neck cancer, esophageal cancer, esophageal adenocarcinoma, stomach cancer, duodenal cancer, colorectal cancer, colon cancer, rectal cancer, liver cancer, gallbladder/bile duct cancer, biliary tract cancer, pancreatic cancer, thyroid cancer, lung cancer, breast cancer, ovarian cancer, cervical cancer, corpus uteri cancer, endometrial cancer, vaginal cancer, vulvar cancer, renal cancer, renal pelvis/ureter cancer, urothelial cancer, penile cancer, prostate cancer, testicular tumor, osteosarcoma/soft tissue sarcoma, malignant bone tumor, skin cancer, thymoma, mesothelioma, or blood cancer.

8. The method according to claim 1, wherein the immune checkpoint inhibitor is an inhibitor of an immune checkpoint molecule selected from the group consisting of CTLA-4, PD-1, PD-L1, PD-L2, LAG-3, TIM3, BTLA, B7H3, B7H4, CD160, CD39, CD73, A2aR, KIR, VISTA, IDO 1, Arginase I, TIGIT, and CD115.

9. The method according to claim 1, wherein the immune checkpoint inhibitor is an anti-PD-1 antibody.

10. The method according to claim 1, wherein the immune checkpoint inhibitor is an anti-CTLA-4 antibody.

11. The method according to claim 1, wherein the cancer is selected from the group consisting of malignant lymphoma, head and neck cancer, esophageal cancer, stomach cancer, colorectal cancer, pancreatic cancer, lung cancer, renal cancer, and malignant melanoma.

12. A method for treating cancer comprising administering an effective amount of 4-[cyano-2-({[(2'R,4S)-6-(isopropylcarbamoyl)-2,3-dihydrospiro[chromene-4,1'-cyclopropan]-2'-yl]carbonyl}amino)phenyl]butanoic acid, or a salt thereof and an anti-PD-1 antibody to a mammal in need thereof, wherein the cancer is malignant lymphoma, head and neck cancer, esophageal cancer, stomach cancer, colorectal cancer, pancreatic cancer, lung cancer, renal cancer, malignant melanoma,
wherein the cancer is treated by inhibiting prostaglandin E2 receptor 4 (EP4) and by inhibiting an immune checkpoint molecules.

13. A method for treating cancer characterized by administering an effective amount of 4-[cyano-2-({[(2'R,4S)-6-(isopropylcarbamoyl)-2,3-dihydrospiro[chromene-4,1'-cyclopropan]-2'-yl]carbonyl}amino)phenyl]butanoic acid, or a salt thereof to a patient, wherein the patient further receives treatment with an anti-PD-1 antibody, wherein the cancer is malignant lymphoma, head and neck cancer, esophageal cancer, stomach cancer, colorectal cancer, pancreatic cancer, lung cancer, renal cancer, malignant melanoma,
wherein the cancer is treated by inhibiting prostaglandin E2 receptor 4 (EP4) and by inhibiting an immune checkpoint molecules.

14. A method for treating cancer characterized by administering an effective amount of an anti-PD-1 antibody to a patient, wherein the patient further receives treatment with 4[-cyano-2-({[(2'R,4S)-6-(isopropylcarbamoyl)-2,3-dihydrospiro[chromene-4,1'-cyclopropan]-2'-yl]carbonyl}amino)phenyl]butanoic acid, or a salt thereof, wherein the cancer is malignant lymphoma, head and neck cancer, esophageal cancer, stomach cancer, colorectal cancer, pancreatic cancer, lung cancer, renal cancer, malignant melanoma,
wherein the cancer is treated by inhibiting prostaglandin E2 receptor 4 (EP4) and by inhibiting an immune checkpoint molecules.

15. The method according to claim 5, wherein the immune checkpoint inhibitor is an inhibitor of an immune checkpoint molecule selected from the group consisting of CTLA-4, PD-1, PD-L1, PD-L2, LAG-3, TIM3, BTLA, B7H3, B7H4, CD160, CD39, CD73, A2aR, KIR, VISTA, IDO 1, Arginase I, TIGIT, and CD115.

16. The method according to claim 5, wherein the immune checkpoint inhibitor is an anti-PD-1 antibody.

17. The method according to claim 5, wherein the immune checkpoint inhibitor is an anti-CTLA-4 antibody.

18. The method according to claim 5, wherein the cancer is malignant lymphoma, head and neck cancer, esophageal cancer, stomach cancer, colorectal cancer, pancreatic cancer, lung cancer, renal cancer, malignant melanoma.

19. The method according to claim 6, wherein the immune checkpoint inhibitor is an inhibitor of an immune checkpoint molecule selected from the group consisting of CTLA-4, PD-1, PD-L1, PD-L2, LAG-3, TIM3, BTLA, B7H3, B7H4, CD160, CD39, CD73, A2aR, KIR, VISTA, IDO 1, Arginase I, TIGIT, and CD115.

20. The method according to claim 6, wherein the immune checkpoint inhibitor is an anti-PD-1 antibody.

21. The method according to claim 6, wherein the immune checkpoint inhibitor is an anti-CTLA-4 antibody.

22. The method according to claim 6, wherein the cancer is malignant lymphoma, head and neck cancer, esophageal cancer, stomach cancer, colorectal cancer, pancreatic cancer, lung cancer, renal cancer, malignant melanoma.

23. The method according to claim 7, wherein the immune checkpoint inhibitor is an inhibitor of an immune checkpoint molecule selected from the group consisting of CTLA-4, PD-1, PD-L1, PD-L2, LAG-3, TIM3, BTLA, B7H3, B7H4, CD160, CD39, CD73, A2aR, KIR, VISTA, IDO 1, Arginase I, TIGIT, and CD115.

24. The method according to claim 7, wherein the immune checkpoint inhibitor is an anti-PD-1 antibody.

25. The method according to claim 7, wherein the immune checkpoint inhibitor is an anti-CTLA-4 antibody.

26. The method according to claim 7, wherein the cancer is malignant lymphoma, head and neck cancer, esophageal cancer, stomach cancer, colorectal cancer, pancreatic cancer, lung cancer, renal cancer, malignant melanoma.

\* \* \* \* \*

UNITED STATES PATENT AND TRADEMARK OFFICE
CERTIFICATE OF CORRECTION

PATENT NO. : 11,065,226 B2
APPLICATION NO. : 16/315063
DATED : July 20, 2021
INVENTOR(S) : Takao Yoshida, Akiko Shoyama and Hirotsugu Takano It is certified that error appears in the above-identified patent and that said Letters Patent is hereby corrected as shown below:

In the Claims

Claim 1, Column 114, Lines 61-62, delete "-N(C 1-4 alkyl)C(O)(C1-4 alkyl)," and insert -- -N(C1-4 alkyl)C(O)(C1-4 alkyl),-- therefor;

Claim 2, Column 116, Line 42, delete "$X^{3\alpha}a$" and insert --$X^{3a}$-- therefor;

Claim 6, Column 117, Line 29-31, delete "4-[cyano-2-({[(2'R,4S)-6-(isopropylcarbamoyl)-2,3-dihydrospiro[chromene-4,1'-cyclopropan]-2'-yl]carbonyl}amino)phenyl]butanoic" and insert --4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic-- therefor;

Claim 7, Column 117, Line 54-56, delete "4-[cyano-2-({[(2'R,4S)-6-(isopropylcarbamoyl)-2,3-dihydrospiro[chromene-4,1'-cyclopropan]-2'-yl]carbonyl}amino)phenyl]butanoic" and insert --4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic-- therefor;

Claim 8, Column 118, Line 11, delete "IDO 1," and insert --IDO1,-- therefor;

Claim 12, Column 118, Lines 24-26, delete "4-[cyano-2-({[(2'R,4S)-6-(isopropylcarbamoyl)-2,3-dihydrospiro[chromene-4,1'-cyclopropan]-2'-yl]carbonyl}amino)phenyl]butanoic" and insert --4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic-- therefor;

Claim 13, Column 118, Line 36-38, delete "4-[cyano-2-({[(2'R,4S)-6-(isopropylcarbamoyl)-2,3-dihydrospiro[chromene-4,1'-cyclopropan]-2'-yl]carbonyl}amino)phenyl]butanoic" and insert --4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic-- therefor;

Signed and Sealed this
Ninth Day of August, 2022

Katherine Kelly Vidal
*Director of the United States Patent and Trademark Office*

CERTIFICATE OF CORRECTION (continued)
U.S. Pat. No. 11,065,226 B2

Page 2 of 2

Claim 14, Column 118, Lines 50-52, delete "4[-cyano-2-({[(2'R,4S)-6-(isopropylcarbamoyl)-2,3-dihydrospiro[chromene-4,1'-cyclopropan]-2'-yl]carbonyl}amino)phenyl]butanoic" and insert --4-[4-cyano-2-({[(2'R,4S)-6-(isopropylcarbamoyl)-2,3-dihydrospiro[chromene-4,1'-cyclopropan]-2'-yl]carbonyl}amino)phenyl]butanoic-- therefor;

Claim 15, Column 118, Line 64, delete "IDO 1," and insert --IDO1,-- therefor;

Claim 19, Column 119, Line 11, delete "IDO 1," and insert --IDO1,-- therefor; and Claim 23, Column 120, Line 7, delete "IDO 1," and insert --IDO1,-- therefor.